United States Patent [19]

Brown et al.

[11] Patent Number: 5,747,516

[45] Date of Patent: May 5, 1998

[54] DIHYDROAZOLE COMPOUNDS AND THEIR USE FOR CONTROLLING FUNGAL PLANT DISEASES

[75] Inventors: Richard James Brown, Newark; King-Mo Sun, Hockessin; Deborah Ann Frasier, Wilmington, all of Del.

[73] Assignee: E. I. du Pont de Nemours and Company, Wilmington, Del.

[21] Appl. No.: 640,884

[22] PCT Filed: Aug. 30, 1994

[86] PCT No.: PCT/US94/09525

§ 371 Date: May 8, 1996

§ 102(e) Date: May 8, 1996

[87] PCT Pub. No.: WO95/14009

PCT Pub. Date: May 26, 1995

[51] Int. Cl.$^6$ .......................... A61K 31/41; A61K 31/42; A61K 31/415; A61K 31/425

[52] U.S. Cl. .......................... 514/359; 514/372; 514/380; 514/384; 514/398; 514/404; 548/213; 548/243; 548/264.6; 548/325.5; 548/366.1; 548/364.4

[58] Field of Search .......................... 514/359, 360, 514/361, 372, 380, 404, 473, 384, 398, 266; 548/129, 132, 213, 243, 263.8, 264.6, 366.4, 325.5, 367.1, 366.1, 318.5, 374.1, 544

[56] References Cited

U.S. PATENT DOCUMENTS

| | | | |
|---|---|---|---|
| 4,000,155 | 12/1976 | Beck et al. | 260/310 |
| 4,065,463 | 12/1977 | Beck et al. | 260/307 |
| 4,098,896 | 7/1978 | Edwards | 424/269 |
| 4,504,486 | 3/1985 | Kurvov | 514/380 |
| 4,881,967 | 11/1989 | Semple | 71/92 |
| 5,258,527 | 11/1993 | Krauskopf et al. | 548/543 |
| 5,332,720 | 7/1994 | Kruger et al. | 504/281 |
| 5,358,924 | 10/1994 | Kruger et al. | 504/197 |

FOREIGN PATENT DOCUMENTS

| | | | |
|---|---|---|---|
| 398692 | 11/1990 | European Pat. Off. | C07C 251/40 |
| 0 508 126 | 10/1992 | European Pat. Off. | C07D 231/32 |
| 4032059 | 4/1992 | Germany | 548/543 |
| 44 13 669 | 1/1995 | Germany | C07D 307/94 |
| 1350582 | 4/1974 | United Kingdom | 548/543 |
| WO 92/16510 | 10/1992 | WIPO | C07D 231/32 |
| WO 93/07116 | 4/1993 | WIPO | C07C 271/28 |
| WO 95/01971 | 1/1995 | WIPO | C07D 307/94 |

OTHER PUBLICATIONS

Gury Zvilichovsky, "Crystal Structure and Tautomerism in 4-Phenylisoxazoles with Two Potential Hydroxyl Groups at Positions 3 and 5", *J. Heterocyclic Chem.*, 24, 465–470, Mar.–Apr. 1987.

Gury Zvilichovsky and Mordechai David, Acidity and Alkylation of 4-Phenyl-3, 5-dihydroxypyrazole and Its Derivatives. C versus O and N Alkylation. *J. Heterocyclic Chem.*, 25, 1307–1310, Sep.–Oct. 1988.

Davis et al., "Hydroxyisothiazoles. II* Preparation of Isothiazolin-3-ones and Their Methylated Derivatives from the Oxidation of Cyano-Substituted Dithioacetate Salts", *Aust. J. Chem.*, 30, 1815–1818, Mar. 3, 1977.

J.F.W. Keana et al., "Potent hydrophilic dienophiles. Synthesis and aqueous stability of several 4-aryl-and sulfonated 4-aryl-1,2,4-triazoline-3,5-dines and their immobilization on silica gel", *Journal of Organic Chemistry*, 48, No. 16, 2654–2660, 12 Aug. 1983.

*Chemical Abstracts*, 63, No. 6, 13 Sep. 1965, Abstract No. 6997.

*Chemical Abstracts*, 51, No. 14, 25 Jul. 1957, Abstract No. 10587i.

*Chemical Abstracts*, 53, No. 19, 10 Oct. 1959, Abstract No. 18013.

*Primary Examiner*—Yogendra N. Gupta

[57] ABSTRACT

Dihydroisoxazoles, dihydroisothiazoles, dihydropyrazoles, dihydrothiazoles and dihydroimidazoles of Formula I

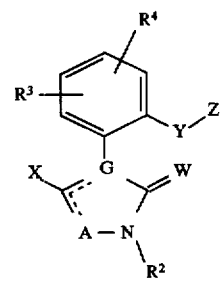

wherein:

A is O; S; N; NR$^5$; or CR$^{14}$;

G is C or N; provided that when G is C, A is O, S or NR$^5$ and the floating double bond is attached to G; and when G is N, A is N or CR$^{14}$ and the floating double bond is attached to A;

W is O or S;

X is OR$^1$, S(O)$_n$R$^1$ or halogen; and

Y, Z, R$^1$, R$^2$, R$^3$, R$^4$, R$^5$, R$^{14}$, and n are defined in the disclosure, are disclosed.

Also disclosed are fungicidal compositions containing these compounds, and use of these cyclic amide compounds for controlling plant diseases caused by fungal plant pathogens.

7 Claims, No Drawings

5,747,516

DIHYDROAZOLE COMPOUNDS AND THEIR USE FOR CONTROLLING FUNGAL PLANT DISEASES

This application is the national filing under 35 USC 371 of International Application No. PCT/US94/09525 filed Aug. 30, 1994, and is a continuation-in-part of U.S. patent application Ser. No. 08/155,970 filed Nov. 19, 1993 and U.S. patent application Ser. No. 08/155,963 filed Nov. 19, 1993.

BACKGROUND OF THE INVENTION

This invention relates to cyclic amides substituted at the α-position with various aryl groups, their agriculturally suitable salts and compositions, and methods of their use as general or selective fungicides.

EP-A-398,692 discloses amides of Formula i as fungicides for crop protection.
Compounds of Formula i are:

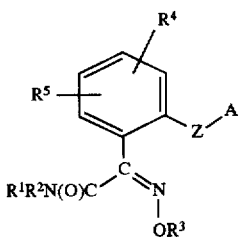

i wherein
$R^1$ and $R^2$ are each hydrogen, lower alky, or lower cycloalkyl.

All the compounds disclosed in EP-A-398,692 have an aryl moiety bonded to an acyclic alkoxyiminoacetamide group. The cyclic amides of the present invention are not disclosed therein.

WO 93/07116 discloses compounds of Formula ii as fungicides for crop protection. Compounds of Formula ii are:

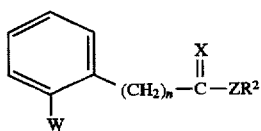

ii wherein:
W is

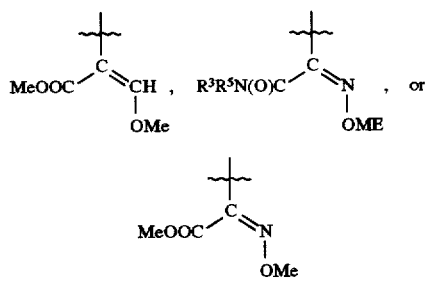

Once again, the cyclic amides of this invention are not disclosed therein. *J. Heterocyclic Chem.*, (1987), 24, 465, *J. Heterocyclic Chem.*, (1988), 25, 1307, and *Australian J. Chem.*, (1977), 30 (8), 1815 disclose 4-nitrophenyl isoxazoles (iii), phenyl pyrazolones (iv), and aryl isothiazolinones (v) respectively.

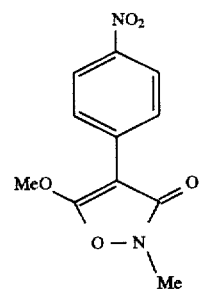

iii

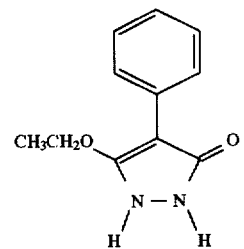

iv

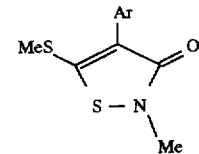

v

However, no utility as fungicides is alleged and no ortho-substituted compounds of the present invention are disclosed.

SUMMARY OF THE INVENTION

This invention comprises compounds of Formula I including all geometric and stereoisomers, agriculturally suitable salts thereof, agricultural compositions containing them and their use as fungicides:

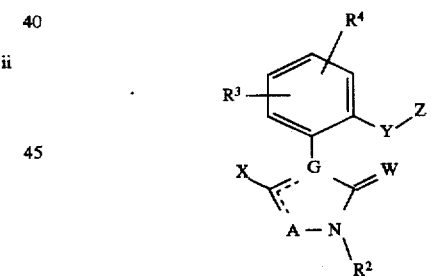

I wherein:
A is O; S; N; $NR^5$; or $CR^{14}$;

G is C or N; provided that when G is C, A is O, S or $NR^5$ and the floating double bond is attached to G; and when G is N, A is N or $CR^{14}$ and the floating double bond is attached to A;

W is O or S;

X is $OR^1$; $S(O)_mR^1$; or halogen;

$R^1$, $R^2$, and $R^5$ are each independently H; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl, $C_2$–$C_4$ alkoxycarbonyl; or benzoyl optionally substituted with $R^{13}$;

$R^3$ and $R^4$ are each independently H; halogen; cyano; nitro; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–$C_6$ haloalkynyl; $C_1$–$C_6$ alkoxy; $C_1$–$C_6$ haloalkoxy; $C_2$–$C_6$ alkenyloxy; or $C_2$–$C_6$ alkynyloxy;

Y is —O—; —S(O)$_n$—; —CHR$^6$CHR$^6$—; —CR$^6$=CR$^6$—; —C≡C—; —CHR$^6$O—; —OCHR$^6$—; —CHR$^6$S(O)$_n$—; —S(O)$_n$CHR$^6$—; —CHR$^6$O—N=C(R$^7$)—; —(R$^7$)C=N—OCH(R$^6$)—; —C(R$^7$)=N—O—; —O—N=C(R$^7$)—; —CHR$^6$OC(=O)N(R$^{15}$)—; or a direct bond; and the directionality of the Y linkage is defined such that the moiety depicted on the left side of the linkage is bonded to the phenyl ring and the moiety on the right side of the linkage is bonded to Z;

R$^6$ is independently H or $C_1$–$C_3$ alkyl;

R$^7$ is H; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_2$–$C_6$ haloalkynyl; $C_3$–$C_6$ cycloalkyl; $C_2$–$C_4$ alkylcarbonyl; $C_2$–$C_4$ alkoxycarbonyl; cyano; or morpholinyl;

Z is $C_1$–$C_{10}$ alkyl, $C_2$–$C_{10}$ alkenyl, or $C_2$–$C_{10}$ alkynyl each optionally substituted with R$^8$; or Z is $C_3$–$C_8$ cycloalkyl or phenyl each optionally substituted with one of R$^9$, R$^{10}$, or both R$^9$ and R$^{10}$; or Z is a 3 to 14-membered nonaromatic heterocyclic ring system selected from the group monocyclic ring, fused bicyclic ring and fused tricyclic ring, or Z is a 5 to 14-membered aromatic heterocyclic ring system selected from the group monocyclic ring, fused bicyclic ring and fused tricyclic ring, each nonaromatic or aromatic ring system containing 1 to 6 heteroatoms independently selected from the group 1–4 nitrogen, 1–2 oxygen, and 1–2 sulfur, each nonaromatic or aromatic ring system optionally substituted with one of R$^9$, R$^{10}$, or both R$^9$ and R$^{10}$; or R$^7$ and Z are taken together to form CH$_2$CH$_2$CH$_2$, CH$_2$CH$_2$CH$_2$CH$_2$, CH$_2$CH$_2$OCH$_2$CH$_2$, each CH$_2$ group optionally substituted with 1–2 halogen; or Y and Z are taken together to form

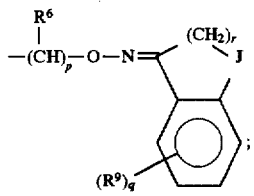

R$^3$, Y, and Z are taken together with the phenyl ring to form a naphthalene ring substituted on either ring with a floating R$^4$; provided that when R$^3$, Y, and Z are taken together with the phenyl ring to form a napthylene ring substituted by R$^4$, and A is S, W is O, X is SCH$_3$ and R$^2$ is CH$_3$, then R$^4$ is other than H;

J is —CH$_2$—; —CH$_2$CH$_2$13 ; OCH$_2$—; —CH$_2$O—; —SCH$_2$—; —CH$_2$S—; —N(R$^{16}$)CH$_2$—; or —CH$_2$N(R$^{16}$)—; each CH$_2$ group optionally substituted with 1 to 2 CH$_3$;

R$^8$ is 1–6 halogen; $C_1$–$C_6$ alkoxy; $C_1$–$C_6$ haloalkoxy; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; CO$_2$($C_1$–$C_6$ alkyl); NH($C_1$–$C_6$ alkyl); N($C_1$–$C_6$ alkyl)$_2$; cyano; or nitro; or R$^8$ is phenyl, phenoxy, pyridinyl, pyridinyloxy, thienyl, furanyl, pyrimidinyl, or pyrimidinyloxy each optionally substituted with one of R$^{11}$, R$^{12}$, or both R$^{11}$ and R$^{12}$;

R$^9$ is 1–2 halogen; $C_1$–$C_6$ alkyl; $C_1$–$C_6$ haloalkyl; $C_1$–$C_6$ alkoxy; $C_1$–$C_6$ haloalkoxy; $C_2$–$C_6$ alkenyl; $C_2$–$C_6$ haloalkenyl; $C_2$–$C_6$ alkynyl; $C_1$–$C_6$ alkylthio; $C_1$–$C_6$ haloalkylthio; $C_1$–$C_6$ alkylsulfinyl; $C_1$–$C_6$ alkylsulfonyl; $C_3$–$C_6$ cycloalkyl; $C_3$–$C_6$ alkenyloxy; CO$_2$($C_1$–$C_6$ alkyl); NH($C_1$–$C_6$ alkyl); N($C_1$–$C_6$ alkyl)$_2$; —C(R$^{18}$)=NOR$^{17}$; cyano; or nitro; or R$^9$ is phenyl, benzyl, benzoyl, phenoxy, pyridinyl, pyridinyloxy, thienyl, thienyloxy, furanyl, pyrimidinyl, or pyrimidinyloxy each optionally substituted with one of R$^{11}$, R$^{12}$, or both R$^{11}$ and R$^{12}$;

R$^{10}$ is halogen; $C_1$–$C_4$ alkyl; $C_1$–$C_4$ haloalkyl; $C_1$–$C_4$ alkoxy; nitro; or cyano; or R$^9$ and R$^{10}$, when attached to adjacent atoms, are taken together as —OCH$_2$O— or —OCH$_2$CH$_2$O—; each CH$_2$ group optionally substituted with 1–2 halogen;

R$^{11}$ and R$^{12}$ are each independently halogen; $C_1$–$C_4$ alkyl; $C_1$–$C_4$ haloalkyl; $C_1$–$C_4$ alkoxy; $C_1$–$C_4$ haloalkoxy; nitro; or cyano;

R$^{13}$ is halogen; $C_1$–$C_3$ alkyl; $C_1$–$C_3$ haloalkyl; $C_1$–$C_3$ alkoxy; $C_1$–$C_3$ haloalkoxy; nitro; or cyano;

R$^{14}$ is H; halogen; $C_1$–$C_6$ alkyl; $C_1$–$C_6$ haloalkyl; $C_2$–$C_6$ alkenyl; $C_2$–$C_6$ haloalkeny; $C_2$–$C_6$ alkynyl; $C_2$–$C_6$ haloalkynyl; or $C_3$–$C_6$ cycloalkyl;

R$^{15}$, R$^{16}$, R$^{17}$, and R$^{18}$ are each independently H; $C_1$–$C_3$ alkyl; or phenyl optionally substituted with halogen, $C_1$–$C_4$ alkyl, $C_1$–$C_4$ haloalkyl, $C_1$–$C_4$ alkoxy, $C1_1$–$C_4$ haloalkoxy, nitro or cyano; m, n and q are each independently 0, 1 or 2; and p and r are each independently 0 or 1.

In the above recitations, the term "alkyl", used either alone or in compound words such as "haloalkyl" denotes straight-chain or branched alkyl; e.g., methyl, ethyl, n-propyl, i-propyl, or the different butyl, pentyl or hexyl isomers. "Alkenyl" denotes straight-chain or branched alkenes; e.g., 1-propenyl, 2-propenyl, and the different butenyl, pentenyl and hexenyl isomers. "Alkenyl" also denotes polyenes such as 1,3-hexadiene. "Alkynyl" denotes straight-chain or branched alkynes; e.g., ethynyl, 1-propynyl, 3-propynyl and the different butynyl, pentynyl and hexynyl isomers. "Alkynyl" can also denote moieties comprised of multiple triple bonds; e.g., 2,4-hexadiyne. "Alkoxy" denotes, for example, methoxy, ethoxy, n-propyloxy, isopropyloxy and the different butoxy, pentoxy and hexyloxy isomers. "Alkenyloxy" denotes straight-chain or branched alkenyloxy moieties. Examples of alkenyloxy include H$_2$C=CHCH$_2$O,(CH$_3$)$_2$C=CHCH$_2$O, (CH$_3$)CH=CHCH$_2$O, (CH$_3$)CH=C(CH$_3$)CH$_2$O and CH$_2$=CHCH$_2$CH$_2$O. "Alkynyloxy" denotes straight-chain or branched alkynyloxy moieties. Examples include HC≡CCH$_2$O, CH$_3$C≡CCH$_2$O and CH$_3$C≡CCH$_2$CH$_2$O. The term "halogen", either alone or in compound words such as "haloalkyl", denotes fluorine, chlorine, bromine or iodine. Further, when used in compound words such as "haloalkyl", said alkyl may be partially or fully substituted with halogen atoms which may be the same or different. Examples of "haloalkyl" include F$_3$C, ClCH$_2$, CF$_3$CH$_2$ and CF$_3$CCl$_2$. The term "cycloalkyl" denotes cyclopropyl, cyclobutyl, cyclopentyl and cyclohexyl moieties. The term "nonaromatic heterocyclic ring system" includes fully saturated heterocycles and partially aromatic heterocycles. The total number of carbon atoms in a substituent group is indicated by the "$C_i$–$C_j$" prefix where i and j are numbers from 1 to 10. For example, $C_1$–$C_3$ alkyl designates methyl through propyl; $C_2$ alkoxy designates CH$_3$CH$_2$O; and $C_3$ alkoxy designates, for example, CH$_3$CH$_2$CH$_2$O or (CH$_3$)

$_2$CHO. In the above recitations, when a compound of Formula I is comprised of one or more aromatic nitrogen-containing rings (e.g., pyridinyl and pyrimidinyl), all bonds to these heterocycles are made through the carbon atom(s) of the moieties.

Preferred compounds, compositions containing them, and methods of their use for reasons of better activity and/or ease of synthesis are:

Preferred 1. Compounds of Formula I above wherein:

W is O;

$R^1$ is $C_1$–$C_3$ alkyl or $C_1$–$C_3$ haloalkyl;

$R^2$ is H; $C_1$–$C_6$ alkyl; $C_1$–$C_6$ haloalkyl; or $C_3$–$C_6$ cycloalkyl;

$R^3$ and $R^4$ are each independently H; halogen; cyano; nitro; $C_1$–$C_6$ alkyl; $C_1$–$C_6$ haloalkyl; $C_1$–$C_6$ alkoxy; or $C_1$–$C_6$ haloalkoxy;

Y is —O—; —CH=CH—; —CH$_2$O—; —OCH$_2$—; —CH$_2$S(O)$_n$—; —CH$_2$O—N=C(R$^7$)—; —C(R$^7$)=N—O—; —CH$_2$OC(O)NH—; or a direct bond;

$R^7$ is H; $C_1$–$C_6$ alkyl; $C_1$–$C_6$ haloalkyl; $C_2$–$C_6$ alkenyl; $C_2$–$C_6$ alkynyl; or cyano;

Z is $C_1$–$C_{10}$ alkyl optionally substituted with $R^8$; or $C_3$–$C_8$ cycloalkyl or phenyl, each optionally substituted with one of $R^9$, $R^{10}$, or both $R^9$ and $R^{10}$; or Z is

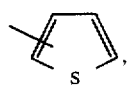 Z-1

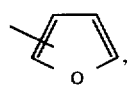 Z-2

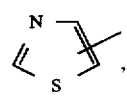 Z-3

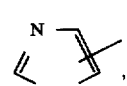 Z-4

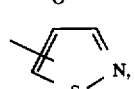 Z-5

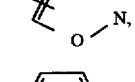 Z-6

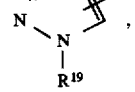 Z-7

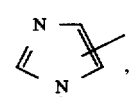 Z-8

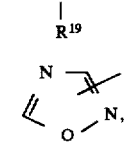 Z-9

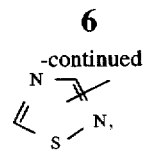 Z-10

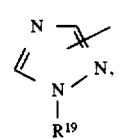 Z-11

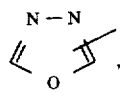 Z-12

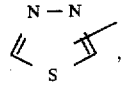 Z-13

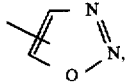 Z-14

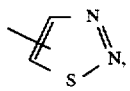 Z-15

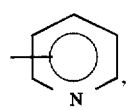 Z-16

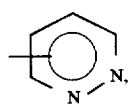 Z-17

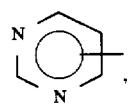 Z-18

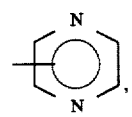 Z-19

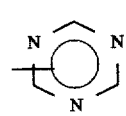 Z-20

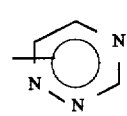 Z-21

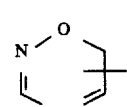 Z-22

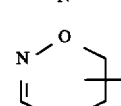 Z-23

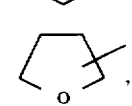 Z-24

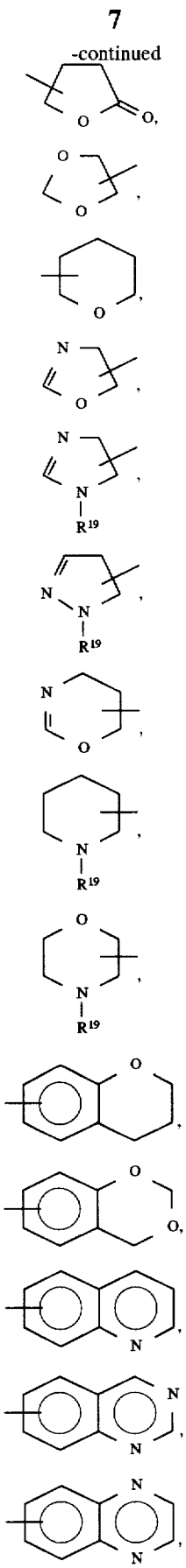
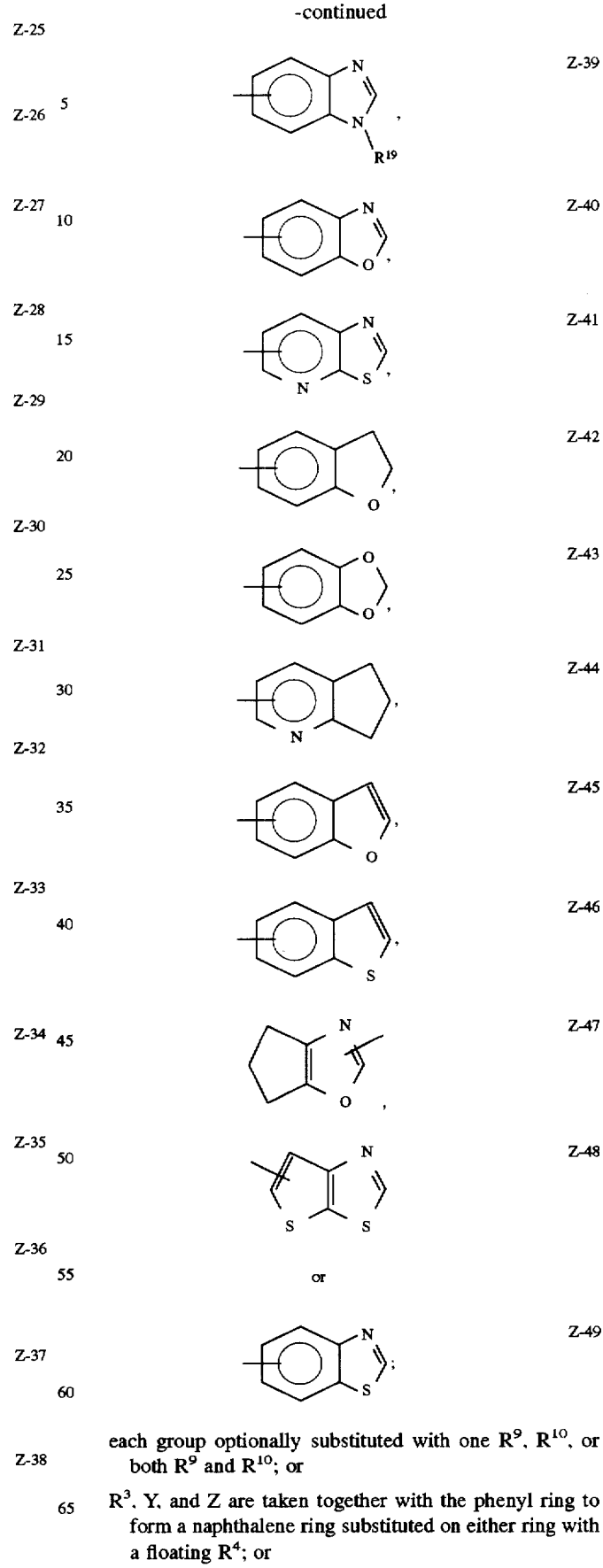
each group optionally substituted with one $R^9$, $R^{10}$, or both $R^9$ and $R^{10}$; or
$R^3$, Y, and Z are taken together with the phenyl ring to form a naphthalene ring substituted on either ring with a floating $R^4$; or Y and Z are taken together to form

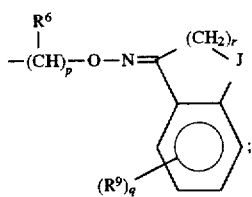

or

R$^8$ is 1–6 halogen; C$_1$–C$_6$ alkoxy; C$_1$–C$_6$ haloalkoxy; or R$^8$ is phenyl, phenoxy, pyridinyl, pyridinyloxy, pyrimidinyl, or pyrimidinyloxy each optionally substituted with one of R$^{11}$, R$^{12}$, or both R$_{11}$ and R$^{12}$;

R$^9$ is 1–2 halogen; C$_1$–C$_6$ alkyl; C$_1$–C$_6$ haloalkyl; C$_1$–C$_6$ alkoxy; C$_1$–C$_6$ haloalkoxy; C$_1$–C$_6$ alkylthio; cyano; CO$_2$(C$_1$–C$_6$ alkyl); NH(C$_1$–C$_6$ alkyl); or N(C$_1$–C$_6$ alkyl)$_2$; or R$^9$ is C$_3$–C$_6$ cycloalkyl, phenyl, phenoxy, pyridinyl, pyridinyloxy, pyrimidinyl, or pyrimidinyloxy each optionally substituted with one of R$^{11}$, R$^{12}$, or both R$^{11}$ and R$^{12}$; and R$^{19}$ is H; C$_1$–C$_6$ alkyl; C$_1$–C$_6$ haloalkyl; or phenyl optionally substituted with halogen, C$_1$–C$_4$ alkyl, C$_1$–C$_4$ haloalkyl, C$_1$–C$_4$ alkoxy, C$_1$–C$_4$ haloalkoxy, nitro or cyano.

Preferred 2. Compounds of Preferred 1 wherein:

Z is phenyl or Z-1 to Z-21, each optionally substituted with one of R$^9$, R$^{10}$, or both R$^9$ and R$^{10}$; or Y and Z are taken together to form

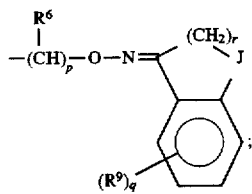

J is —CH$_2$— or —CH$_2$CH$_2$—;
p is 0; and
r is 1.

Preferred 3. Compounds of Preferred 2 wherein:

A is O; N; NR$^5$; or CR$^{14}$;
X is OR$^1$;
R$^1$ is C$_1$–C$_3$ alkyl;
R$^2$ is H or C$_1$–C$_2$ alkyl;
R$^3$ and R$^4$ are each H;
Y is —O—; —CH=CH—; —CH$_2$O—; —OCH$_2$—; —CH$_2$O —N=C(R$^7$)—; or —CH$_2$OC(=O)NH—;
R$^7$ is H; C$_1$–C$_3$ alkyl; or C$_1$–C$_3$ haloalkyl; and
Z is phenyl, pyridinyl, pyrimidinyl, or thienyl, each optionally substituted with one of R$^9$, R$^{10}$, or both R$^9$ and R$^{10}$.

Preferred 4. Compounds of Preferred 3 wherein:

A is O or NR$^5$;
G is C;
Y is —O—; —CH$_2$O —; —OCH$_2$—; or —CH$_2$O—N=C(R$^7$)—; and
R$^7$ is H; C$_1$–C$_2$ alkyl; or C$_1$–C$_2$ haloalkyl.

Preferred 5. Compounds of Preferred 3 wherein:

A is N or CR$^{14}$;
G is N;

Y is —O—; —CH$_2$O—; —OCH$_2$—; or —CH$_2$O—N=C(R$^7$)—; and
R$^7$ is H; C$_1$–C$_2$ alkyl; or C$_1$–C$_2$ haloalkyl.

Preferred 6. Compounds of Preferred 4 wherein:

R$^1$ is methyl;
R$^2$ is methyl; and
Z is phenyl optionally substituted with one of R$^9$, R$^{10}$, or both R$^9$ and R$^{10}$.

Preferred 7. Compounds of Preferred 5 wherein:

R$^1$ is methyl;
R$^2$ is methyl; and
Z is phenyl optionally substituted with one of R$^9$, R$^{10}$, or both R$^9$ and R$^{10}$.

It is recognized that some reagents and reaction conditions described below for preparing compounds of Formula I may not be compatible with some functionalities claimed for R$^1$, R$^2$, R$^3$, R$^4$, A, G, W, X, Y, and Z. In these cases, the incorporation of protection/deprotection sequences into the synthesis may be necessary in order to obtain the desired products. The cases in which protecting groups are necessary, and which protecting group to use, will be apparent to one skilled in chemical synthesis.

In the following description of the preparation of compounds of Formula I, compounds denoted as Formula Ia through Ik are various subsets of the compounds of Formula I. All substituents for compounds of Formula Ia through Ik and Formulae 1–39 are as defined above for Formula I except where indicated otherwise.

Compounds of this invention can exist as one or more stereoisomers. The various stereoisomers include enantiomers, diastereomers and geometric isomers. One skilled in the art will appreciate that one stereoisomer may be more active than the others and how to separate said stereoisomers. Accordingly, the present invention comprises mixtures, individual stereoisomers, and optically active mixtures of compounds of Formula I as well as agriculturally suitable salts thereof.

One skilled in the art will recognize that some compounds of Formula I can exist in one or more tautomeric forms. For example, a compound of Formula I wherein R$^2$ is H may exist as tautomer Ia or Ib, or both Ia and Ib. The present invention comprises all tautomeric forms of compounds of Formula I.

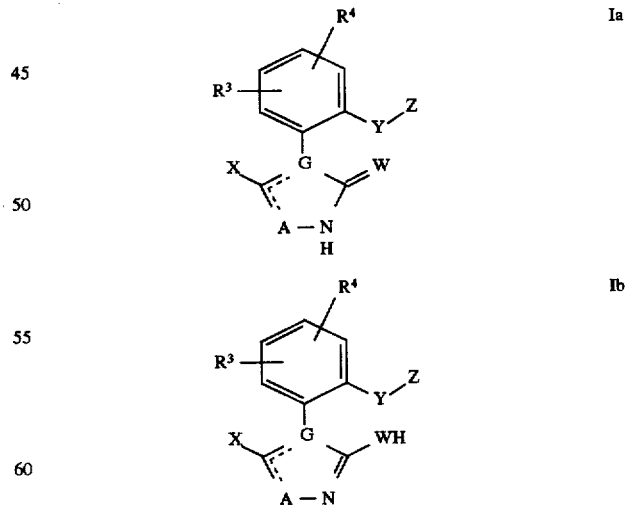

DETAILED DESCRIPTION OF THE INVENTION

The compounds of Formula I can be prepared as described below in Procedures 1) to 5). Procedures 1) to 4)

describe syntheses involving construction of the amide ring after the formation of the aryl moiety. Procedure 5) describes syntheses of the aryl moiety with the amide ring already in place.

1) Alkylation Procedures

The compounds of Formula I are prepared by treating compounds of Formula 1 with an appropriate alkyl transfer reagent in an inert solvent with or without additional acidic or basic reagents or other reagents (Scheme 1). Suitable solvents are selected from the group consisting of polar aprotic solvents such as acetonitrile, dimethylformamide or dimethylsulfoxide; ethers such as tetrahydrofuran, dimethoxyethane, or diethyl ether; ketones such as acetone or 2-butanone; hydrocarbons such as toluene or benzene; and halocarbons such as dichloromethane or chloroform.

Scheme 1

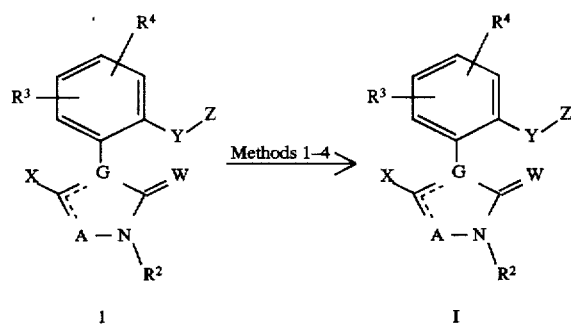

X = OH or SH       X = OR$^1$ or SR$^1$

Method 1: Q—CH=N$_2$ (Q = H or (CH$_3$)$_3$Si)
2

Method 2: $Cl_3C\underset{3}{\overset{NH}{\|}}OR^1$ ; Lewis acid

Method 3: (R$^1$)$_3$O$^+$BF$_4^-$
4

Method 4: (R$^1$)$_2$SO$_4$; R$^1$OSO$_2$Q; or R$^1$—hal;
optional base
(hal = F, Cl, Br, or I)
(Q = C$_1$–C$_6$ alkyl, C$_1$–C$_6$ haloalkyl)

For example, compounds of Formula I can be prepared by the action of diazoalkane reagents of Formula 2 such as diazomethane (Q=H) or trimethylsilyldiazomethane (Q=(CH$_3$)$_3$Si) on compounds of dicarbonyl compounds of Formula 1 (Method 1). Use of trimethylsilyldiazomethane requires a protic cosolvent such as methanol. For examples of these procedures, see *Chem. Pharm. Bull.*, (1984), 32, 3759.

As indicated in Method 2, compounds of Formula I can also be prepared by contacting carbonyl compounds of Formula 1 with alkyl trichloroacetimidates of Formula 3 and a Lewis acid catalyst. Suitable Lewis acids include trimethylsilyl triflate and tetrafluoroboric acid. The alkyl trichloroacetimidates can be prepared from the appropriate alcohol and trichloroacetonitrile as described in the literature (J. Danklmaier and H. Hönig, *Synth. Commun.*, (1990), 20, 203).

Compounds of Formula I can also be prepared from compounds of Formula 1 by treatment with a trialkyloxonium tetrafluoroborate (i.e., Meerwein's salt) of Formula 4 (Method 3). The use of trialkyloxonium salts as powerful alkylating agents is well known in the art (see U. Schöllkopf, U. Groth, C. Deng, *Angew. Chem., Int. Ed. Engl.*, (1981), 20, 798).

Other alkylating agents which can convert carbonyl compounds of Formula 1 to compounds of Formula I are dialkyl sulfates such as dimethyl sulfate, haloalkyl sulfonates such as methyl trifluoromethanesulfonate, and alky halides such as iodomethane and propargyl bromide (Method 4). These alkylations can be conducted with or without additional base. Appropriate bases include alkali metal alkoxides such as potassium tert-butoxide, inorganic bases such as sodium hydride and potassium carbonate, or tertiary amines such as triethylamine, pyridine, 1,8-diazabicyclo[5.4.0]undec-7-ene (DBU), and triethylenediamine. See R. E. Benson, T. L. Cairns, *J. Am. Chem. Soc.*, (1948), 70, 2115 for alkylation examples using agents of this type.

Compounds of Formula 1a (compounds of Formula 1 wherein G=C, W=O and X=OH) can be prepared by condensation of malonates or malonate derivatives of Formula 5 with an ambident nucleophile of Formula 6 (Scheme 2). The nucleophiles of Formula 6 are N-substituted hydroxylamines (HO—NHR$^2$) and substituted hydrazines (HN(R$^5$)—NHR$^2$). Examples of such nucleophiles are N-methylhydroxylamine and methylhydrazine. The preparation of the malonate esters of Formula 5 can be prepared by methods described hereinafter. The esters of Formula 5 can also be activated by first hydrolyzing the ester to form the corresponding carboxylic acid, and then converting the acid into the acid chloride (T=Cl) using thionyl chloride or oxalyl chloride, or into the acyl imidazole (T=1-imidazolyl) by treating with 1,1'-carbonyldiimidazole.

Scheme 2

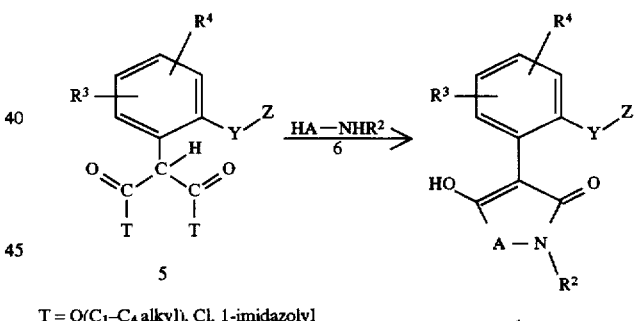

T = O(C$_1$–C$_4$ alkyl), Cl, 1-imidazolyl

Esters of Formula 5a can be prepared from copper (I)-catalyzed reaction of malonate esters of Formula 7 with substituted iodobenzenes of Formula 8 according to methods adapted from A. Osuka, T. Kobayashi and H. Suzuki, *Synthesis*, (1983), 67, and illustrated in Scheme 3.

Scheme 3

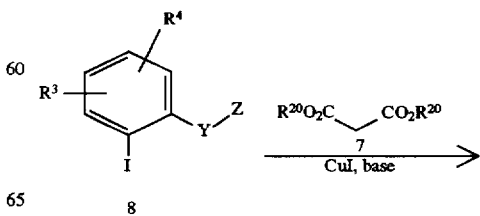

-continued
Scheme 3

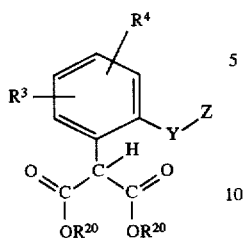

$R^{20} = C_1-C_4$ alkyl

Additionally, the malonate esters of Formula 5a can be prepared by treating phenyl acetic acid esters of Formula 9 with a dialkyl carbonate or alkyl chloroformate in the presence of a suitable base such as, but not limited to, sodium metal and sodium hydride (Scheme 4). For example, see *J. Am. Chem. Soc.*, (1928), 50, 2758.

Scheme 4

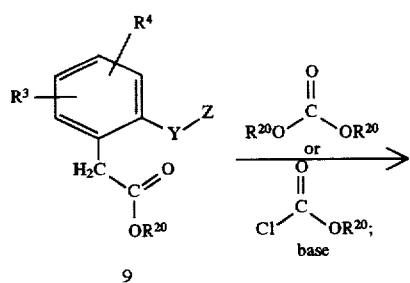

Esters of Formula 9 can be prepared from acid-catalyzed alcoholysis of phenyl acetonitriles of Formula 10 or esterification of phenyl acetic acids of Formula 11 as illustrated in Scheme 5 (see *Org. Synth.*, Coll. Vol. I, (1941), 270).

Scheme 5

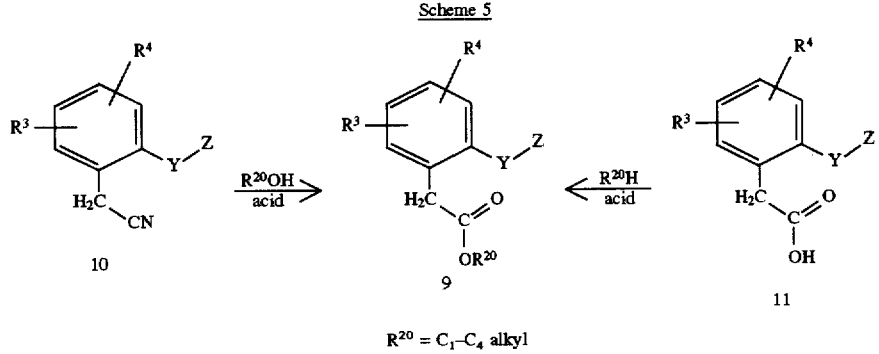

$R^{20} = C_1-C_4$ alkyl

Phenyl acetic acid esters of Formula 9a can also be prepared by copper (I)-catalyzed condensation of phenyl halides of Formula 12 with compounds of Formula 13 as described in EP-A-307,103 and illustrated below in Scheme 6.

Scheme 6

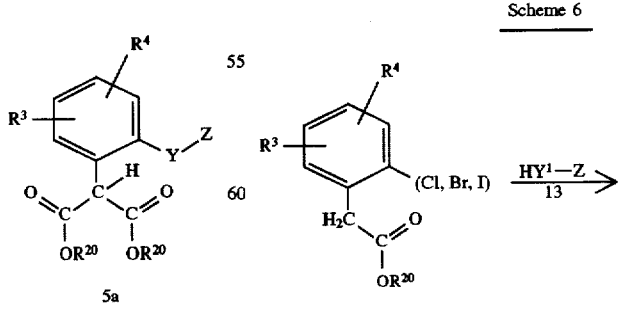

$R^{20} = C_1-C_4$ alkyl

Scheme 6
-continued

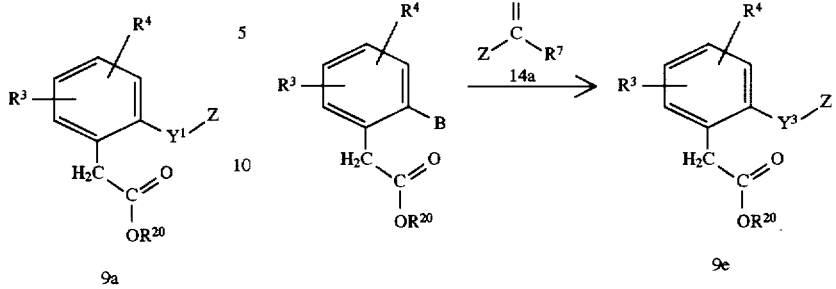

$R^{20} = C_1-C_4$ alkyl
$Y^1 = O, S, OCHR^6, SCHR^6, O-N=C(R^7)$

Some esters of Formula 9 (Formula 9b) can also be prepared by forming the $y^2$ bridge using conventional nucleophilic substitution chemistry (Scheme 7). Displacement of an appropriate leaving group (Lg) in electrophiles of Formula 15 or 16 with a nucleophilic ester of Formula 14 affords compounds of Formula 9b. A base, for example sodium hydride, is used to generate the corresponding alkoxide or thioalkoxide of the compound of Formula 14.

Scheme 7

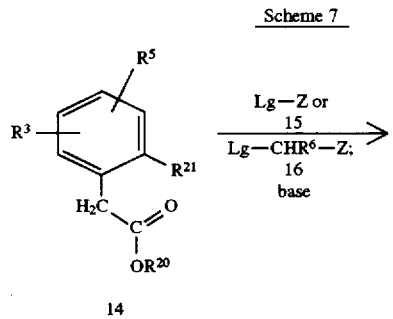

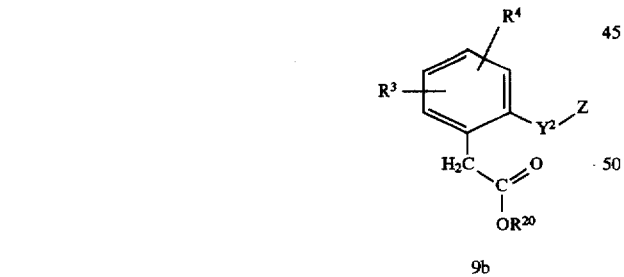

$R^{20} = C_1-C_4$ alkyl
$R^{21} = OH, SH, CHR^6OH, CHR^6SH$
$Y^2 = O, S, OCHR^6, SCHR^6, CHR^6O, CHR^6S$
Lg = Br, Cl, I, $OSO_2CH_3$, $OSO_2(4-Me-Ph)$ Some esters of Formula 9 (Formula 9e) can also be prepared by forming the $y^3$ bridge from substituted hydroxylamine 9d and carbonyl compounds 14a. The hydroxylamine 9d is in turn prepared from esters 9c. This method has been described in EP-600,835 and illustrated in Scheme 8.

Scheme 8

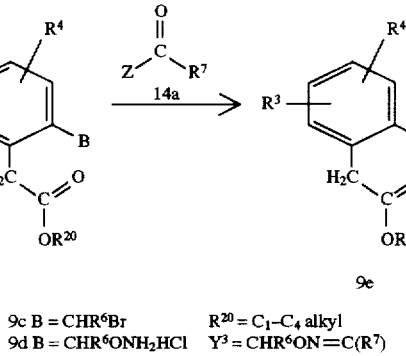

9c B = CHR$^6$Br $\quad$ R$^{20}$ = C$_1$-C$_4$ alkyl
9d B = CHR$^6$ONH$_2$HCl $\quad$ Y$^3$ = CHR$^6$ON=C(R$^7$)

2) Displacement and Conjugate Addition/Elimination Procedures

Compounds of Formula I can also be prepared by reaction of Formula 17 compounds with alkali metal alkoxides ($R^1O^-M^+$) or alkali metal thioalkoxides ($R^1S^-M^+$) in a suitable solvent (Scheme 9). The leaving group $Lg^1$ in the amides of Formula 17 are any group known in the art to undergo a displacement reaction of this type. Examples of suitable leaving groups include chlorine, bromine, and sulfonyl and sulfonate groups. Examples of suitable inert solvents are dimethylformamide or dimethylsulfoxide.

Scheme 9

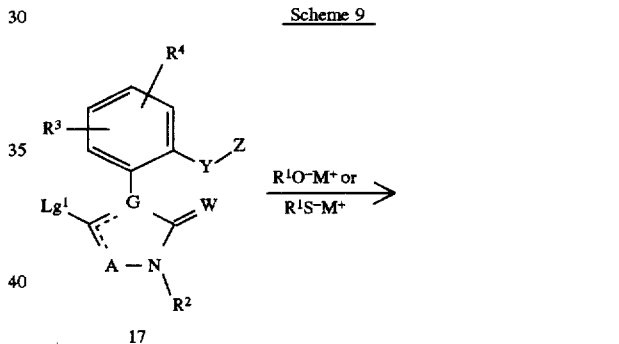

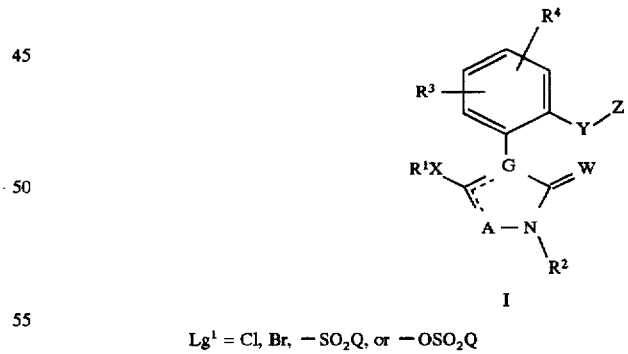

$Lg^1 = Cl, Br, -SO_2Q,$ or $-OSO_2Q$
$Q = C_1-C_6$ alkyl or $C_1-C_6$ haloalkyl
M = K or Na Compounds of Formula 17a can be prepared from compounds of Formula 1b (compounds of Formula 1 wherein X is OH) by reaction with halogenating agents such as thionyl chloride or phosphorus oxybromide to form the corresponding β-halo-substituted derivatives (Scheme 10). Alternatively, compounds of Formula 1b can be treated with an alkylsulfonyl halide or haloalkylsulfonyl anhydride, such as methane sulfonyl chloride, p-toluenesulfonyl chloride, and trifluoromethanesulfonyl anhydride, to form the corresponding β-alkylsulfonate of Formula 17a. The reaction with the sulfonyl halides may be performed in the presence of a suitable base (e.g., triethylamine).

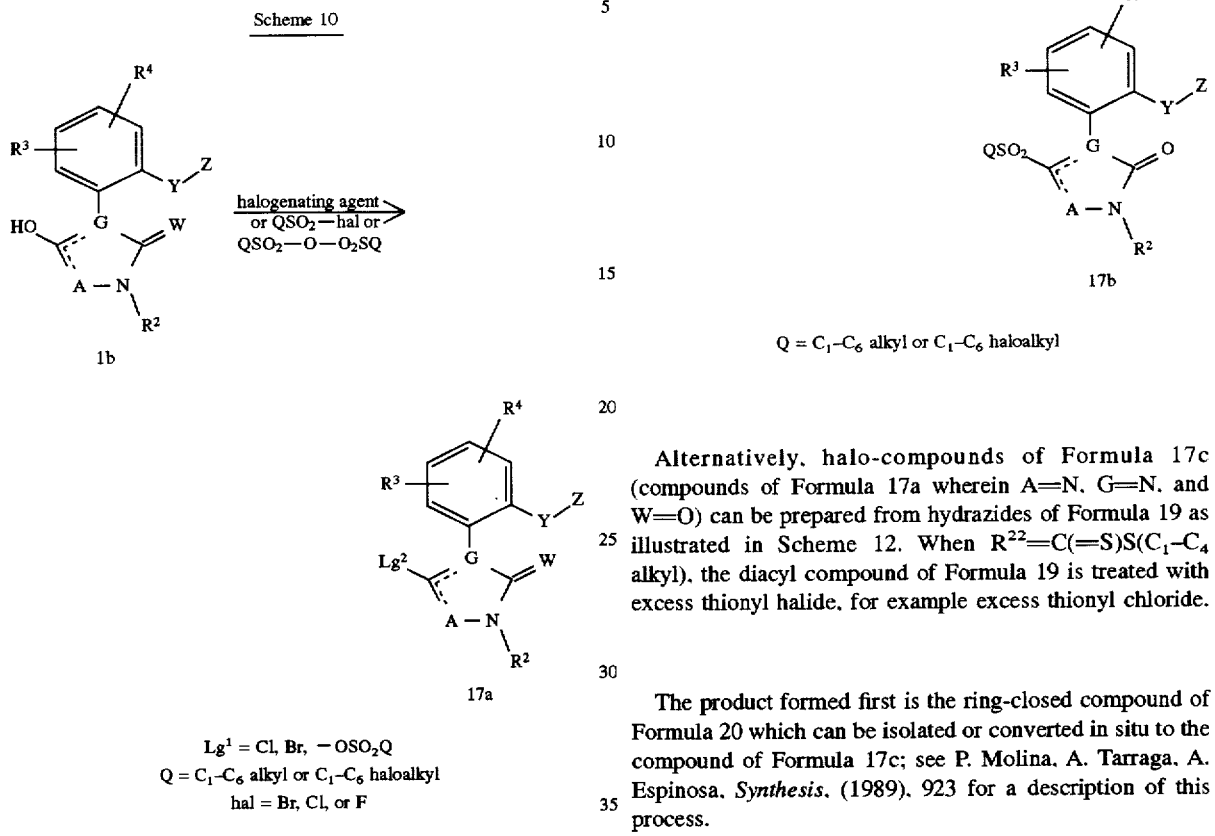

As illustrated in Scheme 11, sulfonyl compounds of Formula 17b can be prepared by oxidation of the corresponding thio compound of Formula 18 using well-known methods for the oxidation of sulfur (see Schrenk. K. In *The Chemistry of Sulphones and Sulphoxides*; Patai. S. et al., Eds.; Wiley: New York, 1988). Suitable oxidizing reagents include meta-chloro-peroxybenzoic acid, hydrogen peroxide and Oxone® ($KHSO_5$).

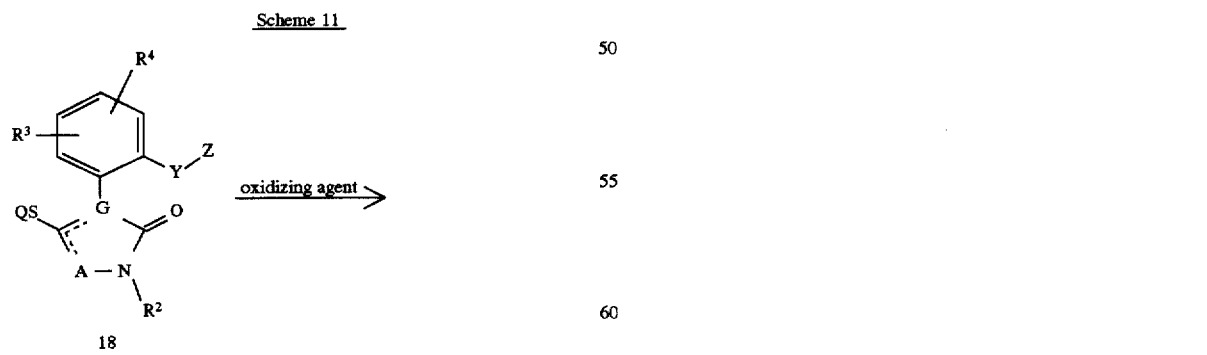

Alternatively, halo-compounds of Formula 17c (compounds of Formula 17a wherein A=N, G=N, and W=O) can be prepared from hydrazides of Formula 19 as illustrated in Scheme 12. When $R^{22}$=C(=S)S($C_1$–$C_4$ alkyl), the diacyl compound of Formula 19 is treated with excess thionyl halide, for example excess thionyl chloride.

The product formed first is the ring-closed compound of Formula 20 which can be isolated or converted in situ to the compound of Formula 17c; see P. Molina, A. Tarraga, A. Espinosa, *Synthesis*, (1989), 923 for a description of this process.

Alternatively, when $R^{22}$=$R^2$ as defined above, the hydrazide of Formula 19 is cyclized with phosgene to form the cyclic urea of Formula 17c wherein hal =Cl. This procedure is described in detail in *J. Org. Chem.*, (1989), 54, 1048.

Scheme 12

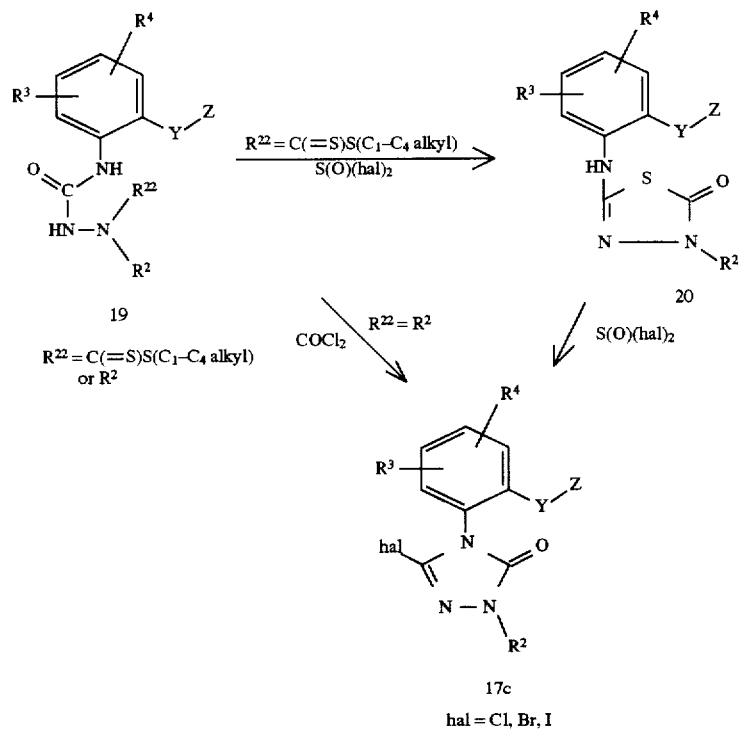

hal = Cl, Br, I

The hydrazides of Formula 19 can be prepared as illustrated in Scheme 13. Condensation of the isocyanate of Formula 21 with the hydrazine of Formula $H_2NNR^2R^{22}$ in an inert solvent such as tetrahydrofuran affords the hydrazide.

Scheme 13

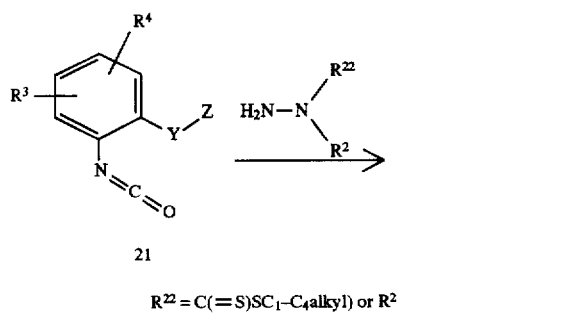

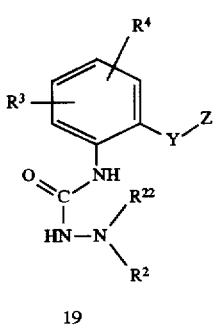

3) Conjugate Addition/Cyclization Procedures

In addition to the methods disclosed above, compounds of Formula I wherein $X=SR^1$ and $G=C$ (Formula Ic) can be prepared by treating a ketenedithioacetal of Formula 22 with an ambident nucleophile of Formula 6 (Scheme 14). The nucleophiles of Formula 6 are described above.

Scheme 14

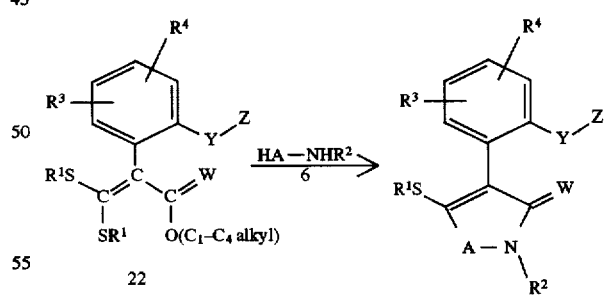

Ketene dithioacetals of Formula 22a can be prepared by condensing phenyl acetic acid esters of Formula 9 with carbon disulfide in the presence of a suitable base, followed by reaction with two equivalents of an $R^1$-halide, such as iodomethane or propargyl bromide (Scheme 15).

Scheme 15

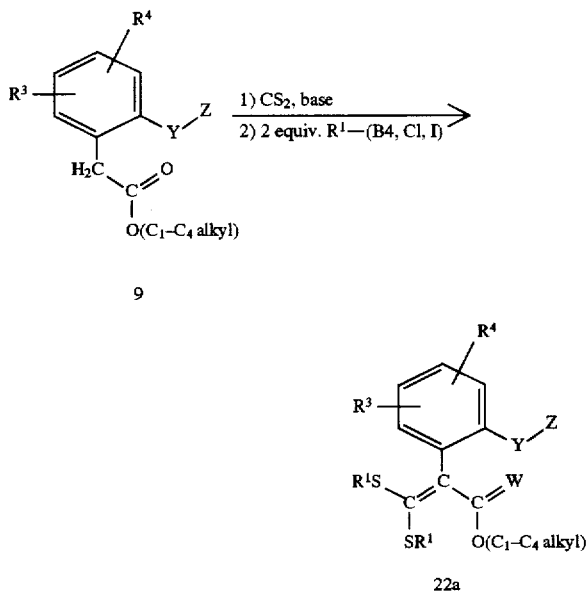

Compounds of Formula 1a (compounds of Formula 1 wherein A=N, G=N) can be prepared by condensation of N-amino-ureas of Formula 23 with a carbonylating agent of Formula 24 (Scheme 16). The carbonylating agents of Formula 24 are carbonyl or thiocarbonyl transfer reagents such as phosgene, thiophosgene, diphosgene (ClC(=O)OCCl$_3$), triphosgene (Cl$_3$COC(=O)OCCl$_3$), N,N'-carbonyldiimidazole, N,N'-thiocarbonyldiimidazole, and 1,1'-carbonyldi(1,2,4-triazole). Alternatively, the compounds of Formula 24 can be alkyl chloroformates or dialkyl carbonates. Some of these carbonylating reactions may require the addition of a base to effect reaction. Appropriate bases include alkali metal alkoxides such as potassium tert-butoxide, inorganic bases such as sodium hydride and potassium carbonate, or tertiary amines such as triethylamine, pyridine, 1,8-diazabicyclo[5.4.0]undec-7-ene (DBU), or triethylenediamine. Suitable solvents include polar aprotic solvents such as acetonitrile, dimethylformamide, or dimethylsulfoxide; ethers such as tetrahydrofuran, dimethoxyethane, or diethyl ether; ketones such as acetone or 2-butanone; hydrocarbons such as toluene or benzene; or halocarbons such as dichloromethane or chloroform. The reaction temperature can vary between 0° C. and 150° C. and the reaction time can be from 1 to 72 hours depending on the choice of base, solvent, temperature, and substrates.

Scheme 16

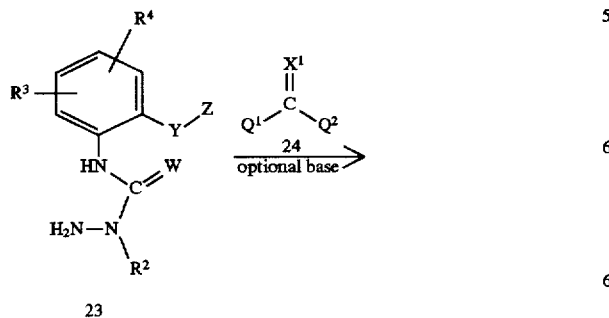

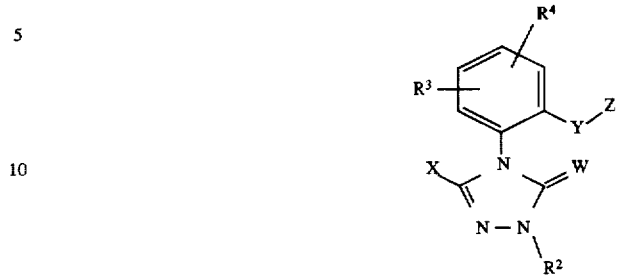

$Q^1$ and $Q^2$ are independently Cl, OCCl$_3$, O(C$_1$-C$_4$ alkyl), 1-imidazolyl, 1,2,4-triazolyl
X = OH or SH
$X^1$ = O or S N-Amino-ureas of Formula 23 can be prepared as illustrated in Scheme 17. Treatment of an aniline of Formula 25 with phosgene, thiophosgene, N,N'-carbonyldiimidazole, or N,N'-thiocarbonyldiimidazole produces the isocyanate or isothiocyanate of Formula 26. A base can be added for reactions with phosgene or thiophosgene. Subsequent treatment of the iso(thio)cyanate with an R$^2$-substituted hydrazine produces the N-amino-urea of Formula 23.

Scheme 17

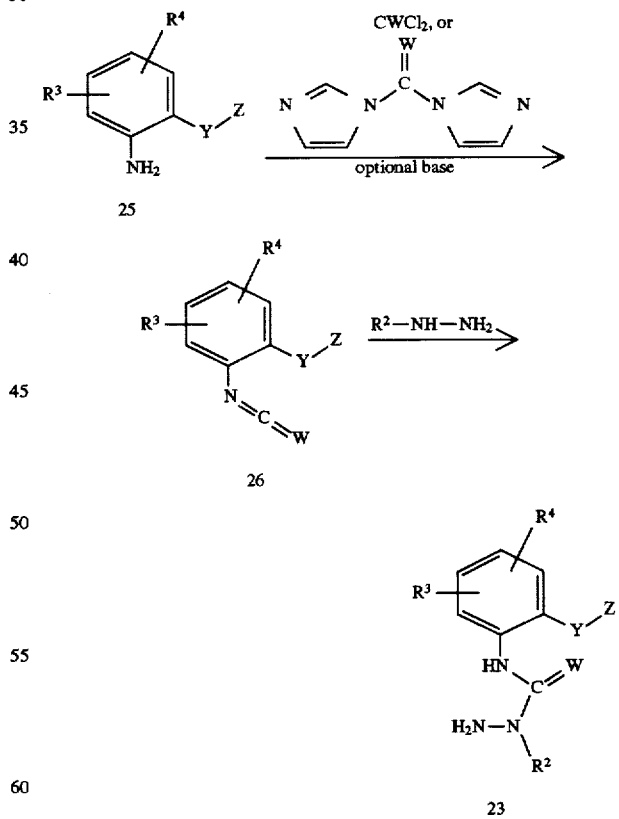

Compounds of Formula 1b (compounds of Formula 1 wherein A=CR$^5$, G=N, and X=O) can be prepared by either method illustrated in Scheme 18. Ureas of Formula 27 are reacted with activated 2-halocarboxylic acid derivatives such as 2-halocarboxylic acid chlorides, 2-halocarboxylic acid esters or 2-haloacyl imidazoles. The initial acylation on the aniline nitrogen is followed by an intramolecular displacement of the 2-halo group to effect cyclization. Base may be added to accelerate the acylation and/or the subsequent cyclization. Suitable bases include triethylamine and sodium hydride. Alternatively, Formula 1b compounds can be prepared by reaction of Formula 26 isocyanates with Formula 28a esters. As described above, base may be added to accelerate the reaction and subsequent cyclization to Formula 1b compounds.

Scheme 18

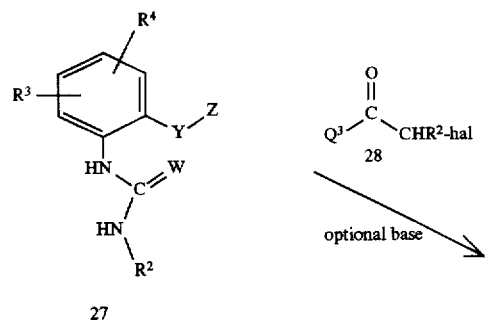

$Q^3$ = Cl, O($C_1$-$C_4$ alkyl), or 1-imidazolyl
hal = Cl, Br, or I

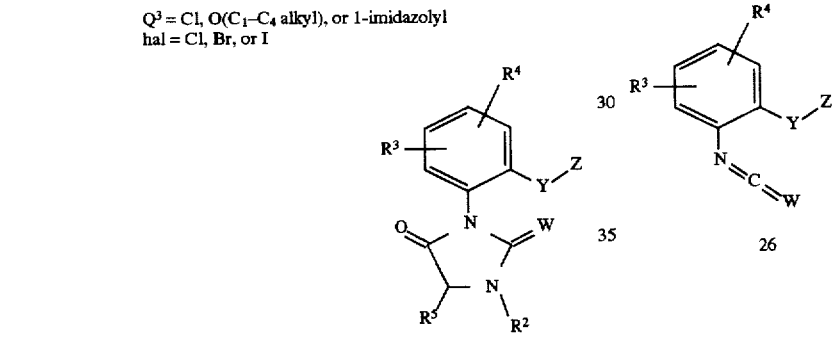

The ureas of Formula 27 can be prepared by either of the methods illustrated in Scheme 19. The anilines of Formula 25 can be contacted with an isocyanate or isothiocyanate of Formula $R^2N=C=W$ as described above. Alternatively, an isocyanate or isothiocyanate of Formula 26 can be condensed with an amine of Formula $R^2$—$NH_2$ to form the urea. The anilines and iso(thio)cyanates of Formulae 25 and 26, respectively, are commercially available or prepared by well-known methods. For example, isothiocyanates can be prepared by methods described in J. Heterocycl. Chem., (1990), 27, 407. Isocyanates can be prepared as described in March, J. Advanced Organic Chemistry; 3rd ed., John Wiley: New York, (1985), pp 944, 1166.

Scheme 19

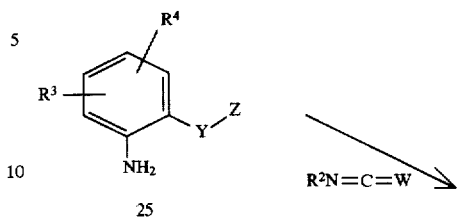

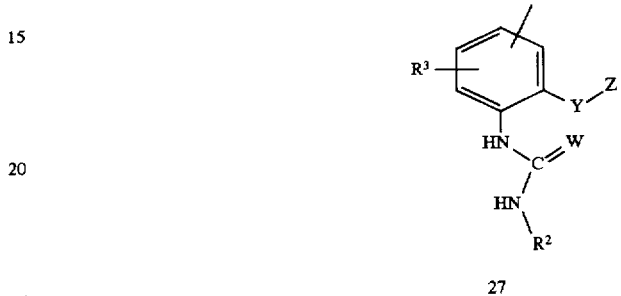

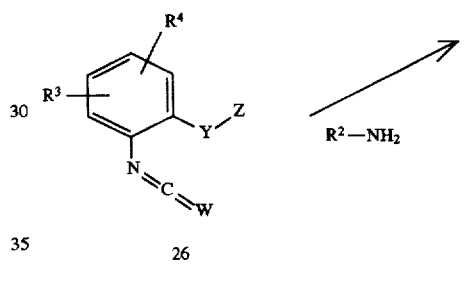

4) Thionation Procedures

Compounds of Formula Ie, compounds of Formula I wherein W=S, can be prepared by treating compounds of Formula Id (I wherein W=O) with thionating reagents such as $P_2S_5$ or Lawesson's reagent [2,4-bis(4-methoxyphenyl)-1,3-dithia-2,4-diphosphetane-2,4-disulfide] as illustrated in Scheme 20 (see Bull. Soc. Chim. Belg., (1978), 87, 229; and Tetrahedron Lett., (1983), 24, 3815).

Scheme 20

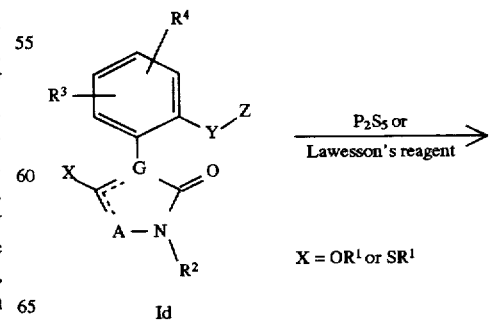

X = $OR^1$ or $SR^1$

-continued
Scheme 20

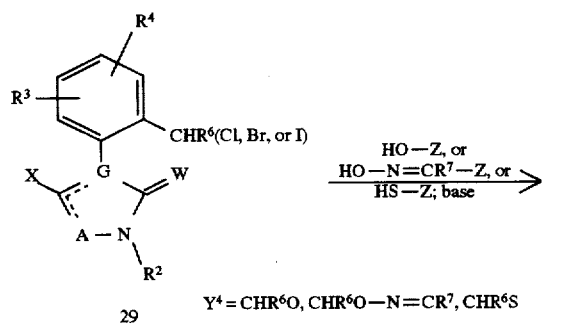

If

5) Aryl Moiety Synthesis Procedures

Compounds of Formula If (compounds of Formula I wherein Y is $CHR^6O$, $CHR^6S$, or $CHR^6O$ —$N=CR^7$) can be prepared by contacting benzyl halides of Formula 29 with various nucleophiles (Scheme 21). The appropriate alcohol or thiol is treated with a base, for example sodium hydride, to form the corresponding alkoxide or thioalkoxide which acts as the nucleophile.

Benzyl halides of Formula 29 can be prepared by radical halogenation of the corresponding alkyl compound (i.e., H instead of halogen in Formula 29), or by acidic cleavage of the corresponding methylether (i.e., OMe instead of halogen in Formula 29).

Compounds of Formula I wherein Y is $CR^6=CR^6$ and $CHR^6$—$CHR^6$ (Formula Ig and Ih, respectively) can be prepared as illustrated in Scheme 22. Treatment of the benzyl halides of Formula 29 with triphenylphosphine or a trialkylphosphite produces the corresponding phosphonium salt (Formula 30) or phosphonate (Formula 3 1), respectively. Condensation of the phosphorus compound with a base and a carbonyl compound of Formula $Z(R^6)C=O$ affords the olefin of Formula Ig.

Scheme 22

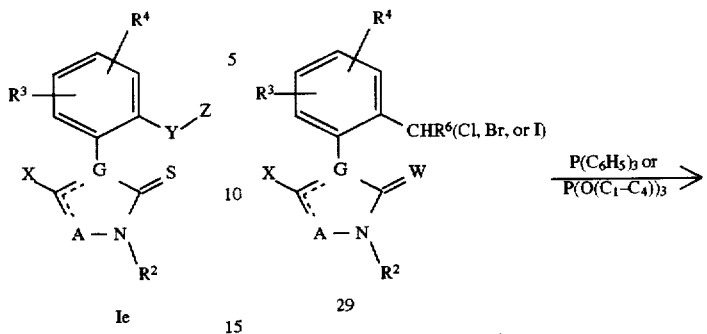

30: $P^1 = P^+(C_6H_5)_3$halide$^-$

31: $P^1 = P(O(C_1-C_4))_2$

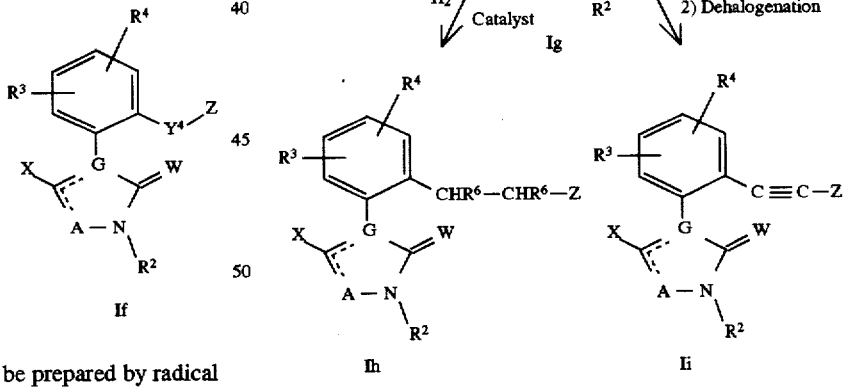

The olefins of Formula Ig can be converted to the saturated compounds of Formula Ih by hydrogenation over a metal catalyst such palladium on carbon as is well-known in the art (Rylander, *Catalytic Hydrogenation in Organic Synthesis*; Academic: New York, 1979).

Formula Ii alkynes can be prepared by halogenation/dehalogenation of Formula Ig olefins using procedures well-known in the art (March, *J. Advanced Organic Chemistry*; 3rd ed., John Wiley: New York, (1985), p 924). Additionally, Formula Ii alkynes can be prepared by well-known reaction of aromatic halides with alkyne derivatives in the presence of catalysts such as nickel or palladium (see *J. Organomet. Chem.*, (1975), 93 253–257).

The olefin of Formula Ig can also be prepared by reversing the reactivity of the reactants in the Wittig or Homer-Emmons condensation. For example, 2-alkylphenyl derivatives of Formula 31 can be converted into the corresponding dibromo-compound of Formula 33 as illustrated in Scheme 23 (see *Synthesis*, (1988), 330). The dibromo-compound can be hydrolyzed to the carbonyl compound of Formula 34, which in turn can be condensed with a phosphorus-containing nucleophile of Formula 35 or 36 to afford the olefin of Formula Ig.

Scheme 23

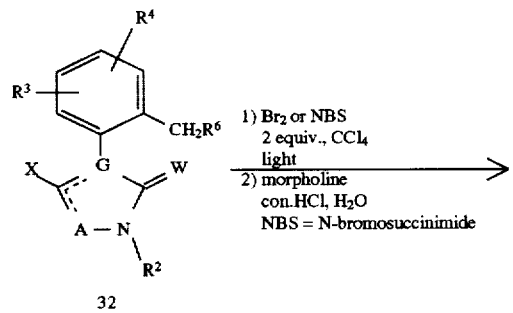

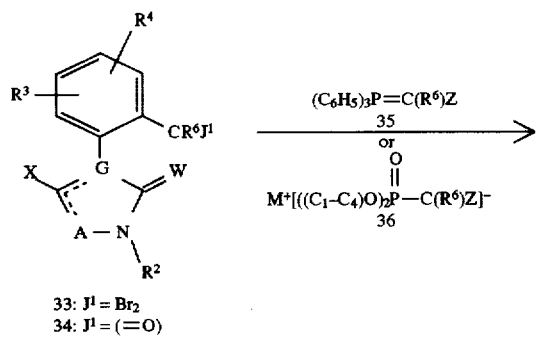

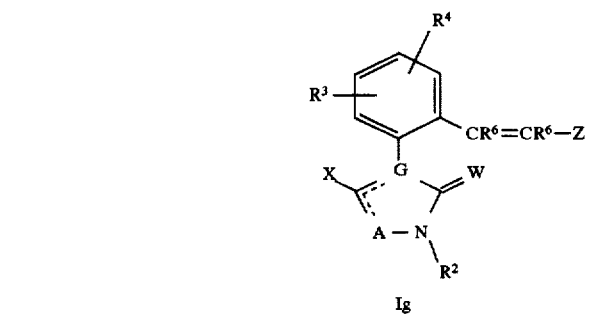

Oximes of Formula Ij (Formula I wherein Y is $C(R^7)$=N—O) can be prepared from carbonyl compounds of Formula 37 by condensation with hydroxylamine, followed by O-alkylation with electrophiles of Formula Z-(Cl, Br, or I) (Scheme 24). Alternatively, the O-substituted hydroxylamine can be condensed with the carbonyl compound of Formula 37 to yield oximes of Formula Ij directly.

Scheme 24

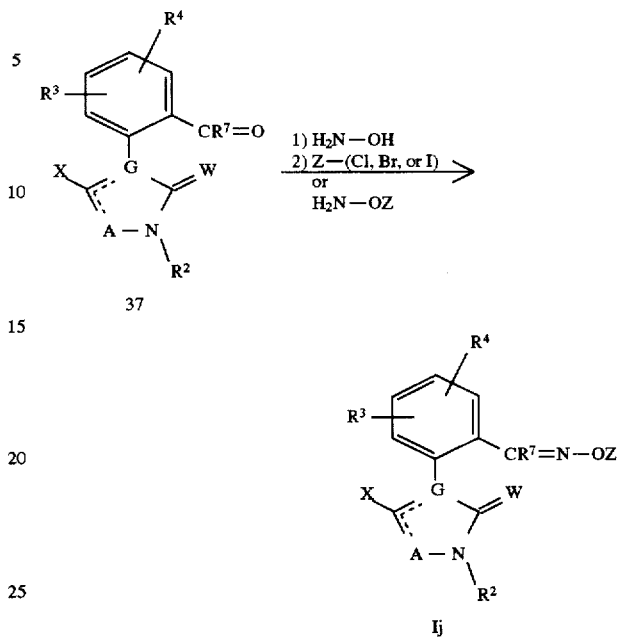

Carbamates of Formula Ik can be prepared by reacting benzyl alcohols of Formula 38 with isocyanates of Formula 39 (Scheme 25). A base such as triethylamine can be added to catalyze the reaction.

Scheme 25

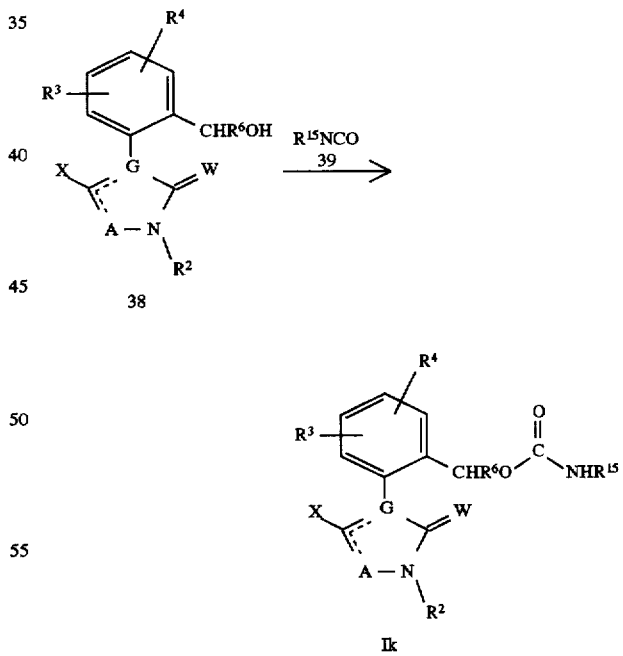

The following Examples are representative of the production of the novel cyclic amides of Formula I. $^1$H NMR Spectra are reported in ppm downfield from tetramethylsilane; s=singlet, d=doublet, t=triplet, dt=doublet of triplets, td=triplet of doublets, m=multiplet.

EXAMPLE 1

Step A: Preparation of Methyl 2-(3-methoxyphenoxy) phenylacetate (2-Chlorophenyl)acetic acid (60 g), 3-methoxyphenol (87 g), potassium carbonate (97.2 g) and copper (I) chloride (0.6 g) were combined and mechanically stirred to give a thick brown suspension. The suspension was heated for 4.5 h, then cooled to 70° C. and 10 mL of N,N-dimethylformamide was added. The mixture was poured into ice water and acidified with concentrated aqueous HCl. The mixture was extracted with diethyl ether and the combined extracts were washed with water (4 times) dried (MgSO$_4$), filtered and concentrated under reduced pressure to provide 122 g of an oil. The crude material was dissolved in 73 mL of methanol and then 2.1 mL of concentrated sulfuric acid was added. The mixture was heated at reflux for 4 h. The mixture was poured into ice water and extracted with diethyl ether. The combined organic phases were washed with 10% aqueous NaOH solution (2 times), then water (4 times), then brine. The organic phase was dried (MgSO4), filtered and concentrated under reduced pressure to yield 46.4 g (48%) of the title material of Step A as a reddish oil. $^1$H NMR (CDCl$_3$): δ6.45 –7.4 (m,8H), 3.76 (s,3H), 3.69 (s,2H), 3.62 (s,3H).

Step B: Preparation of Dimethyl [2-(3-methoxyphenoxy) phenyl]propanedioate

Methyl 2-(3-methoxyphenoxy)phenylacetate (6.81 g) was dissolved in 11 mL of dimethyl carbonate and 600 mg of sodium was added. The mixture was heated at reflux for 10 h, then cooled. The reaction mixture was quenched with water, acidified with concentrated aqueous HCl and extracted with dichloromethane. The combined organic extracts were dried (MgSO$_4$), filtered and concentrated under reduced pressure to give an oil. The desired material was separated from unreacted starting material by flash chromatography (4:1 hexane: ethyl acetate as eluant) to yield after concentration, 3.54 g (43%) of the title compound of Step B. $^1$H NMR (CDCl$_3$): δ7.46(dd,J=1.5,7.5Hz,1H), 7.29 (t,J=8Hz,1H), 7.2 (m,2H), 6.92 (d,J=8Hz,1H), 6.65 (td, J=1.5,7.5Hz,1H), 6.5 (m,2H), 5.14 (s,1H), 3.77 (s,3H), 3.73 (s,6H).

Step C: Preparation of 5-Hydroxy-4-[2-(3-methoxyphenoxy)phenyl]-2-methyl-3(2H)-isoxazolone N-Methylhydroxylamine hydrochloride (2.79 g) was dissolved in 20 mL of methanol at reflux. The solution was cooled and treated with a solution of 3.76 g potassium hydroxide in 15 mL of methanol. The precipitated potassium chloride was removed by filtration and a solution of 3.54 g of dimethyl [2-(3-methoxyphenoxy)-phenyl]propanedioate in 25 mL of methanol was added dropwise. The mixture was stirred at room temperature overnight. The reaction mixture was concentrated under vacuum to a volume of about 30 mL and acidified with concentrated aqueous HCl, with cooling. The solvents were removed under reduced pressure and the residue was partitioned between water and dichloromethane. The combined organic phases were dried (MgSO$_4$), filtered and concentrated under reduced pressure to yield 2.95 g (88%) of the title compound of Step C. $^1$H NMR (CDCl$_3$): δ7.2 –7.4 (m,3H), 7.12 (dt,J=1,7.5Hz,1H), 6.81 (d,J=8.5Hz,1H), 6.72 (d,J=8Hz,1H), 6.6 (m,2H), 4.43(s, 1H), 3.77 (s,3H), 3.28 (s,3H).

Step D: Preparation of 5-Methoxy-4-[2-(3-methoxyphenoxy)phenyl]-2-methyl-3(2H)-isoxazolone 5-Hydroxy-4-[2-(3-methoxyphenoxy)phenyl]-2-methyl-3 (2H)-isoxazolone (2.5 g) was dissolved in 3 mL of methanol and 15 mL of toluene and cooled in an icebath. Trimethylsilyldiazomethane (5 mL of a 2.0M solution in hexane) was added dropwise. Gas evolution was observed. The resulting yellow solution was stirred at room temperature overnight. The solvents were removed under reduced pressure and the residue was purified by flash chromatography (1:1 hexane-:ethyl acetate as eluant). The second eluting component was collected to yield 950 mg (36%) of the title compound of Step D. $^1$H NMR (CDCl$_3$): δ7.51 (dd,J=1.7, 7.5Hz,1H), 7.27 (dt,J=1.7, 7.5Hz,1H), 7.17 (m,2H), 6.97 (dd,J=1, 8Hz,1H), 6.5 (m,3H), 3.92 (s,3H), 3.74 (s,3H), 3.33(s,3H).

EXAMPLE 2

Step A: Preparation of 1-(Bromomethyl)-2-iodobenzene

To a solution of 2-iodobenzyl alcohol (50 g) in diethyl ether (500 mL), cooled in an ice-water bath, was added dropwise phosphorus tribromide (28 mL). The reaction mixture was chilled in a refrigerator for 3.5 h, then quenched by slow addition of methanol (50 mL). The mixture was washed with water, then saturated sodium bicarbonate, then water (100 mL each). The organic phase was dried (MgSO$_4$), filtered and concentrated under reduced pressure to a white solid, which was triturated in hexane and collected by filtration to yield 58 g (91%) of the title material of Step A as a solid, mp 55°–57° C.

Step B: Preparation of 1-Iodo-2-[(2-methylphenoxy)methyl] benzene

Sodium hydride (60% oil dispersion) (7.8 g) was added portionwise to a ice-water cooled solution of o-cresol (21.1 g) in tetrahydrofuran (500 mL). The mixture was stirred 20 minutes and then 1-(bromomethyl)-2-iodobenzene (58 g) was added. The mixture was warmed to 60° C. for 16 h. Additional sodium hydride (2 g) was added and the reaction mixture heated for an additional 3 h. The reaction mixture was cooled and carefully quenched with water and extracted with ethyl acetate (2×250 mL). The combined organic extracts were dried (Mg SO$_4$), filtered and concentrated under reduced pressure to an oil, which was triturated with cold hexane to provide a solid which was collected by filtration to yield 59.1 g (94%) of the title compound of Step B as a white solid, mp 106°–108° C.

Step C: Preparation of Dimethyl [2-[(2-methylphenoxy) methyl]phenyl]popanedioate To a suspension of sodium hydride (60% oil dispersion) (15.4 g) in 90 mL of 1,3-dimethyl-3,4,5,6-tetrahydro-2 [1H] -pyrimidinone (DMPU), cooled in an ice-water bath, was added dropwise a solution of dimethyl malonate (44 mL) in DMPU (150 mL). The mixture was stirred 20 minutes after the addition was completed, and then 1-iodo-2-[(2-methylphenoxy)methyl]benzene (62.5 g) and cuprous iodide (73.3 g) were added. The resulting mixture was stirred at 100° C. for 5 h, then stirred at 25° C. overnight. The mixture was diluted with 1 N. HCl (~150 mL) and extracted with diethyl ether (3 ×400 mL). The combined organic extracts were dried (Mg SO$_4$), filtered and concentrated under reduced pressure to a semi-solid, which was purified by flash chromatography on silica gel (5:2 hexane: ethyl acetate as eluant). The major material was collected and concentrated to a white solid, which was triturated in hexane and collected by filtration to yield 56.9 g (79%) of the title compound of Step C as a white solid, mp 99°–103° C.

Step D: Preparation of 5-Hydroxy-4-[2-[(2-methylphenoxy) methyl]phenyl]-3(2H)-isoxazolone To a solution of N-methylhydroxylamine hydrochloride (34.7 g) in methanol (120 mL), cooled in an ice-water bath, was added dropwise a solution of potassium hydroxide (46.6 g) in methanol (80 mL). After the addition was complete, the mixture was stirred 10 minutes. The potassium chloride precipitate was removed by filtration and a solution of dimethyl [2-[(2-methylphenoxy)methyl]phenyl] propanedioate (44 g) in 100 mL of methanol was added to the N-methyl-hydroxylamine solution. The mixture was stirred for 3 days and then cooled in an ice-water bath. Concentrated HCl (15 mL) was added and the solid was removed by filtration. The solvent was removed under vacuum and the residue diluted with ~100 mL of water and then extracted with dichloromethane (3×150 mL), then ethyl acetate (3×100 mL). The combined organic extracts were dried (Mg SO$_4$), filtered and concentrated under reduced pressure to yield 31.3 g (75%) of the title compound of Step D as a semi-solid. $^1$H NMR (DMSO-d$_6$): δ7.4 (m,2H), 7.15 (m,2H), 7.10 (m,2H), 6.8 (m,2H), 5.16 (s,2H), 2.9 (s,3H), 2.23 (s,3H).

Step E: Preparation of 5-Methoxy-2-methyl-4-[2-[(2-methylphenoxy)methyl]phenyl]-3(2H)-isoxazolone 5-Hydroxy-4-[2-[(2-methylphenoxy)methyl]phenyl]-3-(2H)-isoxazolone (31.3 g) was dissolved in 330 mL of 10:1 toluene:methanol and cooled in an ice-water bath. Trimethylsilyl-diazomethane (~2M in hexane) (55 mL) was added dropwise. Gas evolution was observed. The yellow solution was stirred at 25° C. for 2 h. The solution was diluted with 100 mL of water and extracted with ethyl acetate (4×100 mL). The combined organic extracts were dried (Mg SO$_4$), filtered and concentrated under reduced pressure to yield an oil, which was purified by flash chromatography (silica gel; 1:1 hexane:ethyl acetate as eluant). The second eluting component was collected to yield 4.35 g (13%) of the title compound of Step E as a white solid, mp 90°–92° C. $^1$H NMR (CDCl$_3$) δ7.61(d,1H), 7.35(m,3H), 7.12(m,2H), 6.84(m,2H), 5.12(s,2H), 3.96(s,3H), 3.41(s, 3H), 2.24(s, 3H).

EXAMPLE 3

Step A Preparation of 1-Methyl-N-(2-phenoxphenyl) hydrazinecarboxamide

2-Phenoxyaniline (5.57 g) and triethylamine (4.2 mL) were dissolved in 100 mL of 1,2-dichloroethane. Triphosgene (Cl$_3$COC(=O)OCCl$_3$, 2.97 g) was added and a precipitate formed. The mixture was heated to reflux and the solid redissolved. After 5.5 h, the solution was cooled and 1.6 mL of methyl hydrazine was added and a new precipitate formed. The mixture was stirred at room temperature overnight. The solvent was removed and the residue was partitioned between ethyl acetate and 1N aqueous HCl solution. The organic phases were dried (MgSO$_4$), filtered, and concentrated under reduced pressure. The residue was purified by flash chromatography (1:1 hexane: ethyl acetate as eluant). The second-least polar component was collected, the eluant was removed under reduced pressure, and the residue was triturated with hexane to afford 3.86 g (50%) of the title compound of Step A. m.p. 117°–119° C.

Step B Preparation of 2-Methyl-4-(2-phenoxyphenyl)-5-thioxo-1,2,4-triazolidin-3-one A solution of 1.54 g of 1-methyl-N-(2-phenoxyphenyl) hydrazinecarboxamide in 50 mL of tetrahydrofuran, cooled in an ice bath, was treated with 0.46 mL of thiophosgene, and then 1.68 mL of triethylamine. A precipitate formed and the mixture was stirred at ambient temperature overnight. The precipitate was removed by filtration and washed with tetrahydrofuran. The combined filtrate and washings were concentrated under reduced pressure to afford 1.8 g of an amber glassy oil. The crude material was used in the next step without further purification. $^1$H NMR (CDCl$_3$): δ6.8–7.4 (m, 9H), 3.57 (s,3H).

Step C Preparation of 2,4-Dihydro-2-methyl-5-(methylthio)-4-(2-phenoxyphenyl)-3H-1,2,4-triazol-3-one A solution of 900 mg of crude 2-methyl-4-(2-phenoxyphenyl)-5-thioxo-1,2,4-triazolidin-3-one in 50 mL of tetrahydrofuran was treated with 150 mg of sodium hydride (60% oil dispersion). After 5 minutes, 0.5 mL of iodomethane was added, and the mixture was stirred at ambient temperature overnight. The solid was removed by filtration and the filtrate concentrated to an oil. The oil was partitioned between ether and 1N hydrochloric acid solution. The organic phases were dried (MgSO$_4$), filtered and concentrated under reduced pressure. The residue was triturated in hexane/n-butyl chloride to afford 530 mg (56%) of the title compound of Step C. m.p. 129°–130° C.

EXAMPLE 4

Step A: Preparation of 2,2-Dimethyl-N-(2-methylphenyl) hydrazine carboxamide o-Tolyl isocyanate (10.0 g) was dissolved in 75 mL toluene under N$_2$. The solution was cooled to 5° C. and to this was slowly added a solution in toluene of 1,1-dimethylhydrazine (5.7 mL). After addition, the ice-bath was removed and the resulting slurry allowed to stir an additional 10 minutes. The solid was filtered off rinsing successively with hexane, a small amount of 20% diethylether/hexane, then hexanes again. This afforded 11.1 g (77%) of the title compound of Step A. $^1$H NMR (CDCl$_3$) δ8.1 (bs,1H), 7.94 (d,1H), 7.21–7.15 (m,3H), 6.99 (t,1H), 5.23 (bs,1H), 2.63 (s,6H) 2.27 (s,3H).

Step B: Preparation of 5-Chloro 2,4-dihydro-2-methyl-4-(2-methylphenyl)-3H-1,2,4triazol-3-one To a solution of 11.1 g 2,2-dimethyl-N-(2-methylphenyl) hydrazine carboxamide dissolved in 600 mL methylene chloride under N$_2$ was added 17.1 g triphosgene. The solution was heated at refulx overnight, cooled, then concentrated under reduced pressure. The resulting residue was dissolved in ethyl acetate and washed with water, then saturated aqueous NaCl. The organic phase was dried (MgSO$_4$), filtered, and concentrated under reduced pressure. The residue was purified by flash chromatography (30 –50% ethyl acetate/hexanes as eluent) to afford 8.25 g (64%) of the title compound of Step B. $^1$H NMR (CDCl$_3$) δ7.42 –7.30 (m,3H), 7.17 (d,1H), 3.54 (s,3H), 2.22 (s,3H).

Step C: Preparation of 2,4-Dihydro-5-methoxy-2-methy-4-(2-methylphenyl)-3H-1,2,4-triazol-3-one 8.25 g 5-chloro-2,4-dihydro-2-methyl-4-(2-methylphenyl)-3H-1,2,4-triazol-3-one was dissolved in 80 mL 1:1 dimethoxyethane/methanol under N$_2$. 14.0 mL sodium methoxide (30% solution in methanol) was added and the solution was heated at reflux for 3 h. The mixture was allowed to cool, diluted with ethyl acetate, washed with water, then saturated aqueous NaCl. The combined organic extracts were dried (MgSO$_4$), filtered, and concentrated under reduced pressure. The residue was purified by flash chromatography (50–70% ethyl acetate/hexanes as eluent) and triturated with 50% diethylether/hexanes to afford 6.7 g of the title compound of Step C (95% pure). $^1$H NMR (CDCl$_3$) δ7.35–7.27 (m,3H), 7.18 (d,1H), 3.94 (s,3H), 3.46 (s,3H), 2.22 (s,3H).

Step D: Preparation of 4-[2-(Bromomethyl)phenyl]-2,4-dihydro-5-methoxy-2-methyl-3H-1,2,4-triazol-3-one To a solution/suspension of 6.7 g 2,4-dihydro-5-methoxy-2-methyl-4-(2-methylphenyl)-3H-1,2,4-triazol-3-one dissolved in 95 mL carbon tetrachloride under N$_2$ was added N-bromosuccinimide (6.53 g) followed by a catalytic amount of benzoyl peroxide. The solution was heated at reflux for 2 h. Another 1.63 g N-bromosuccinimide and a catalytic amount of benzoyl peroxide were added and the solution was heated at reflux for an hour. After cooling, methylene chloride was added and the organic layer was washed successively with water, then 0.1 N sodium thiosulfate solution, then saturated aqueous NaCl. The combined organic extracts were dried (MgSO$_4$), filtered, and concentrated under reduced pressure. The residue was purified by flash chromatography (3 –10% diethylether/methylene chloride as eluent) to afford 3.12 g of the title compound of Step D. $^1$H NMR (CDCl$_3$) δ7.5 (m,1H), 7.44 (m,2H), 7.22 (m,1H), 4.60 (d,1H), 4.36 (d,1H), 3.96 (s,3H), 3.47 (s,3H).

Step E: Preparation of 2,4-Dihydro-5-methoxy-2-methyl-4 [2-[[[(phenylmethylene)-amine]oxy]methyl]phenyl]-3H-1, 2,4-triazol-3-one 0.40 g 4-[2-(bromomethyl)phenyl]-2,4-dihydro-5-methoxy-2-methyl-3H-1,2,4-triazol-3-one was dissolved in approximately 5 mL N,N-dimethylfonnamide under N$_2$ and to this was added 0.20 g acetophenone oxime, followed by 0.07 g of 60% sodium hydride. The solution was allowed to stir 4 h at room temperature then was diluted with ethyl acetate, washed with water, then saturated aqueous NaCl. The organic phase was dried (MgSO$_4$), filtered, and concentrated under reduced pressure. The residue was purified by flash chromatography (60% ethyl acetate/hexanes as eluent) to afford 0.38 g of the title compound of Step E. $^1$H NMR (CDCl$_3$) δ7.6 (m,3H), 7.44 (m,2H), 7.35 (m,3H), 7.25 (m,1H), 5.26 (d,1H), 5.22 (d,1H), 3.88 (s,3H), 3.40 (s,3H), 2.20 (s,3H).

By the general procedures described herein, or through obvious modifications thereof, the compound of the Tables 1–26 can be prepared.

The following abbreviations are used in the Tables which follow. All alkyl groups are the normal isomers unless indicated otherwise.

TABLE 1

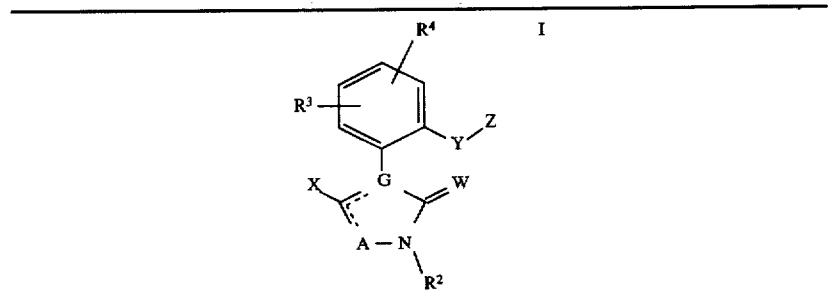

Compounds of Formula I wherein: G = C, W = O, R$^3$ = R$^4$ = H, Y = CH$_2$ON=C(CH$_3$), Z = 3-CF$_3$—Ph, the floating double bond is attached to G, and

| X | A | X | A | X | A | X | A |
|---|---|---|---|---|---|---|---|
| | | | R$^2$ = Me | | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$O=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-propyl)O | O | (c-propyl)S | O | (c-propyl)O | S | (c-propyl)S | S |
| | | | R$^2$ = Et | | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$O=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-propyl)O | O | (c-propyl)S | O | (c-propyl)O | S | (c-propyl)S | S |
| | | | R$^2$ = n-Pr | | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$O=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-propyl)O | O | (c-propyl)S | O | (c-propyl)O | S | (c-propyl)S | S |
| | | | R$^2$ = H | | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$O=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| (c-propyl)O | O | (c-propyl)S | O | (c-propyl)O | S | (c-propyl)S | S |

TABLE 1-continued

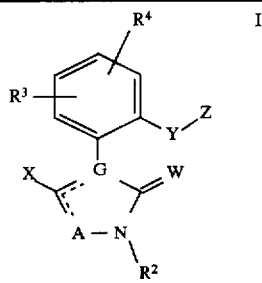

Compounds of Formula I wherein: G = C, W = O, $R^3 = R^4$ = H, Y = $CH_2ON=C(CH_3)$, Z = 3-$CF_3$—Ph, the floating double bond is attached to G, and

| X | A | X | A | X | A | X | A |
|---|---|---|---|---|---|---|---|
| | | | | $R^2$ = Me | | | |
| MeO | NH | MeS | NH | MeO | NMe | MeS | NMe |
| EtO | NH | EtS | NH | EtO | NMe | EtS | NMe |
| n-PrO | NH | n-PrS | NH | n-PrO | NMe | n-PrS | NMe |
| $H_2C$=$CHCH_2O$ | NH | $H_2C$=$CHCH_2S$ | NH | $H_2C$=$CHCH_2O$ | NMe | $H_2O$=$CHCH_2S$ | NMe |
| HC≡$CCH_2O$ | NH | HC≡$CCH_2S$ | NH | HC≡$CCH_2O$ | NMe | HC≡$CCH_2S$ | NMe |
| $CF_3O$ | NH | $CF_3S$ | NH | $CF_3O$ | NMe | $CF_3S$ | NMe |
| (c-propyl)O | NH | (c-propyl)S | NH | (c-propyl)O | NMe | (c-propyl)S | NMe |
| | | | | $R^2$ = H | | | |
| MeO | NH | MeS | NH | MeO | NMe | MeS | NMe |
| EtO | NH | EtS | NH | EtO | NMe | EtS | NMe |
| n-PrO | NH | n-PrS | NH | n-PrO | NMe | n-PrS | NMe |
| $H_2C$=$CHCH_2O$ | NH | $H_2C$=$CHCH_2S$ | NH | $H_2C$=$CHCH_2O$ | NMe | $H_2O$=$CHCH_2S$ | NMe |
| HC≡$CCH_2O$ | NH | HC≡$CCH_2S$ | NH | HC≡$CCH_2O$ | NMe | HC≡$CCH_2S$ | NMe |
| $CF_3O$ | NH | $CF_3S$ | NH | $CF_3O$ | NMe | $CF_3S$ | NMe |
| (c-propyl)O | NH | (c-propyl)S | NH | (c-propyl)O | NMe | (c-propyl)S | S | n = normal
i = iso
Me = methyl
Et = ethyl
MeO = methoxy
Pr = propyl
CN = cyano
c = cyclo
MeS = methylthio
Bu = butyl
Ph = phenyl
$NO_2$ = nitro

TABLE 2

Compounds of Formula I wherein: G = N, W = O, $R^3 = R^4$ = H, Y = $CH_2ON=C(CH_3)$, Z = 3-$CF_3$-Ph, the floating double bond is attached to A, and

| X | A | X | A | X | A | X | A |
|---|---|---|---|---|---|---|---|
| | | | | $R^2$ = Me | | | |
| MeO | N | MeS | N | MeO | CH | MeO | CH |
| EtO | N | EtS | N | EtO | CH | EtO | CH |
| n-PrO | N | n-PrS | N | n-PrO | CH | n-PrO | CH |
| $H_2C$=$CHCH_2O$ | N | $H_2C$=$CHCH_2S$ | N | $H_2C$=$CHCH_2O$ | CH | $H_2C$=$CHCH_2O$ | CH |
| HC≡$CCH_2O$ | N | HC≡$CCH_2S$ | N | HC≡$CCH_2O$ | CH | HC≡$CCH_2O$ | CH |
| $CF_3O$ | N | $CF_3S$ | N | $CF_3O$ | CH | $CF_3O$ | CH |
| (c-propyl)O | N | (c-propyl)S | N | (c-propyl)O | CH | (c-propyl)O | CH |
| | | | | $R^2$ = Et | | | |
| MeO | N | MeS | N | MeO | CH | MeO | CH |
| EtO | N | EtS | N | EtO | CH | EtO | CH |
| n-PrO | N | n-PrS | N | n-PrO | CH | n-PrO | CH |
| $H_2C$=$CHCH_2O$ | N | $H_2C$=$CHCH_2S$ | N | $H_2C$=$CHCH_2O$ | CH | $H_2C$=$CHCH_2O$ | CH |
| HC≡$CCH_2O$ | N | HC≡$CCH_2S$ | N | HC≡$CCH_2O$ | CH | HC≡$CCH_2O$ | CH |
| $CF_3O$ | N | $CF_3S$ | N | $CF_3O$ | CH | $CF_3O$ | CH |

TABLE 2-continued

Compounds of Formula I wherein: G = N, W = O,
$R^3 = R^4 = H$, Y = $CH_2ON=C(CH_3)$, Z = 3-$CF_3$-Ph,
the floating double bond is attached to A, and

| X | A | X | A | X | A | X | A |
|---|---|---|---|---|---|---|---|
| (c-propyl)O | N | (c-propyl)S | N | (c-propyl)O | CH | (c-propyl)O | CH |
| | | | | $R^2$ = n-Pr | | | |
| MeO | N | MeS | N | MeO | CH | MeO | CH |
| EtO | N | EtS | N | EtO | CH | EtO | CH |
| n-PrO | N | n-PrS | N | n-PrO | CH | n-PrO | CH |
| $H_2C=CHCH_2O$ | N | $H_2C=CHCH_2S$ | N | $H_2C=CHCH_2O$ | CH | $H_2C=CHCH_2O$ | CH |
| $HC\equiv CCH_2O$ | N | $HC\equiv CCH_2S$ | N | $HC\equiv CCH_2O$ | CH | $HC\equiv CCH_2O$ | CH |
| $CF_3O$ | N | $CF_3S$ | N | $CF_3O$ | CH | $CF_3O$ | CH |
| (c-propyl)O | N | (c-propyl)S | N | (c-propyl)O | CH | (c-propyl)O | CH |
| | | | | $R^2$ = H | | | |
| MeO | N | MeS | N | MeO | CH | MeO | CH |
| EtO | N | EtS | N | EtO | CH | EtO | CH |
| n-PrO | N | n-PrS | N | n-PrO | CH | n-PrO | CH |
| $H_2C=CHCH_2O$ | N | $H_2C=CHCH_2S$ | N | $H_2C=CHCH_2O$ | CH | $H_2C=CHCH_2O$ | CH |
| $HC\equiv CCH_2O$ | N | $HC\equiv CCH_2S$ | N | $HC\equiv CCH_2O$ | CH | $HC\equiv CCH_2O$ | CH |
| $CF_3O$ | N | $CF_3S$ | N | $CF_3O$ | CH | $CF_3O$ | CH |
| (c-propyl)O | N | (c-propyl)S | N | (c-propyl)O | CH | (c-propyl)O | CH |
| | | | | $R^2$ = Me | | | |
| MeO | CMe | MeS | CMe | MeO | CEt | MeO | CEt |
| EtO | CMe | EtS | CMe | EtO | CEt | EtO | CEt |
| n-PrO | CMe | n-PrS | CMe | n-PrO | CEt | n-PrO | CEt |
| $H_2C=CHCH_2O$ | CMe | $H_2C=CHCH_2S$ | CMe | $H_2C=CHCH_2O$ | CEt | $H_2C=CHCH_2O$ | CEt |
| $HC\equiv CCH_2O$ | CMe | $HC\equiv CCH_2S$ | CMe | $HC\equiv CCH_2O$ | CEt | $HC\equiv CCH_2O$ | CEt |
| $CF_3O$ | CMe | $CF_3S$ | CMe | $CF_3O$ | CEt | $CF_3O$ | CEt |
| (c-propyl)O | CMe | (c-propyl)S | CMe | (c-propyl)O | CEt | (c-propyl)O | CEt |
| | | | | $R^2$ = H | | | |
| MeO | CEt | MeS | CEt | MeO | CMe | MeO | CMe |
| EtO | CEt | EtS | CEt | EtO | CMe | EtO | CMe |
| n-PrO | CEt | n-PrS | CEt | n-PrO | CMe | n-PrO | CMe |
| $H_2C=CHCH_2O$ | CEt | $H_2C=CHCH_2S$ | CEt | $H_2C=CHCH_2O$ | CMe | $H_2C=CHCH_2O$ | CMe |
| $HC\equiv CCH_2O$ | CEt | $HC\equiv CCH_2S$ | CEt | $HC\equiv CCH_2O$ | CMe | $HC\equiv CCH_2O$ | CMe |
| $CF_3O$ | CEt | $CF_3S$ | CEt | $CF_3O$ | CMe | $CF_3O$ | CMe |
| (c-propyl)O | CEt | (c-propyl)S | CEt | (c-propyl)O | CMe | (c-propyl)O | CMe |

TABLE 3

Compounds of Formula I wherein: G = C, W = O,
$R^3 = R^4 = H$, Y = $CH_2O$, Z = 2-Me-Ph,
the floating double bond is attached to G, and

| X | A | X | A | X | A | X | A |
|---|---|---|---|---|---|---|---|
| | | | | $R^2$ = Me | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| $H_2C=CHCH_2O$ | O | $H_2C=CHCH_2S$ | O | $H_2C=CHCH_2O$ | S | $H_2C=CHCH_2S$ | S |
| $HC\equiv CCH_2O$ | O | $HC\equiv CCH_2S$ | O | $HC\equiv CCH_2O$ | S | $HC\equiv CCH_2S$ | S |
| $CF_3O$ | O | $CF_3S$ | O | $CF_3O$ | S | $CF_3S$ | S |
| (c-propyl)O | O | (c-propyl)S | O | (c-propyl)O | S | (c-propyl)S | S |
| | | | | $R^2$ = Et | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| $H_2C=CHCH_2O$ | O | $H_2C=CHCH_2S$ | O | $H_2C=CHCH_2O$ | S | $H_2C=CHCH_2S$ | S |
| $HC\equiv CCH_2O$ | O | $HC\equiv CCH_2S$ | O | $HC\equiv CCH_2O$ | S | $HC\equiv CCH_2S$ | S |
| $CF_3O$ | O | $CF_3S$ | O | $CF_3O$ | S | $CF_3S$ | S |
| (c-propyl)O | O | (c-propyl)S | O | (c-propyl)O | S | (c-propyl)S | S |
| | | | | $R^2$ = n-Pr | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| $H_2C=CHCH_2O$ | O | $H_2C=CHCH_2S$ | O | $H_2C=CHCH_2O$ | S | $H_2C=CHCH_2S$ | S |

TABLE 3-continued

Compounds of Formula I wherein: G = C, W = O,
R³ = R⁴ = H, Y = CH₂O, Z = 2-Me-Ph,
the floating double bond is attached to G, and

| X | A | X | A | X | A | X | A |
|---|---|---|---|---|---|---|---|
| HC≡CCH₂O | O | HC≡CCH₂S | O | HC≡CCH₂O | S | HC≡CCH₂S | S |
| CF₃O | O | CF₃S | O | CF₃O | S | CF₃S | S |
| (c-propyl)O | O | (c-propyl)S | O | (c-propyl)O | S | (c-propyl)S | S |

R² = H

| MeO | O | MeS | O | MeO | S | MeS | S |
| EtO | O | EtS | O | EtO | S | EtS | S |
| n-PrO | O | n-PrS | O | n-PrO | S | n-PrS | S |
| H₂C=CHCH₂O | O | H₂C=CHCH₂S | O | H₂C=CHCH₂O | S | H₂C=CHCH₂S | S |
| HC≡CCH₂O | O | HC≡CCH₂S | O | HC≡CCH₂O | S | HC≡CCH₂S | S |
| CF₃O | O | CF₃S | O | CF₃O | S | CF₃S | S |
| (c-propyl)O | O | (c-propyl)S | O | (c-propyl)O | S | (c-propyl)S | S |

R² = Me

| MeO | NH | MeS | NH | MeO | NMe | MeS | NMe |
| EtO | NH | EtS | NH | EtO | NMe | EtS | NMe |
| n-PrO | NH | n-PrS | NH | n-PrO | NMe | n-PrS | NMe |
| H₂C=CHCH₂O | NH | H₂C=CHCH₂S | NH | H₂C=CHCH₂O | NMe | H₂C=CHCH₂S | NMe |
| HC≡CCH₂O | NH | HC≡CCH₂S | NH | HC≡CCH₂O | NMe | HC≡CCH₂S | NMe |
| CF₃O | NH | CF₃S | NH | CF₃O | NMe | CF₃S | NMe |
| (c-propyl)O | NH | (c-propyl)S | NH | (c-propyl)O | NMe | (c-propyl)S | NMe |

R² = H

| MeO | NH | MeS | NH | MeO | NMe | MeS | NMe |
| EtO | NH | EtS | NH | EtO | NMe | EtS | NMe |
| n-PrO | NH | n-PrS | NH | n-PrO | NMe | n-PrS | NMe |
| H₂C=CHCH₂O | NH | H₂C=CHCH₂S | NH | H₂C=CHCH₂O | NMe | H₂C=CHCH₂S | NMe |
| HC≡CCH₂O | NH | HC≡CCH₂S | NH | HC≡CCH₂O | NMe | HC≡CCH₂S | NMe |
| CF₃O | NH | CF₃S | NH | CF₃O | NMe | CF₃S | NMe |
| (c-propyl)O | NH | (c-propyl)S | NH | (c-propyl)O | NMe | (c-propyl)S | NMe |

TABLE 4

Compounds of Formula I wherein: G = N, W = O,
R³ = R⁴ = H, Y = CH₂O, Z = 2-Me-Ph,
the floating double bond is attached to A, and

| X | A | X | A | X | A | X | A |
|---|---|---|---|---|---|---|---|

R² = Me

| MeO | N | MeS | N | MeO | CH | MeO | CH |
| EtO | N | EtS | N | EtO | CH | EtO | CH |
| n-PrO | N | n-PrS | N | n-PrO | CH | n-PrO | CH |
| H₂C=CHCH₂O | N | H₂C=CHCH₂S | N | H₂C=CHCH₂O | CH | H₂C=CHCH₂O | CH |
| HC≡CCH₂O | N | HC≡CCH₂S | N | HC≡CCH₂O | CH | HC≡CCH₂O | CH |
| CF₃O | N | CF₃S | N | CF₃O | CH | CF₃O | CH |
| (c-propyl)O | N | (c-propyl)S | N | (c-propyl)O | CH | (c-propyl)O | CH |

R² = Et

| MeO | N | MeS | N | MeO | CH | MeO | CH |
| EtO | N | EtS | N | EtO | CH | EtO | CH |
| n-PrO | N | n-PrS | N | n-PrO | CH | n-PrO | CH |
| H₂C=CHCH₂O | N | H₂C=CHCH₂S | N | H₂C=CHCH₂O | CH | H₂C=CHCH₂O | CH |
| HC≡CCH₂O | N | HC≡CCH₂S | N | HC≡CCH₂O | CH | HC≡CCH₂O | CH |
| CF₃O | N | CF₃S | N | CF₃O | CH | CF₃O | CH |
| (c-propyl)O | N | (c-propyl)S | N | (c-propyl)O | CH | (c-propyl)O | CH |

R² = n-Pr

| MeO | N | MeS | N | MeO | CH | MeO | CH |
| EtO | N | EtS | N | EtO | CH | EtO | CH |
| n-PrO | N | n-PrS | N | n-PrO | CH | n-PrO | CH |
| H₂C=CHCH₂O | N | H₂C=CHCH₂S | N | H₂C=CHCH₂O | CH | H₂C=CHCH₂O | CH |
| HC≡CCH₂O | N | HC≡CCH₂S | N | HC≡CCH₂O | CH | HC≡CCH₂O | CH |
| CF₃O | N | CF₃S | N | CF₃O | CH | CF₃O | CH |
| (c-propyl)O | N | (c-propyl)S | N | (c-propyl)O | CH | (c-propyl)O | CH |

R² = H

| MeO | N | MeS | N | MeO | CH | MeO | CH |
| EtO | N | EtS | N | EtO | CH | EtO | CH |

TABLE 4-continued

Compounds of Formula I wherein: G = N, W = O, $R^3 = R^4 = H$, Y = CH$_2$O, Z = 2-Me-Ph, the floating double bond is attached to A, and

| X | A | X | A | X | A | X | A |
|---|---|---|---|---|---|---|---|
| n-PrO | N | n-PrS | N | n-PrO | CH | n-PrO | CH |
| H$_2$C=CHCH$_2$O | N | H$_2$C=CHCH$_2$S | N | H$_2$C=CHCH$_2$O | CH | H$_2$C=CHCH$_2$O | CH |
| HC≡CCH$_2$O | N | HC≡CCH$_2$S | N | HC≡CCH$_2$O | CH | HC≡CCH$_2$O | CH |
| CF$_3$O | N | CF$_3$S | N | CF$_3$O | CH | CF$_3$O | CH |
| (c-propyl)O | N | (c-propyl)S | N | (c-propyl)O | CH | (c-propyl)O | CH |

$R^2$ = Me

| X | A | X | A | X | A | X | A |
|---|---|---|---|---|---|---|---|
| MeO | CMe | MeS | CMe | MeO | CEt | MeO | CEt |
| EtO | CMe | EtS | CMe | EtO | CEt | EtO | CEt |
| n-PrO | CMe | n-PrS | CMe | n-PrO | CEt | n-PrO | CEt |
| H$_2$C=CHCH$_2$O | CMe | H$_2$C=CHCH$_2$S | CMe | H$_2$C=CHCH$_2$O | CEt | H$_2$C=CHCH$_2$O | CEt |
| HC≡CCH$_2$O | CMe | HC≡CCH$_2$S | CMe | HC≡CCH$_2$O | CEt | HC≡CCH$_2$O | CEt |
| CF$_3$O | CMe | CF$_3$S | CMe | CF$_3$O | CEt | CF$_3$O | CEt |
| (c-propyl)O | CMe | (c-propyl)S | CMe | (c-propyl)O | CEt | (c-propyl)O | CEt |

$R^2$ = H

| X | A | X | A | X | A | X | A |
|---|---|---|---|---|---|---|---|
| MeO | CEt | MeS | CEt | MeO | CMe | MeO | CMe |
| EtO | CEt | EtS | CEt | EtO | CMe | EtO | CMe |
| n-PrO | CEt | n-PrS | CEt | n-PrO | CMe | n-PrO | CMe |
| H$_2$C=CHCH$_2$O | CEt | H$_2$C=CHCH$_2$S | CEt | H$_2$C=CHCH$_2$O | CMe | H$_2$C=CHCH$_2$O | CMe |
| HC≡CCH$_2$O | CEt | HC≡CCH$_2$S | CEt | HC≡CCH$_2$O | CMe | HC≡CCH$_2$O | CMe |
| CF$_3$O | CEt | CF$_3$S | CEt | CF$_3$O | CMe | CF$_3$O | CMe |
| (c-propyl)O | CEt | (c-propyl)S | CEt | (c-propyl)O | CMe | (c-propyl)O | CMe |

TABLE 5

Compounds of Formula I wherein: G = C, W = S, $R^3 = R^4 = H$, Y = CH$_2$ON=C(CH$_3$), Z = 3-CF$_3$-Ph, the floating double bond is attached to G, and

| X | A | X | A | X | A | X | A |
|---|---|---|---|---|---|---|---|

$R^2$ = Me

| X | A | X | A | X | A | X | A |
|---|---|---|---|---|---|---|---|
| MeO | O | MeS | O | MeO | S | MeS | S |
| EtO | O | EtS | O | EtO | S | EtS | S |
| n-PrO | O | n-PrS | O | n-PrO | S | n-PrS | S |
| H$_2$C=CHCH$_2$O | O | H$_2$C=CHCH$_2$S | O | H$_2$C=CHCH$_2$O | S | H$_2$C=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| MeO | NH | MeO | NMe | MeO | NEt | MeS | NPr |

TABLE 6

Compounds of Formula I wherein: A = N, G = N, W = S, $R^3 = R^4 = H$, Y = CH$_2$ON=C(Me), Z = 3-CF$_3$-Ph, the floating double bond is attached to A, and $R^2$ = Me

| X | X | X | X |
|---|---|---|---|
| MeO | EtO | n-PrO | H$_2$C=CHCH$_2$O |
| HC≡CCH$_2$O | CF$_3$O | OCF$_2$H | OCH$_2$CF$_3$ |
| (c-propyl)O | MeS | EtS | n-PrS |
| H$_2$C=CHCH$_2$S | HC≡CCH$_2$S | CF$_3$S | (c-propyl)S |

TABLE 7

Compounds of Formula I wherein: G = C, W = S, $R^3 = R^4 = H$, Y = $CH_2O$, Z = 2-Me-Ph, the floating double bond is attached to G, and

| X | A | X | A | X | A | X | A |
|---|---|---|---|---|---|---|---|
| | | | | $R^2$ = Me | | | |
| MeO | O | MeS | O | MeO | S | MeS | S |
| EtO | O | EtS | O | EtO | S | EtS | S |
| n-PrO | O | n-PrS | O | n-PrO | S | n-PrS | S |
| $H_2C$=CHCH$_2$O | O | $H_2C$=CHCH$_2$S | O | $H_2C$=CHCH$_2$O | S | $H_2C$=CHCH$_2$S | S |
| HC≡CCH$_2$O | O | HC≡CCH$_2$S | O | HC≡CCH$_2$O | S | HC≡CCH$_2$S | S |
| CF$_3$O | O | CF$_3$S | O | CF$_3$O | S | CF$_3$S | S |
| MeO | NH | MeO | NMe | MeO | NEt | MeS | NPr |

TABLE 8

Compounds of Formula I wherein: A = N, G = N, W = S, $R^3 = R^4 = H$, Y = $CH_2O$, Z = 2-Me-Ph, the floating double bond is attached to A, and

| X | X | X | X |
|---|---|---|---|
| | $R^2$ = Me | | |
| MeO | EtO | n-PrO | $H_2C$=CHCH$_2$O |
| HC≡CCH$_2$O | CF$_3$O | OCF$_2$H | OCH$_2$CF$_3$ |
| (c-propyl)O | MeS | EtS | n-PrS |
| $H_2C$=CHCH$_2$S | HC≡CCH$_2$S | CF$_3$S | (c-propyl)S |

TABLE 9

Compounds of Formula I wherein: G = C, A = W = O, X = MeO, $R^2$ = Me, Y = $CH_2ON$=C(Me), Z = 3-CF$_3$-Ph, the floating double bond is attached to G, and

| $R^3$ | $R^4$ | $R^3$ | $R^4$ | $R^3$ | $R^4$ |
|---|---|---|---|---|---|
| 3-F | H | 5-NO$_2$ | H | 3-F | 5-F |
| 5-F | H | 6-Me | H | 3-Cl | 5-Cl |
| 3-Cl | H | 3-Me | H | 4-Me | 5-Cl |
| 4-Cl | H | 4-MeO | H | 3-F | 5-CF$_3$ |

TABLE 9-continued

Compounds of Formula I wherein: G = C, A = W = O, X = MeO, $R^2$ = Me, Y = $CH_2ON$=C(Me), Z = 3-CF$_3$-Ph, the floating double bond is attached to G, and

| $R^3$ | $R^4$ | $R^3$ | $R^4$ | $R^3$ | $R^4$ |
|---|---|---|---|---|---|
| 5-Br | H | 5-CF$_3$O | H | 3-Cl | 5-NO$_2$ |
| 4-CF$_3$ | H | 5-allyl | H | 6-CF$_3$O | H |
| 5-CN | H | 4-propargyl | H | 5-Pr | H |

TABLE 10

Compounds of Formula I wherein: A = N, G = N, W = O, X = MeO, $R^2$ = Me, Y = $CH_2ON$=C(Me), Z = 3-CF$_3$-Ph, the floating double bond is attached to A, and

| $R^3$ | $R^4$ | $R^3$ | $R^4$ | $R^3$ | $R^4$ |
|---|---|---|---|---|---|
| 3-F | H | 5-NO$_2$ | H | 3-F | 5-F |
| 5-F | H | 6-Me | H | 3-Cl | 5-Cl |
| 3-Cl | H | 3-Me | H | 4-Me | 5-Cl |
| 4-Cl | H | 4-MeO | H | 3-F | 5-CF$_3$ |
| 5-Br | H | 5-CF$_3$O | H | 3-Cl | 5-NO$_2$ |
| 4-CF$_3$ | H | 5-allyl | H | 6-CF$_3$O | H |
| 5-CN | H | 4-propargyl | H | 5-Pr | H |

TABLE 11

Compounds of Formula I wherein: A = O, G = C, W = O, X = MeO, $R^2$ = Me, the floating double bond is attached to G, and

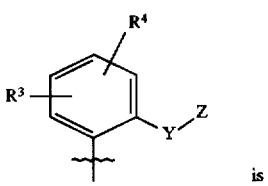

is

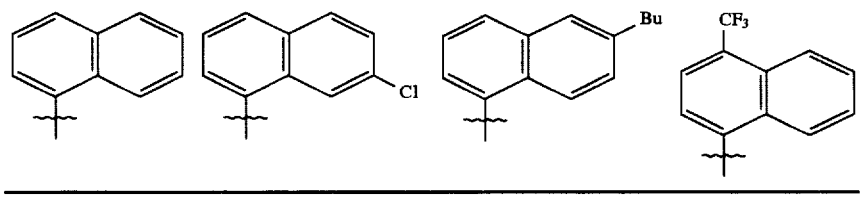

TABLE 12

Compounds of Formula I wherein: A = N, G = N, W = O, X = MeO,
R² = Me, the floating double bond is attached to A, and

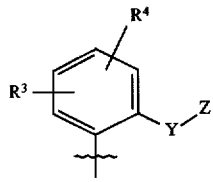

is

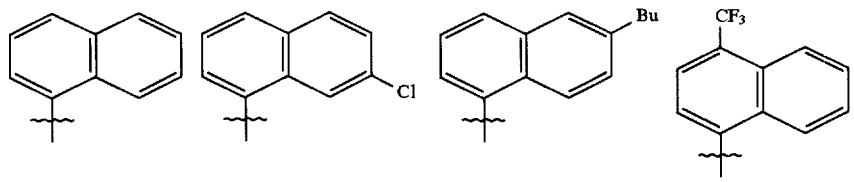

TABLE 13

Compounds of Formula I wherein: G = C, W= O,
X = MeO, R² = Me, R³ = R⁴ = H, Z = Ph,
the floating double bond is attached to G, and

| Y | Y | Y | Y | Y |
|---|---|---|---|---|
| A = O | | | | |
| S | CH₂CH₂ | CH(Me)O | SCH₂ | C(Me)=N-O |
| CH=CH | CH(Me)CH₂ | OCH₂ | SCH(Me) | O-N=CH |
| C(Me)=CH | CH₂CH(Me) | OCH(Me) | CH₂O-N=CH | O-N=C(Me) |
| CH=C(Me) | CH(Me)CH(Me) | CH₂S | CH₂O-N=C(Me) | CH₂OC(=O) |
| C(Me)=C(Me) | CH₂O | CH(Me)S | CH=N-O | CH(Me)OC(=O) |
| direct bond | C≡C | | | |
| A = S | | | | |
| S | CH₂CH₂ | CH(Me)O | SCH₂ | C(Me)=N-O |
| CH=CH | CH(Me)CH₂ | OCH₂ | SCH(Me) | O-N=CH |
| C(Me)=CH | CH₂CH(Me) | OCH(Me) | CH₂O-N=CH | O-N=C(Me) |
| CH=C(Me) | CH(Me)CH(Me) | CH₂S | CH₂O-N=C(Me) | CH₂OC(=O) |
| C(Me)=C(Me) | CH₂O | CH(Me)S | CH=N-O | CH(Me)OC(=O) |
| direct bond | C≡C | | | |
| A = NMe | | | | |
| S | CH₂CH₂ | CH(Me)O | SCH₂ | C(Me)=N-O |
| CH=CH | CH(Me)CH₂ | OCH₂ | SCH(Me) | O-N=CH |
| C(Me)=CH | CH₂CH(Me) | OCH(Me) | CH₂O-N=CH | O-N=C(Me) |
| CH=C(Me) | CH(Me)CH(Me) | CH₂S | CH₂O-N=C(Me) | CH₂OC(=O) |
| C(Me)=C(Me) | CH₂O | CH(Me)S | CH=N-O | CH(Me)OC(=O) |
| direct bond | C≡C | | | |

TABLE 14

Compounds of Formula I wherein: G = N, W = O, X = MeO, R² = Me,
R³ = R⁴ = H, Z = Ph, the floating double bond is attached to A, and

| Y | Y | Y | Y | Y |
|---|---|---|---|---|
| A = N | | | | |
| S | CH₂CH₂ | CH(Me)O | SCH₂ | C(Me)=N-O |
| CH=CH | CH(Me)CH₂ | OCH₂ | SCH(Me) | O-N=CH |
| C(Me)=CH | CH₂CH(Me) | OCH(Me) | CH₂O-N=CH | O-N=C(Me) |
| CH=C(Me) | CH(Me)CH(Me) | CH₂S | CH₂O-N=C(Me) | CH₂OC(=O) |
| C(Me)=C(Me) | CH₂O | CH(Me)S | CH=N-O | CH(Me)OC(=O) |
| direct bond | C≡C | | | |

TABLE 14-continued

Compounds of Formula I wherein: G = N, W = O, X = MeO, R² = Me,
R³ = R⁴ = H, Z = Ph, the floating double bond is attached to A, and

| Y | Y | Y | Y | Y |
|---|---|---|---|---|
| \multicolumn{5}{c}{A = S} | | | | |
| S | CH₂CH₂ | CH(Me)O | SCH₂ | C(Me)=N-O |
| CH=CH | CH(Me)CH₂ | OCH₂ | SCH(Me) | O-N=CH |
| C(Me)=CH | CH₂CH(Me) | OCH(Me) | CH₂O-N=CH | O-N=C(Me) |
| CH=C(Me) | CH(Me)CH(Me) | CH₂S | CH₂O-N=C(Me) | CH₂OC(=O) |
| C(Me)=C(Me) | CH₂O | CH(Me)S | CH=N-O | CH(Me)OC(=O) |
| direct bond | C≡C | | | |
| \multicolumn{5}{c}{A = NMe} | | | | |
| S | CH₂CH₂ | CH(Me)O | SCH₂ | C(Me)=N-O |
| CH=CH | CH(Me)CH₂ | OCH₂ | SCH(Me) | O-N=CH |
| C(Me)=CH | CH₂CH(Me) | OCH(Me) | CH₂O-N=CH | O-N=C(Me) |
| CH=C(Me) | CH(Me)CH(Me) | CH₂S | CH₂O-N=C(Me) | CH₂OC(=O) |
| C(Me)=C(Me) | CH₂O | CH(Me)S | CH=N-O | CH(Me)OC(=O) |
| direct bond | C≡C | | | |

TABLE 15

Compounds of Formula I wherein: G = C, W = O, X = MeO, R² = Me,
R³ = R⁴ = H, the floating double bond is attached to G, and

| Z | Z | Z | Z |
|---|---|---|---|
| | Y = O, A = O | | |
| hexyl | 4-octenyl | 3-pentynyl | 4-PhO-2-pyridinyl |
| PhO(CH₂)₃ | PhCH=CHCH₂ | PhC≡CCH₂ | (c-propyl)CH₂ |
| 2-Br-Ph | 2-Me-Ph | 2-Et-Ph | 6-(2-CN-PhO)-4-pyrimidinyl |
| 2-CN-Ph | 2-F-Ph | 2-Cl-Ph | 6-PhO-4-pyrimidinyl |
| 2,4-diCl-Ph | 2-Me-4-Cl-Ph | 2,4,6-triCl-Ph | 4-EtO-2-pyrimidinyl |
| 2-CF₃-Ph | 4-Ph-Ph | 3-PhO-Ph | 3-(4-pyrimidinyloxy)-Ph |
| 2-I-Ph | 3-(2-Cl-PhO)-Ph | 3-(2-Et-PhO)-Ph | 4-(2-thienyl)Ph |
| c-hexyl | 3,5-diCl-Ph | 6-Ph-2-pyridinyl | 3-(2-pyridinyloxy)Ph |
| 4-NO₂-Ph | 3,5-diCF₃-Ph | 6-PhO-4-pyridinyl | 3-pyridinyl |
| PhCH₂CH₂ | 2-MeO-Ph | 3-thienyloxy-Ph | 4-(3-Cl-2-pyridinyloxy)-Ph |
| (2-CN-Ph)CH₂ | 2,6-diMeO-Ph | 3-(4-CF₃-PhO)-Ph | 4-(PhO)-c-hexyl |
| CF₃CH₂ | 3-(2-CN-PhO)-Ph | 3-(2-Me-PhO)-Ph | 5-PhO-2-pyrimidinyl |
| 2-MeS-Ph | 5-PhO-3-pyridinyl | 5-PhO-2-pyridinyl | 6-(2-NO₂-PhO)-4-pyrimidinyl |
| i-Bu | 6-Me-2-pyridinyl | 6-PhO-2-pyridinyl | 6-(2-Cl-PhO)-4-pyrimidinyl |
| 2-CF₃O-Ph | 3-CF₃O-Ph | 6-CF₃-2-pyridinyl | 6-(2-CF₃-PhO)-4-pyrimidinyl |
| 4-Me-Ph | 4-Br-Ph | 6-PhO-3-pyridinyl | 4,6-diMeO-2-pyrimidinyl |
| 4-Cl-Ph | 3-Et-Ph | 2-pyrimidinyl | 4,6-diMe-2-pyrimidinyl |
| 3-Me-Ph | 4-Et-Ph | 4-pyrimidinyl | 6-CF₃-4-pyrimidinyl |
| 3-CF₃-Ph | 4-MeO-Ph | 4-MeO-2-pyrimidinyl | 4-CF₃-2-pyridinyl |
| 3-Cl-2-Me-Ph | 4-t-Bu-Ph | 4-Me-2-pyrimidinyl | 4-CF₃-2-pyridinyl |
| 3-t-Bu-Ph | 4-CN-Ph | 6-MeO-4-pyrimidinyl | 2-pyridinyl |
| 3-NO₂-Ph | 4-NO₂-Ph | 2-Ph-4-thiazolyl | 6-CF₃-2-pyrazinyl |
| 3-F-Ph | 4-F-Ph | 3-MeO-6-pyridazinyl | 5-CF₃-3-pyridinyl |
| 4-CF₃-Ph | 3-Ph-Ph | 5-Me-2-furanyl | 3-MeO-2-pyridinyl |
| 3,4-diCl-Ph | 3,4-diMe-Ph | 2,5-diMe-3-thienyl | 5-CN-2-pyridinyl |
| 3,4-diCF₃-Ph | 3,5-diMe-Ph | 3-OCF₂H-Ph | 6-Me-2-pyridinyl |
| 3-EtO-Ph | 3-MeS-Ph | 4-OCF₂H-Ph | |
| | Y = CH₂O, A = O | | |
| hexyl | 4-octenyl | 3-pentynyl | 4-PhO-2-pyridinyl |
| PhO(CH₂)₃ | PhCH=CHCH₂ | PhC≡CCH₂ | (c-propyl)CH₂ |
| 2-Br-Ph | 2-Me-Ph | 2-Et-Ph | 6-(2-CN-PhO)-4-pyrimidinyl |
| 2-CN-Ph | 2-F-Ph | 2-Cl-Ph | 6-PhO-4-pyrimidinyl |
| 2,4-diCl-Ph | 2-Me-4-Cl-Ph | 2,4,6-triCl-Ph | 4-EtO-2-pyrimidinyl |
| 2-CF₃-Ph | 4-Ph-Ph | 3-PhO-Ph | 3-(4-pyrimidinyloxy)-Ph |
| 2-I-Ph | 3-(2-Cl-PhO)-Ph | 3-(2-Et-PhO)-Ph | 4-(2-thienyl)Ph |
| c-hexyl | 3,5-diCl-Ph | 6-Ph-2-pyridinyl | 3-(2-pyridinyloxy)Ph |
| 4-NO₂-Ph | 3,5-diCF₃-Ph | 6-PhO-4-pyridinyl | 3-pyridinyl |
| PhCH₂CH₂ | 2-MeO-Ph | 3-thienyloxy-Ph | 4-(3-Cl-2-pyridinyloxy)-Ph |
| (2-CN-Ph)CH₂ | 2,6-diMeO-Ph | 3-(4-CF₃-PhO)-Ph | 4-(PhO)-c-hexyl |
| CF₃CH₂ | 3-(2-CN-PhO)-Ph | 3-(2-Me-PhO)-Ph | 5-PhO-2-pyrimidinyl |
| 2-MeS-Ph | 5-PhO-3-pyridinyl | 5-PhO-2-pyridinyl | 6-(2-NO₂-PhO)-4-pyrimidinyl |
| i-Bu | 6-Me-2-pyridinyl | 6-PhO-2-pyridinyl | 6-(2-Cl-PhO)-4-pyrimidinyl |
| 2-CF₃O-Ph | 3-CF₃O-Ph | 6-CF₃-2-pyridinyl | 6-(2-CF₃-PhO)-4-pyrimidinyl |
| 4-Me-Ph | 4-Br-Ph | 6-PhO-3-pyridinyl | 4,6-diMeO-2-pyrimidinyl |

TABLE 15-continued

Compounds of Formula I wherein: G = C, W = O, X = MeO, $R^2$ = Me, $R^3 = R^4$ = H, the floating double bond is attached to G, and

| Z | Z | Z | Z |
|---|---|---|---|
| 4-Cl-Ph | 3-Et-Ph | 2-pyrimidinyl | 4,6-diMe-2-pyrimidinyl |
| 3-Me-Ph | 4-Et-Ph | 4-pyrimidinyl | 6-CF$_3$-4-pyrimidinyl |
| 3-CF$_3$-Ph | 4-MeO-Ph | 4-MeO-2-pyrimidinyl | 4-CF$_3$-2-pyridinyl |
| 3-Cl-2-Me-Ph | 4-t-Bu-Ph | 4-Me-2-pyrimidinyl | 4-CF$_3$-2-pyrimidinyl |
| 3-t-Bu-Ph | 4-CN-Ph | 6-MeO-4-pyrimidinyl | 2-pyridinyl |
| 3-NO$_2$-Ph | 4-NO$_2$-Ph | 2-Ph-4-thiazolyl | 6-CF$_3$-2-pyrazinyl |
| 3-F-Ph | 4-F-Ph | 3-MeO-6-pyridazinyl | 5-CF$_3$-3-pyridinyl |
| 4-CF$_3$-Ph | 3-Ph-Ph | 5-Me-2-furanyl | 3-MeO-2-pyridinyl |
| 3,4-diCl-Ph | 3,4-diMe-Ph | 2,5-diMe-3-thienyl | 5-CN-2-pyridinyl |
| 3,4-diCF$_3$-Ph | 3,5-diMe-Ph | 3-OCF$_2$H-Ph | 6-Me-2-pyridinyl |
| 3-EtO-Ph | 3-MeS-Ph | 4-OCF$_2$H-Ph | |
| | | Y = O, A = NMe | |
| hexyl | 4-octenyl | 3-pentynyl | 4-PhO-2-pyridinyl |
| PhO(CH$_2$)$_3$ | PhCH=CHCH$_2$ | PhC≡CCH$_2$ | (c-propyl)CH$_2$ |
| 2-Br-Ph | 2-Me-Ph | 2-Et-Ph | 6-(2-CN-PhO)-4-pyrimidinyl |
| 2-CN-Ph | 2-F-Ph | 2-Cl-Ph | 6-PhO-4-pyrimidinyl |
| 2,4-diCl-Ph | 2-Me-4-Cl-Ph | 2,4,6-triCl-Ph | 4-EtO-2-pyrimidinyl |
| 2-CF$_3$-Ph | 4-Ph-Ph | 3-PhO-Ph | 3-(4-pyrimidinyloxy)-Ph |
| 2-I-Ph | 3-(2-Cl-PhO)-Ph | 3-(2-Et-PhO)-Ph | 4-(2-thienyl)Ph |
| c-hexyl | 3,5-diCl-Ph | 6-Ph-2-pyridinyl | 3-(2-pyridinyloxy)Ph |
| 4-NO$_2$-Ph | 3,5-diCF$_3$-Ph | 6-PhO-4-pyridinyl | 3-pyridinyl |
| PhCH$_2$CH$_2$ | 2-MeO-Ph | 3-thienyloxy-Ph | 4-(3-Cl-2-pyridinyloxy)-Ph |
| (2-CN-Ph)CH$_2$ | 2,6-diMeO-Ph | 3-(4-CF$_3$-PhO)-Ph | 4-(PhO)-c-hexyl |
| CF$_3$CH$_2$ | 3-(2-CN-PhO)-Ph | 3-(2-Me-PhO)-Ph | 5-PhO-2-pyrimidinyl |
| 2-MeS-Ph | 5-PhO-3-pyridinyl | 5-PhO-2-pyridinyl | 6-(2-NO$_2$-PhO)-4-pyrimidinyl |
| i-Bu | 6-Me-2-pyridinyl | 6-PhO-2-pyridinyl | 6-(2-Cl-PhO)-4-pyrimidinyl |
| 2-CF$_3$O-Ph | 3-CF$_3$O-Ph | 6-CF$_3$-2-pyridinyl | 6-(2-CF$_3$-PhO)-4-pyrimidinyl |
| 4-Me-Ph | 4-Br-Ph | 6-PhO-3-pyridinyl | 4,6-diMeO-2-pyrimidinyl |
| 4-Cl-Ph | 3-Et-Ph | 2-pyrimidinyl | 4,6-diMe-2-pyrimidinyl |
| 3-Me-Ph | 4-Et-Ph | 4-pyrimidinyl | 6-CF$_3$-4-pyrimidinyl |
| 3-CF$_3$-Ph | 4-MeO-Ph | 4-MeO-2-pyrimidinyl | 4-CF$_3$-2-pyridinyl |
| 3-Cl-2-Me-Ph | 4-t-Bu-Ph | 4-Me-2-pyrimidinyl | 4-CF$_3$-2-pyrimidinyl |
| 3-t-Bu-Ph | 4-CN-Ph | 6-MeO-4-pyrimidinyl | 2-pyridinyl |
| 3-NO$_2$-Ph | 4-NO$_2$-Ph | 2-Ph-4-thiazolyl | 6-CF$_3$-2-pyrazinyl |
| 3-F-Ph | 4-F-Ph | 3-MeO-6-pyridazinyl | 5-CF$_3$-3-pyridinyl |
| 4-CF$_3$-Ph | 3-Ph-Ph | 5-Me-2-furanyl | 3-MeO-2-pyridinyl |
| 3,4-diCl-Ph | 3,4-diMe-Ph | 2,5-diMe-3-thienyl | 5-CN-2-pyridinyl |
| 3,4-diCF$_3$-Ph | 3,5-diMe-Ph | 3-OCF$_2$H-Ph | 6-Me-2-pyridinyl |
| 3-EtO-Ph | 3-MeS-Ph | 4-OCF$_2$H-Ph | |
| | | Y = CH$_2$O, A = NMe | |
| hexyl | 4-octenyl | 3-pentynyl | 4-PhO-2-pyridinyl |
| PhO(CH$_2$)$_3$ | PhCH=CHCH$_2$ | PhC≡CCH$_2$ | (c-propyl)CH$_2$ |
| 2-Br-Ph | 2-Me-Ph | 2-Et-Ph | 6-(2-CN-PhO)-4-pyrimidinyl |
| 2-CN-Ph | 2-F-Ph | 2-Cl-Ph | 6-PhO-4-pyrimidinyl |
| 2,4-diCl-Ph | 2-Me-4-Cl-Ph | 2,4,6-triCl-Ph | 4-EtO-2-pyrimidinyl |
| 2-CF$_3$-Ph | 4-Ph-Ph | 3-PhO-Ph | 3-(4-pyrimidinyloxy)-Ph |
| 2-I-Ph | 3-(2-Cl-PhO)-Ph | 3-(2-Et-PhO)-Ph | 4-(2-thienyl)Ph |
| c-hexyl | 3,5-diCl-Ph | 6-Ph-2-pyridinyl | 3-(2-pyridinyloxy)Ph |
| 4-NO$_2$-Ph | 3,5-diCF$_3$-Ph | 6-PhO-4-pyridinyl | 3-pyridinyl |
| PhCH$_2$CH$_2$ | 2-MeO-Ph | 3-thienyloxy-Ph | 4-(3-Cl-2-pyridinyloxy)-Ph |
| (2-CN-Ph)CH$_2$ | 2,6-diMeO-Ph | 3-(4-CF$_3$-PhO)-Ph | 4-(PhO)-c-hexyl |
| CF$_3$CH$_2$ | 3-(2-CN-PhO)-Ph | 3-(2-Me-PhO)-Ph | 5-PhO-2-pyrimidinyl |
| 2-MeS-Ph | 5-PhO-3-pyridinyl | 5-PhO-2-pyridinyl | 6-(2-NO$_2$-PhO)-4-pyrimidinyl |
| i-Bu | 6-Me-2-pyridinyl | 6-PhO-2-pyridinyl | 6-(2-Cl-PhO)-4-pyrimidinyl |
| 2-CF$_3$O-Ph | 3-CF$_3$O-Ph | 6-CF$_3$-2-pyridinyl | 6-(2-CF$_3$-PhO)-4-pyrimidinyl |
| 4-Me-Ph | 4-Br-Ph | 6-PhO-3-pyridinyl | 4,6-diMeO-2-pyrimidinyl |
| 4-Cl-Ph | 3-Et-Ph | 2-pyrimidinyl | 4,6-diMe-2-pyrimidinyl |
| 3-Me-Ph | 4-Et-Ph | 4-pyrimidinyl | 6-CF$_3$-4-pyrimidinyl |
| 3-CF$_3$-Ph | 4-MeO-Ph | 4-MeO-2-pyrimidinyl | 4-CF$_3$-2-pyridinyl |
| 3-Cl-2-Me-Ph | 4-t-Bu-Ph | 4-Me-2-pyrimidinyl | 4-CF$_3$-2-pyrimidinyl |
| 3-t-Bu-Ph | 4-CN-Ph | 6-MeO-4-pyrimidinyl | 2-pyridinyl |
| 3-NO$_2$-Ph | 4-NO$_2$-Ph | 2-Ph-4-thiazolyl | 6-CF$_3$-2-pyrazinyl |
| 3-F-Ph | 4-F-Ph | 3-MeO-6-pyridazinyl | 5-CF$_3$-3-pyridinyl |
| 4-CF$_3$-Ph | 3-Ph-Ph | 5-Me-2-furanyl | 3-MeO-2-pyridinyl |
| 3,4-diCl-Ph | 3,4-diMe-Ph | 2,5-diMe-3-thienyl | 5-CN-2-pyridinyl |
| 3,4-diCF$_3$-Ph | 3,5-diMe-Ph | 3-OCF$_2$H-Ph | 6-Me-2-pyridinyl |
| 3-EtO-Ph | 3-MeS-Ph | 4-OCF$_2$H-Ph | |

TABLE 16

Compounds of Formula I wherein: A = O, G = C, W = O, X = MeO,
R² = Me, R³ = R⁴ = H, the floating double bond is attached to G, and

| Z | Z | Z | Z |
|---|---|---|---|
| \multicolumn{4}{c}{Y = CH₂ON═C(CH₃).} | | | |

| Z | Z | Z | Z |
|---|---|---|---|
| hexyl | 4-octenyl | 3-pentynyl | 4-PhO-2-pyridinyl |
| PhO(CH₂)₃ | PhCH═CHCH₂ | PhC≡CCH₂ | (c-propyl)CH₂ |
| 2-Br-Ph | 2-Me-Ph | 2-Et-Ph | 6-(2-CN-PhO)-4-pyrimidinyl |
| 2-CN-Ph | 2-F-Ph | 2-Cl-Ph | 6-PhO-4-pyrimidinyl |
| 2,4-diCl-Ph | 2-Me-4-Cl-Ph | 2,4,6-triCl-Ph | 4-EtO-2-pyrimidinyl |
| 2-CF₃-Ph | 4-Ph-Ph | 3-PhO-Ph | 3-(4-pyrimidinyloxy)-Ph |
| 2-I-Ph | 3-(2-Cl-PhO)-Ph | 3-(2-Et-PhO)-Ph | 4-(2-thienyl)Ph |
| c-hexyl | 3,5-diCl-Ph | 6-Ph-2-pyridinyl | 3-(2-pyridinyloxy)Ph |
| 4-NO₂-Ph | 3,5-diCF₃-Ph | 6-PhO-4-pyridinyl | 3-pyridinyl |
| PhCH₂CH₂ | 2-MeO-Ph | 3-thienyloxy-Ph | 4-(3-Cl-2-pyridinyloxy)-Ph |
| (2-CN-Ph)CH₂ | 2,6-diMeO-Ph | 3-(4-CF₃-PhO)-Ph | 4-(PhO)-c-hexyl |
| CF₃CH₂ | 3-(2-CN-PhO)-Ph | 3-(2-Me-PhO)-Ph | 5-PhO-2-pyrimidinyl |
| 2-MeS-Ph | 5-PhO-3-pyridinyl | 5-PhO-2-pyrimidinyl | 6-(2-NO₂-PhO)-4-pyrimidinyl |
| i-Bu | 6-Me-2-pyridinyl | 6-PhO-2-pyridinyl | 6-(2-Cl-PhO)-4-pyrimidinyl |
| 2-CF₃O-Ph | 3-CF₃O-Ph | 6-CF₃-2-pyridinyl | 6-(2-CF₃-PhO)-4-pyrimidinyl |
| 4-Me-Ph | 4-Br-Ph | 6-PhO-3-pyridinyl | 4,6-diMeO-2-pyrimidinyl |
| 4-Cl-Ph | 3-Et-Ph | 2-pyrimidinyl | 4,6-diMe-2-pyrimidinyl |
| 3-Me-Ph | 4-Et-Ph | 4-pyrimidinyl | 6-CF₃-4-pyrimidinyl |
| 3-CF₃-Ph | 4-MeO-Ph | 4-MeO-2-pyrimidinyl | 4-CF₃-2-pyridinyl |
| 3-Cl-2-Me-Ph | 4-t-Bu-Ph | 4-Me-2-pyrimidinyl | 4-CF₃-2-pyrimidinyl |
| 3-t-Bu-Ph | 4-CN-Ph | 6-MeO-4-pyrimidinyl | 2-pyridinyl |
| 3-NO₂-Ph | 4-NO₂-Ph | 2-Ph-4-thiazolyl | 6-CF₃-2-pyrazinyl |
| 3-F-Ph | 4-F-Ph | 3-MeO-6-pyridazinyl | 5-CF₃-3-pyridinyl |
| 4-CF₃-Ph | 3-Ph-Ph | 5-Me-2-furanyl | 3-MeO-2-pyridinyl |
| 3,4-diCl-Ph | 3,4-diMe-Ph | 2,5-diMe-3-thienyl | 5-CN-2-pyridinyl |
| 3,4-diCF₃-Ph | 3,5-diMe-Ph | 3-OCF₂H-Ph | 6-Me-2-pyridinyl |
| 3-EtO-Ph | 3-MeS-Ph | 4-OCF₂H-Ph | |

TABLE 17

Compounds of Formula I wherein: A = NMe, G = C, W = O, X = MeO,
R² = Me, R³ = R⁴ = H, the floating double bond is attached to G, and

| Z | Z | Z | Z |
|---|---|---|---|
| \multicolumn{4}{c}{Y = CH₂ON═C(CH₃).} | | | |

| Z | Z | Z | Z |
|---|---|---|---|
| hexyl | 4-octenyl | 3-pentynyl | 4-PhO-2-pyridinyl |
| PhO(CH₂)₃ | PhCH═CHCH₂ | PhC≡CCH₂ | (c-propyl)CH₂ |
| 2-Br-Ph | 2-Me-Ph | 2-Et-Ph | 6-(2-CN-PhO)-4-pyrimidinyl |
| 2-CN-Ph | 2-F-Ph | 2-Cl-Ph | 6-PhO-4-pyrimidinyl |
| 2,4-diCl-Ph | 2-Me-4-Cl-Ph | 2,4,6-triCl-Ph | 4-EtO-2-pyrimidinyl |
| 2-CF₃-Ph | 4-Ph-Ph | 3-PhO-Ph | 3-(4-pyrimidinyloxy)-Ph |
| 2-I-Ph | 3-(2-Cl-PhO)-Ph | 3-(2-Et-PhO)-Ph | 4-(2-thienyl)Ph |
| c-hexyl | 3,5-diCl-Ph | 6-Ph-2-pyridinyl | 3-(2-pyridinyloxy)Ph |
| 4-NO₂-Ph | 3,5-diCF₃-Ph | 6-PhO-4-pyridinyl | 3-pyridinyl |
| PhCH₂CH₂ | 2-MeO-Ph | 3-thienyloxy-Ph | 4-(3-Cl-2-pyridinyloxy)-Ph |
| (2-CN-Ph)CH₂ | 2,6-diMeO-Ph | 3-(4-CF₃-PhO)-Ph | 4-(PhO)-c-hexyl |
| CF₃CH₂ | 3-(2-CN-PhO)-Ph | 3-(2-Me-PhO)-Ph | 5-PhO-2-pyrimidinyl |
| 2-MeS-Ph | 5-PhO-3-pyridinyl | 5-PhO-2-pyrimidinyl | 6-(2-NO₂-PhO)-4-pyrimidinyl |
| i-Bu | 6-Me-2-pyridinyl | 6-PhO-2-pyridinyl | 6-(2-Cl-PhO)-4-pyrimidinyl |
| 2-CF₃O-Ph | 3-CF₃O-Ph | 6-CF₃-2-pyridinyl | 6-(2-CF₃-PhO)-4-pyrimidinyl |
| 4-Me-Ph | 4-Br-Ph | 6-PhO-3-pyridinyl | 4,6-diMeO-2-pyrimidinyl |
| 4-Cl-Ph | 3-Et-Ph | 2-pyrimidinyl | 4,6-diMe-2-pyrimidinyl |
| 3-Me-Ph | 4-Et-Ph | 4-pyrimidinyl | 6-CF₃-4-pyrimidinyl |
| 3-CF₃-Ph | 4-MeO-Ph | 4-MeO-2-pyrimidinyl | 4-CF₃-2-pyridinyl |
| 3-Cl-2-Me-Ph | 4-t-Bu-Ph | 4-Me-2-pyrimidinyl | 4-CF₃-2-pyrimidinyl |
| 3-t-Bu-Ph | 4-CN-Ph | 6-MeO-4-pyrimidinyl | 2-pyridinyl |
| 3-NO₂-Ph | 4-NO₂-Ph | 2-Ph-4-thiazolyl | 6-CF₃-2-pyrazinyl |
| 3-F-Ph | 4-F-Ph | 3-MeO-6-pyridazinyl | 5-CF₃-3-pyridinyl |
| 4-CF₃-Ph | 3-Ph-Ph | 5-Me-2-furanyl | 3-MeO-2-pyridinyl |
| 3,4-diCl-Ph | 3,4-diMe-Ph | 2,5-diMe-3-thienyl | 5-CN-2-pyridinyl |
| 3,4-diCF₃-Ph | 3,5-diMe-Ph | 3-OCF₂H-Ph | 6-Me-2-pyridinyl |
| 3-EtO-Ph | 3-MeS-Ph | 4-OCF₂H-Ph | |

TABLE 18

Compounds of Formula I wherein: A = N, G = N, W = O, X = MeO, $R^2$ = Me, $R^3$ = $R^4$ = H, the floating double bond is attached to A, and

| Z | Z | Z | Z |
|---|---|---|---|
| \multicolumn{4}{c}{Y = CH$_2$ON=C(CH$_3$).} | | | |

| Z | Z | Z | Z |
|---|---|---|---|
| hexyl | 4-octenyl | 3-pentynyl | 4-PhO-2-pyridinyl |
| PhO(CH$_2$)$_3$ | PhCH=CHCH$_2$ | PhC≡CCH$_2$ | (c-propyl)CH$_2$ |
| 2-Br-Ph | 2-Me-Ph | 2-Et-Ph | 6-(2-CN-PhO)-4-pyrimidinyl |
| 2-CN-Ph | 2-F-Ph | 2-Cl-Ph | 6-PhO-4-pyrimidinyl |
| 2,4-diCl-Ph | 2-Me-4-Cl-Ph | 2,4,6-triCl-Ph | 4-EtO-2-pyrimidinyl |
| 2-CF$_3$-Ph | 4-Ph-Ph | 3-PhO-Ph | 3-(4-pyrimidinyloxy)-Ph |
| 2-I-Ph | 3-(2-Cl-PhO)-Ph | 3-(2-Et-PhO)-Ph | 4-(2-thienyl)Ph |
| c-hexyl | 3,5-diCl-Ph | 6-Ph-2-pyridinyl | 3-(2-pyridinyloxy)Ph |
| 4-NO$_2$-Ph | 3,5-diCF$_3$-Ph | 6-PhO-4-pyridinyl | 3-pyridinyl |
| PhCH$_2$CH$_2$ | 2-MeO-Ph | 3-thienyloxy-Ph | 4-(3-Cl-2-pyridinyloxy)-Ph |
| (2-CN-Ph)CH$_2$ | 2,6-diMeO-Ph | 3-(4-CF$_3$-PhO)-Ph | 4-(PhO)-c-hexyl |
| CF$_3$CH$_2$ | 3-(2-CN-PhO)-Ph | 3-(2-Me-PhO)-Ph | 5-PhO-2-pyrimidinyl |
| 2-MeS-Ph | 5-PhO-3-pyridinyl | 5-PhO-2-pyridinyl | 6-(2-NO$_2$-PhO)-4-pyrimidinyl |
| i-Bu | 6-Me-2-pyridinyl | 6-PhO-2-pyridinyl | 6-(2-Cl-PhO)-4-pyrimidinyl |
| 2-CF$_3$O-Ph | 3-CF$_3$O-Ph | 6-CF$_3$-2-pyridinyl | 6-(2-CF$_3$-PhO)-4-pyrimidinyl |
| 4-Me-Ph | 4-Br-Ph | 6-PhO-3-pyridinyl | 4,6-diMeO-2-pyrimidinyl |
| 4-Cl-Ph | 3-Et-Ph | 2-pyrimidinyl | 4,6-diMe-2-pyrimidinyl |
| 3-Me-Ph | 4-Et-Ph | 4-pyrimidinyl | 6-CF$_3$-4-pyrimidinyl |
| 3-CF$_3$-Ph | 4-MeO-Ph | 4-MeO-2-pyrimidinyl | 4-CF$_3$-2-pyridinyl |
| 3-Cl-2-Me-Ph | 4-t-Bu-Ph | 4-Me-2-pyrimidinyl | 4-CF$_3$-2-pyrimidinyl |
| 3-t-Bu-Ph | 4-CN-Ph | 6-MeO-4-pyrimidinyl | 2-pyridinyl |
| 3-NO$_2$-Ph | 4-NO$_2$-Ph | 2-Ph-4-thiazolyl | 6-CF$_3$-2-pyrazinyl |
| 3-F-Ph | 4-F-Ph | 3-MeO-6-pyridazinyl | 5-CF$_3$-3-pyridinyl |
| 4-CF$_3$-Ph | 3-Ph-Ph | 5-Me-2-furanyl | 3-MeO-2-pyridinyl |
| 3,4-diCl-Ph | 3,4-diMe-Ph | 2,5-diMe-3-thienyl | 5-CN-2-pyridinyl |
| 3,4-diCF$_3$-Ph | 3,5-diMe-Ph | 3-OCF$_2$H-Ph | 6-Me-2-pyridinyl |
| 3-EtO-Ph | 3-MeS-Ph | 4-OCF$_2$H-Ph | |

Y = CH$_2$S.

| Z | Z | Z | Z |
|---|---|---|---|
| hexyl | 4-octenyl | 3-pentynyl | 4-PhO-2-pyridinyl |
| PhO(CH$_2$)$_3$ | PhCH=CHCH$_2$ | PhC≡CCH$_2$ | (c-propyl)CH$_2$ |
| 2-Br-Ph | 2-Me-Ph | 2-Et-Ph | 6-(2-CN-PhO)-4-pyrimidinyl |
| 2-CN-Ph | 2-F-Ph | 2-Cl-Ph | 6-PhO-4-pyrimidinyl |
| 2,4-diCl-Ph | 2-Me-4-Cl-Ph | 2,4,6-triCl-Ph | 4-EtO-2-pyrimidinyl |
| 2-CF$_3$-Ph | 4-Ph-Ph | 3-PhO-Ph | 3-(4-pyrimidinyloxy)-Ph |
| 2-I-Ph | 3-(2-Cl-PhO)-Ph | 3-(2-Et-PhO)-Ph | 4-(2-thienyl)Ph |
| c-hexyl | 3,5-diCl-Ph | 6-Ph-2-pyridinyl | 3-(2-pyridinyloxy)Ph |
| 4-NO$_2$-Ph | 3,5-diCF$_3$-Ph | 6-PhO-4-pyridinyl | 3-pyridinyl |
| PhCH$_2$CH$_2$ | 2-MeO-Ph | 3-thienyloxy-Ph | 4-(3-Cl-2-pyridinyloxy)-Ph |
| (2-CN-Ph)CH$_2$ | 2,6-diMeO-Ph | 3-(4-CF$_3$-PhO)-Ph | 4-(PhO)-c-hexyl |
| CF$_3$CH$_2$ | 3-(2-CN-PhO)-Ph | 3-(2-Me-PhO)-Ph | 5-PhO-2-pyrimidinyl |
| 2-MeS-Ph | 5-PhO-3-pyridinyl | 5-PhO-2-pyridinyl | 6-(2-NO$_2$-PhO)-4-pyrimidinyl |
| i-Bu | 6-Me-2-pyridinyl | 6-PhO-2-pyridinyl | 6-(2-Cl-PhO)-4-pyrimidinyl |
| 2-CF$_3$O-Ph | 3-CF$_3$O-Ph | 6-CF$_3$-2-pyridinyl | 6-(2-CF$_3$-PhO)-4-pyrimidinyl |
| 4-Me-Ph | 4-Br-Ph | 6-PhO-3-pyridinyl | 4,6-diMeO-2-pyrimidinyl |
| 4-Cl-Ph | 3-Et-Ph | 2-pyrimidinyl | 4,6-diMe-2-pyrimidinyl |
| 3-Me-Ph | 4-Et-Ph | 4-pyrimidinyl | 6-CF$_3$-4-pyrimidinyl |
| 3-CF$_3$-Ph | 4-MeO-Ph | 4-MeO-2-pyrimidinyl | 4-CF$_3$-2-pyridinyl |
| 3-Cl-2-Me-Ph | 4-t-Bu-Ph | 4-Me-2-pyrimidinyl | 4-CF$_3$-2-pyrimidinyl |
| 3-t-Bu-Ph | 4-CN-Ph | 6-MeO-4-pyrimidinyl | 2-pyridinyl |
| 3-NO$_2$-Ph | 4-NO$_2$-Ph | 2-Ph-4-thiazolyl | 6-CF$_3$-2-pyrazinyl |
| 3-F-Ph | 4-F-Ph | 3-MeO-6-pyridazinyl | 5-CF$_3$-3-pyridinyl |
| 4-CF$_3$-Ph | 3-Ph-Ph | 5-Me-2-furanyl | 3-MeO-2-pyridinyl |
| 3,4-diCl-Ph | 3,4-diMe-Ph | 2,5-diMe-3-thienyl | 5-CN-2-pyridinyl |
| 3,4-diCF$_3$-Ph | 3,5-diMe-Ph | 3-OCF$_2$H-Ph | 6-Me-2-pyridinyl |
| 3-EtO-Ph | 3-MeS-Ph | 4-OCF$_2$H-Ph | |

TABLE 19

Compounds of Formula I wherein: A = N, G = N, W = O, X = MeO, R² = Me, R³ = R⁴ = H, the floating double bond is attached to A, and

| Z | Z | Z | Z |
|---|---|---|---|
| Y = CH₂ON=C(H). | | | |
| 2-Me-Ph | 3-Me-Ph | 3-CF₃-Ph | 3-Cl-Ph |
| 4-Cl-Ph | 4-CF₃-Ph | 2,5-diMe-Ph | 3,5-diCl-Ph |

TABLE 20

Compounds of Formula I wherein: A = N, G = N, W = O, X = MeO, Z = 3-CF₃-Ph, R² = Me, R³ = R⁴ = H, the floating double bond is attached to A, and

| R⁷ | R⁷ | R⁷ | R⁷ |
|---|---|---|---|
| Y = CH₂ON=C(R⁷). | | | |
| CF₃ | OCH₂CF₃ | Et | n-Pr |
| Cl | MeO | EtO | MeS |

TABLE 21

Compounds of Formula I wherein: A = O, G = C, W = O, X = MeO, R³ = R⁴ = H, Y = CH₂ON=C(R⁷), the floating double bond is attached to G, and

| R⁷ | Z | R⁷ | Z |
|---|---|---|---|
| R² = Me | | | |
| c-propyl | 3,4-(OCH₂CH₂O)-Ph | c-propyl | 3,4-(OCHFCF₂O)-Ph |
| c-propyl | 3,4-(OCF₂O)-Ph | c-propyl | Ph |
| c-propyl | 4-CF₃-Ph | c-propyl | 3-CF₃-Ph |
| c-propyl | 4-Cl-Ph | c-propyl | 3-Cl-Ph |
| c-propyl | 2-Me-Ph | c-propyl | 3-OCF₃-Ph |
| CF₃ | 3,4-(OCH₂CH₂O)-Ph | CF₃ | 3,4-(OCHFCF₂O)-Ph |
| CF₃ | 3,4-(OCF₂O)-Ph | CF₃ | Ph |
| CF₃ | 4-CF₃-Ph | CF₃ | 3-CF₃-Ph |
| CF₃ | 4-Cl-Ph | CF₃ | 3-Cl-Ph |
| CF₃ | 2-Me-Ph | CF₃ | 3-OCF₃-Ph |
| Et | 3,4-(OCH₂CH₂O)-Ph | Et | 3,4-(OCHFCF₂O)-Ph |
| Et | 3,4-(OCF₂O)-Ph | Et | Ph |
| Et | 4-CF₃-Ph | Et | 3-CF₃-Ph |
| Et | 4-Cl-Ph | Et | 3-Cl-Ph |
| Et | 2-Me-Ph | Et | 3-OCF₃-Ph |

TABLE 22

Compounds of Formula I wherein: A = NMe, G = C, W = O, X = MeO, R³ = R⁴ = H, Y = CH₂ON=C(R⁷), the floating double bond is attached to G, and

| R⁷ | Z | R⁷ | Z |
|---|---|---|---|
| R² = Me | | | |
| c-propyl | 3,4-(OCH₂CH₂O)-Ph | c-propyl | 3,4-(OCHFCF₂O)-Ph |
| c-propyl | 3,4-(OCF₂O)-Ph | c-propyl | Ph |
| c-propyl | 4-CF₃-Ph | c-propyl | 3-CF₃-Ph |
| c-propyl | 4-Cl-Ph | c-propyl | 3-Cl-Ph |
| c-propyl | 2-Me-Ph | c-propyl | 3-OCF₃-Ph |
| CF₃ | 3,4-(OCH₂CH₂O)-Ph | CF₃ | 3,4-(OCHFCF₂O)-Ph |
| CF₃ | 3,4-(OCF₂O)-Ph | CF₃ | Ph |
| CF₃ | 4-CF₃-Ph | CF₃ | 3-CF₃-Ph |
| CF₃ | 4-Cl-Ph | CF₃ | 3-Cl-Ph |
| CF₃ | 2-Me-Ph | CF₃ | 3-OCF₃-Ph |
| Et | 3,4-(OCH₂CH₂O)-Ph | Et | 3,4-(OCHFCF₂O)-Ph |
| Et | 3,4-(OCF₂O)-Ph | Et | Ph |
| Et | 4-CF₃-Ph | Et | 3-CF₃-Ph |

TABLE 22-continued

Compounds of Formula I wherein: A = NMe, G = C, W = O, X = MeO, R³ = R⁴ = H, Y = CH₂ON=C(R⁷), the floating double bond is attached to G, and

| R⁷ | Z | R⁷ | Z |
|---|---|---|---|
| Et | 4-Cl-Ph | Et | 3-Cl-Ph |
| Et | 2-Me-Ph | Et | 3-OCF₃-Ph |

TABLE 23

Compounds of Formula I wherein: A = N, G = N, W = O, X = MeO, R³ = R⁴ = H, Y = CH₂ON=C(R⁷), the floating double bond is attached to A, and

| R⁷ | Z | R⁷ | Z |
|---|---|---|---|
| R² = Me | | | |
| c-propyl | 3,4-(OCH₂CH₂O)-Ph | c-propyl | 3,4-(OCHFCF₂O)-Ph |
| c-propyl | 3,4-(OCF₂O)-Ph | c-propyl | Ph |
| c-propyl | 4-CF₃-Ph | c-propyl | 3-CF₃-Ph |
| c-propyl | 4-Cl-Ph | c-propyl | 3-Cl-Ph |
| c-propyl | 2-Me-Ph | c-propyl | 3-OCF₃-Ph |
| CF₃ | 3,4-(OCH₂CH₂O)-Ph | CF₃ | 3,4-(OCHFCF₂O)-Ph |
| CF₃ | 3,4-(OCF₂O)-Ph | CF₃ | Ph |
| CF₃ | 4-CF₃-Ph | CF₃ | 3-CF₃-Ph |
| CF₃ | 4-Cl-Ph | CF₃ | 3-Cl-Ph |
| CF₃ | 2-Me-Ph | CF₃ | 3-OCF₃-Ph |
| Et | 3,4-(OCH₂CH₂O)-Ph | Et | 3,4-(OCHFCF₂O)-Ph |
| Et | 3,4-(OCF₂O)-Ph | Et | Ph |
| Et | 4-CF₃-Ph | Et | 3-CF₃-Ph |
| Et | 4-Cl-Ph | Et | 3-Cl-Ph |
| Et | 2-Me-Ph | Et | 3-OCF₃-Ph |

TABLE 24

Compounds of Formula I wherein: A = O, G = C, W = O, X = MeO, R³ = R⁴ = H, the floating double bond is attached to G, and R² = Me

| Y—Z | Y—Z | Y—Z |
|---|---|---|
| —ON= (cyclopentane fused benzene, F substituent) | —ON= (cyclopentane fused benzene, CF₃ substituent) | —ON= (cyclopentane fused benzene, Cl substituent) |
| —ON= (cyclohexane fused benzene, F substituent) | —ON= (cyclohexane fused benzene, CF₃ substituent) | —ON= (pyran fused benzene, O, F substituent) |

TABLE 24-continued

Compounds of Formula I wherein: A = O, G = C, W = O, X = MeO, $R^3 = R^4 = H$, the floating double bond is attached to G, and $R^2 = Me$

| Y—Z | Y—Z | Y—Z |
|---|---|---|

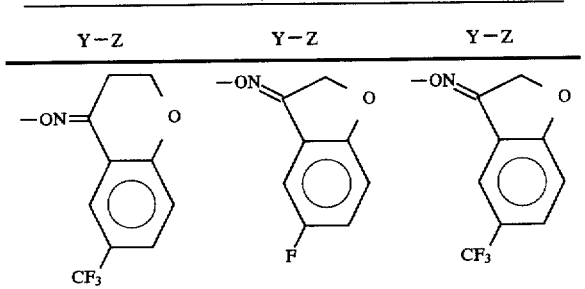

TABLE 25

Compounds of Formula I wherein: A = NMe, G = C, W = O, X = MeO, $R^3 = R^4 = H$, the floating double bond is attached to G, and $R^2 = Me$

| Y—Z | Y—Z | Y—Z |
|---|---|---|

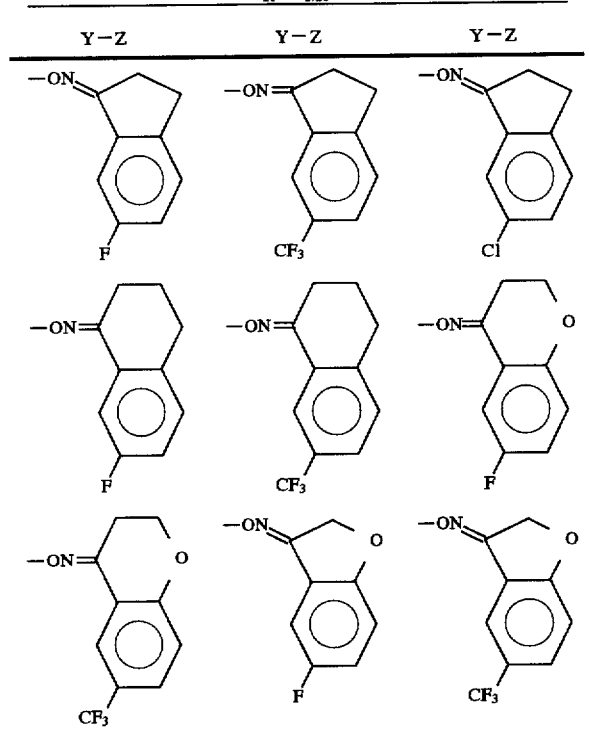

TABLE 26

Compounds of Formula I wherein: A = N, G = N, W = O, X = MeO, $R^3 = R^4 = H$, the floating double bond is attached to A, and $R^2 = Me$

| Y—Z | Y—Z | Y—Z |
|---|---|---|

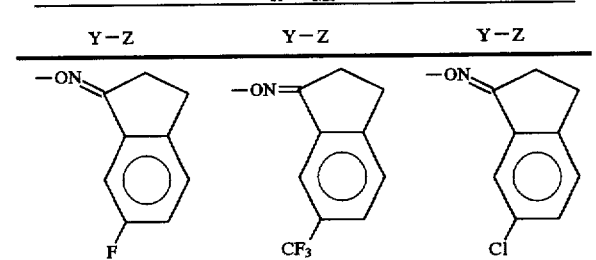

TABLE 26-continued

Compounds of Formula I wherein: A = N, G = N, W = O, X = MeO, $R^3 = R^4 = H$, the floating double bond is attached to A, and $R^2 = Me$

| Y—Z | Y—Z | Y—Z |
|---|---|---|

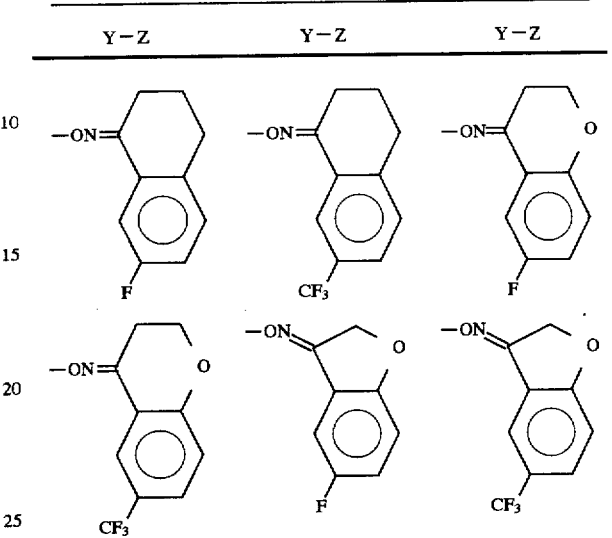

Formulation/Utility

Compounds of this invention will generally be used in formulation with an agriculturally suitable composition. The fungicidal compositions of the present invention comprise an effective amount of at least one compound of Formula I as defined above and at least one of (a) a surfactant, (b) an organic solvent, and (c) at least one solid or liquid diluent. Useful formulations can be prepared in conventional ways. They include dusts, granules, pellets, solutions, suspensions, emulsions, wettable powders, emulsifiable concentrates, dry flowables and the like. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up to 100 weight percent.

|  | Weight Percent | | |
|---|---|---|---|
|  | Active Ingredient | Diluent | Surfactant |
| Wettable Powders | 5–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents and solvents are described in Marsden, *Solvents Guide*, 2nd Ed., Interscience, New York. (1950). *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, (1964), list surfactants and recommended uses. All formulations can contain minor amounts of additives to reduce foam, caking, corrosion, microbiological growth, and the like.

Methods for formulating such compositions are well known. Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., *Pesticide Formulations*, Washington, D.C., (1988), pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering*, Dec. 4, 1967,pp 147–148, *Perry's Chemical Engineer's Handbook*, 4th Ed., McGraw-Hill, New York, (1963), pp 8 –57 and following, and WO 91/13546. Pellets can be prepared as described in U.S. Pat. No. 4,172,714. Water-dispersible and water-soluble granules can be prepared as taught in DE 3,246,493.

For further information regarding the art of formulation, see U.S. Pat. No. 3,235,361, Col. 6, line 16 through Col. 7, line 19 and Examples 10 through 41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S Pat. No. 2,891,855, Col. 3, line 66 through Col. 5, line 17 and Examples 1–4; Klingman, *Weed Control as a Science*, John Wiley and Sons, Inc., New York, (1961), pp 81–96; and Hance et al., *Weed Control Handbook*, 8th Ed., Blackwell Scientific Publications, Oxford, (1989).

In the following Examples, all percentages are by weight and all formulations are prepared in conventional ways. Compound 1 refers to the compound in Index Table A hereinafter.

Example A

| Wettable Powder | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

| Granule | |
|---|---|
| Compound 1 | 10.0% |
| attapulgite granules (low volative matter, 0.71/0.30 mm; U.S.S. No. 25–50 sieves) | 90.0%. |

Example C

| Extruded Pellet | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

| Emulsifiable Concentrate | |
|---|---|
| Compound 1 | 20.0% |
| blend of oil soluble sulfonates and polyoxyethylene ethers | 10.0% |
| isophorone | 70.0%. |

The compounds of this invention are useful as plant disease control agents. The present invention therefore further comprises a method for controlling plant diseases caused by fungal plant pathogens comprising applying to the plant or portion thereof, or to the plant seed or seedling, an effective amount of a compound of Formula I or a fungicidal composition containing said compound. The compounds and compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, vegetable, field, cereal, and fruit crops. These pathogens include *Plasmopara viticola, Phytophthora infestans, Peronospora tabacina, Pseudoperonospora cubensis, Pythium aphanidermatum, Alternaria brassicae, Septoria nodorum, Cercosporidium personatum, Cercospora arachidicola, Pseudocercosporella herpotrichoides, Cercospora beticola, Botrytis cinerea, Monilinia fructicola, Pyricularia oryzae, Podosphaera leucotricha, Venturia inaequalis, Erysiphe graminis, Uncinula necatur, Puccinia recondita, Puccinia graminis, Hemileia vastatrix, Puccinia striiformis, Puccinia arachidis, Rhizoctonia solani, Sphaerotheca fuiginea, Fusarium oxysporum, Verticillium dahliae, Pythium aphaniderniatum, Phytophthora megasperma* and other generea and species closely related to these pathogens.

Compounds of this invention can also be mixed with one or more other insecticides, fungicides, nematocides, bactericides, acaricides, semiochemicals, repellants, attractants, pheromones, feeding stimulants or other biologically active compounds to form a multi-component pesticide giving an even broader spectrum of agricultural protection. Examples of other agricultural protectants with which compounds of this invention can be formulated are: insecticides such as acephate, avermectin B, azinphosmethyl, bifenthrin, biphenate, buprofezin, carbofuran, chlordimeform, chlorpyrifos, cyfluthrin, deltamethrin, diazinon, diflubenzuron, dimethoate, esfenvalerate, fenpropathrin, fenvalerate, fipronil, flucythrinate, flufenprox, fluvalinate, fonophos, isofenphos, malathion, metaldehyde, methamidophos, methidathion, methomyl, methoprene, methoxychlor, monocrotophos, oxamyl, parathion-methyl, permethrin, phorate, phosalone, phosmet, phosphamidon, pirimicarb, profenofos, rotenone, sulprofos, terbufos, tetrachlorvinphos, thiodicarb, tralomethrin, trichlorfon and trifumuron; fungicides such as benomyl, blasticidin S, bromuconazole, captafol, captan, carbendazim, chloroneb, chlorothalonil, copper oxychloride, copper salts, cymoxanil, cyproconazole, dichloran, diclobutrazol, diclomezine, difenoconazole, diniconazole, dodine, edifenphos, epoxyconazole fenarimol, fenbuconazole, fenpropidine, fenpropimorph, fluquinconazole, flusilazol, flutolanil, flutriafol, folpet, furalaxyl, hexaconazole, ipconazole, iprobenfos, iprodione, isoprothiolane, kasugamycin, mancozeb, maneb, mepronil, metalaxyl, metconazole, myclobutanil, neo-asozin, oxadixyl, penconazole, pencycuron, phosethyl-Al, probenazole, prochloraz, propiconazole, pyrifenox, pyroquilon, sulfur, tebuconazole, tetraconazole, thiabendazole, thiophanate-methyl, thiuram, triadimefon, triadimenol, tricyclazole, uniconzole, validamnycin and vinclozolin; nematocides such as aldoxycarb, fenamiphos and fosthietan; bactericides such as oxytetracyline, streptomycin and tribasic copper sulfate; acaricides such as amitraz, binapacryl, chlorobenzilate, cyhexatin, dicofol, dienochlor, fenbutatin oxide, hexythiazox, oxythioquinox, propargite and tebufenpyrad; and biological agents such as Bacillus thuringiensis and baculovirus.

In certain instances, combinations with other fungicides having a similiar spectrum of control but a different mode of action will be particularly advantageous for resistance management.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to the seed to protect the seed and seedling.

Rates of application for these compounds can be influenced by many factors of the environment and should be determined under actual use conditions. Foliage can normally be protected when treated at a rate of from less than 1 g/ha to 5,000 g/ha of active ingredient. Seed and seedlings can normally be protected when seed is treated at a rate of from 0.1 to 10 g per kilogram of seed.

The following TESTS demonstrate the control efficacy of compounds of this invention on specific pathogens. The pathogen control protection afforded by the compounds is not limited, however, to these species. See Index Tables A–D for compound descriptions.

Test compounds were first dissolved in acetone in an amount equal to 3% of the final volume and then suspended at a concentration of 200 ppm in purified water containing 250 ppm of the surfactant Trem® 014 (polyhydric alcohol esters). The resulting test suspensions were then used in the following tests.

TEST A

The test suspension was sprayed to the point of run-off on wheat seedlings. The following day the seedlings were inoculated with a spore dust of *Erysiphe graminis f. sp. tritici*, (the causal agent of wheat powdery mildew) and incubated in a growth chamber at 20° C. for 7 days, after which disease ratings were made.

TEST B

The test suspension was sprayed to the point of run-off on wheat seedlings. The following day the seedlings were inoculated with a spore suspension of *Puccinia recondita* (the causal agent of wheat leaf rust) and incubated in a saturated atmosphere at 20° C. for 24 h, and then moved to a growth chamber at 20° C. for 6 days, after which disease ratings were made.

TEST C

The test suspension was sprayed to the point of run-off on rice seedlings. The following day the seedlings were inoculated with a spore suspension of *Pyricularia oryzae* (the causal agent of rice blast) and incubated in a saturated atmosphere at 27° C. for 24 h, and then moved to a growth chamber at 30° C. for 5 days, after which disease ratings were made.

TEST D

The test suspension was sprayed to the point of run-off on tomato seedlings. The following day the seedlings were inoculated with a spore suspension of *Phytophthora infestans* (the causal agent of potato and tomato late blight) and incubated in a saturated atmosphere at 20° C. for 24 h, and then moved to a growth chamber at 20° C. for 5 days, after which disease ratings were made.

TEST E

The test suspension was sprayed to the point of run-off on grape seedlings. The following day the seedlings were inoculated with a spore suspension of *Plasmopara viticola* (the causal agent of grape downy mildew) and incubated in a saturated atmosphere at 20° C. for 24 h, moved to a growth chamber at 20° C. for 6 days,and then incubated in a saturated atmosphere at 20° C. for 24 h, after which disease ratings were made.

TEST F

The test suspension was sprayed to the point of run-off on cucumber seedlings. The following day the seedlings were inoculated with a spore suspension of *Botrytis cinerea* (the causal agent of gray mold on many crops) and incubated in a saturated atmospere at 20° C. for 48 h, and moved to a growth chamber at 20° C. for 5 days, after which disease ratings were made.

INDEX TABLE A

| Compound | m.p. (°C.) |
| --- | --- |
| 1 | 117–120 |

INDEX TABLE B

| Compound | Y | Z | m.p. (°C.) |
| --- | --- | --- | --- |
| 2 | O | 2-MeO—Ph | oil* |
| 3 | O | $CH_2$—Ph | oil* |
| 4 | — | Me | oil* |
| 5 | $CH_2O$ | 2-Me—Ph | oil* |

*See Index Table D for $^1H$ NMR data.

INDEX TABLE C

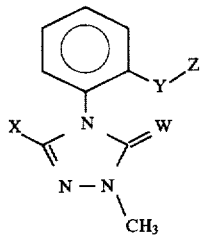

| Compound | W | X | Y | Z | m.p. (°C.) |
|---|---|---|---|---|---|
| 6 | O | MeS | O | Ph | 129–130 |
| 7 | O | MeO | O | Me | 123–126 |
| 8 | O | MeO | — | Me | 95–97 |
| 9 | O | MeS | — | Me | 95–97 |
| 10 | O | Cl | — | Me | 99–100 |
| 11 | O | MeO | O | Ph | 88–91 |
| 12 | O | Cl | CH$_2$O | 2-Me—Ph | 88–96 |
| 13 | O | MeO | CH$_2$O | 2-Me—Ph | 110–113 |
| 14 | O | EtO | CH$_2$O | 2-Me—Ph | oil* |
| 15 | O | MeS | CH$_2$O | 2-Me—Ph | 80–88 |
| 16 | O | OCH$_2$C≡CH | CH$_2$O | 2-Me—Ph | 122–130 |
| 17 | O | Cl | CH$_2$ON=C(Me) | 4-Me—Ph | oil* |
| 18 | O | MeO | CH$_2$ON=C(Me) | 4-Me—Ph | 116–118 |
| 19 | O | MeS | CH$_2$ON=C(Me) | 4-Me—Ph | oil* |
| 20 | O | Cl | CH$_2$O—N=(indanyl) | | oil |
| 21 | S | MeS | O | Ph | oil* |
| 22 | O | MeO | CH$_2$O—N=(indanyl) | | 126–130 |
| 23 | O | Cl | CH$_2$ON=C(H) | Ph | oil* |
| 24 | O | MeS | CH$_2$O—N=(indanyl) | | oil* |
| 25 | O | Cl | CH$_2$O | 3-(OPh)—Ph | oil* |
| 26 | O | MeO | CH$_2$O | 3-(OPh)—Ph | oil* |
| 27 | O | MeO | CH$_2$ON=C(H) | Ph | 101–104 |
| 28 | O | MeS | CH$_2$O | 3-(OPh)—Ph | 95–100 |
| 29 | O | Cl | CH$_2$S | 2-Me—Ph | 106–109 |
| 30 | O | MeO | CH$_2$S | 2-Me—Ph | 115–118 |
| 31 | O | MeS | CH$_2$S | 2-Me—Ph | 82–86 |
| 32 | O | Cl | CH$_2$S | 2-benzthiazolyl | 95–97 |
| 33 | O | MeO | C≡C | Ph | 164–166 |
| 34 | O | MeO | CH$_2$ON=C(Me) | 4-Br—Ph | 115–120 |
| 35 | O | Cl | CH$_2$ON=C(Me) | 4-Br—Ph | gum* |
| 36 | O | Cl | CH$_2$O | 3-(benzoyl)-Ph | oil* |
| 37 | O | MeS | CH$_2$ON=C(Me) | 4-Br—Ph | 117–122 |
| 38 | O | MeO | CH$_2$O | 3-(benzoyl)-Ph | oil* |
| 39 | O | Cl | CH=NOCH$_2$ | 4-Cl—Ph | oil* |
| 40 | O | Cl | CH$_2$ON=C(Me) | 1,3-benzodioxol-5-yl | oil* |
| 41 | O | MeO | CH=NOCH$_2$ | 4-Cl—Ph | oil* |
| 42 | O | MeO | CH$_2$ON=C(Me) | 1,3-benzodioxol-5-yl | oil* |
| 43 | O | Cl | O | 4-(6-PhO)-4-pyrimidine | oil* |

INDEX TABLE C-continued

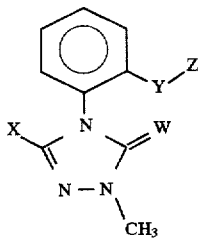

| Compound | W | X | Y | Z | m.p. (°C.) |
|---|---|---|---|---|---|
| 44 | O | MeO | CH$_2$S | 2-benzthiazolyl | 95–97 |
| 45 | O | MeO | CH$_2$ON=C(Me) | 2-Me—Ph | oil* |
| 46 | O | MeO | CH$_2$ON=C(Me) | 4-CF$_3$—Ph | 138–144 |
| 47 | O | MeO | CH$_2$ON=C(Me) | Ph | oil* |
| 48 | O | MeO | CH$_2$ON=C(Me) | Ph | oil* |
| 49 | O | MeO | CH$_2$ON=C(CF$_3$) | 3-Me—Ph | oil* |
| 50 | O | MeO | CH$_2$ON=C(Me) | 4-MeO—Ph | oil* |
| 51 | O | MeO | CH$_2$ON=C(Me) | 3-Cl—Ph | oil* |
| 52 | O | MeO | CH=NOCH(Me) | Ph | oil* |
| 53 | O | MeO | CH=NOCH$_2$ | 2-Me—Ph | oil* |

*See Index Table D for $^1$H NMR data.

INDEX TABLE D

| Cmpd. No. | $^1$H NMR Data (200 MHz, CDCl$_3$ solution) |
|---|---|
| 2 | δ 7.51(dd, 1H), 7.27(dt, 1H), 7.17(m, 2H), 6.97(dd, 1h), 6.6(m, 3H), 3.92(s, 3H), 3.74(s, 3H), 3.33(s, 3H) |
| 3 | δ 7.32(m, 7H), 6.99(m, 2H), 5.0*(s, 2H), 3.84(s, 3H), 3.42(s, 3H) |
| 4 | δ 7.25(m, 4H), 3.98(s, 3H), 3.45(s, 3H), 2.30(s, 3H) |
| 5 | δ 7.61(d, 1H), 78,35(m, 3H), 7.11(m, 2H), 6.84(t, 2H), 5.12(s, 2H), 3.96(s, 3H), 3.4156(s, 3H), 2.24(s, 3H) |
| 14 | δ (7.65(d, 1H), 7.45(m, 2H), 7.23(m, 1H), 7.10(m, 2H), 6.82(t, 1H), 6.78(d, 1H), 5.08(s, 2H), 4.29(m, 2H), 3.41(s, 3H), 2.24(s,3H), 1.31(t, 3H) |
| 17 | δ 7.6–7.45(m, 5H), 7.20(m, 1H), 7.14(d, 2H), 5.27(d, 1H), 5.16(d, 1H), 3.46(s, 3H), 2.34(s, 3H), 2.16(s, 3H) |
| 19 | δ 7.6(d, 1H), 7.5(m, 3H), 7.4(t, 1H), 7.25(m, 1H), 7.15(d, 2H), 5.26(d, 1H), 5.20(d, 1H), 3.48(s, 3H), 2.41(s, 3H), 2.43(s, 3H), 2.18(s, 3H) |
| 20 | δ 7.62(m, 2H), 7.5(m, 2H), 7.35–7.2(m, 4H), 5.25(d, 1H), 5.15(d, 1H), 3.48(s, 3H), 3.02(m, 2H), 2.85(m, 2H) |
| 21 | δ 7.42(m, 2H), 7.10(m, 1H), 7.06(m, 3H), 6.99(t, 1H), 6.68(d, 2H), 3.37(s, 3H), 2.51(s, 3H) |
| 23 | δ 8.01(s, 1H), 7.61(d, 1H), 7.52(m, 4H), 7.35(m, 3H), 7.25(d, 1H), 5.23(d, 1H), 5.15(d, 1H), 3.49(s, 3H) |
| 24 | δ 7.6(m, 2H), 7.5–7.4(m, 3H), 7.3–7.2(m, 3H), 5.24(d, 1H), 5.20(d, 1H), 3.48(s, 3H), 2.40(s, 3H) |
| 25 | δ 7.6–7.4(m, 4H), 7.35(m, 2H), 7.2(m, 2H), 7.0(d, 2H), 6.6(m, 3H), 5.04(d, 1H), 5.00(d, 1H), 3.45(s, 3H) |
| 26 | δ 7.6(d, 1H), 7.45(m, 2H), 7.33(t, 2H), 7.19(m, 2H), 7.10(t, 1H), 7.01(d, 2H), 6.6(m, 3H), 5.03(m, 2H), 3.87(s, 3H), 3.39(s, 3H) |
| 35 | δ 7.6–7.4(m, 7H), 7.23(d, 1H), 5.28(d, 1H), 5.17(d, 1H), 3.46(s, 3H), 2.14(s, 3H) |
| 36 | δ 7.80(d, 2H), 7.65–7.45(m, 6H), 7.35(d, 2H), 7.30(m, 1H), 7.25(m, 1H), 7.10(t, 1H), 5.15(d, 1H), 5.10(d, 1H), 3.45(s, 2H) |
| 38 | δ 7.77(d, 2H), 7.6(m, 2H), 7.47(m, 4H), 7.35(m, 3H), 7.25(m, 1H), 7.10(m, 1H), 5.13(d, 1H), 5.12(d, 1H), 3.89(s, 3H), 3.38(s, 3H) |
| 39 | δ 8.03(s, 1H), 7.70(d, 1H), 7.53(m, 2H), 7.35–7.25(m, 5H), 5.06(s, 2H), 3.46(s, 3H) |
| 40 | δ 7.6–7.5(m, 3H), 7.24(m, 1H), 7.13(s, 1H), 7.02(d, 1H), 6.78(d, 1H), 5.96(s, 2H), 5.26(d, 1H), 5.14(d, 1H), 3.48(s, 3H), 2.13(s, 3H) |
| 41 | δ 8.04(s, 1H), 7.8(m, 1H), 7.45(m, 2H) 7.35–7.25(m, 5H), 5.10(s, 2H), 3.86(s, 3H), 3.41(m, 3H) |
| 42 | δ 7.58(m, 1H), 7.43(m, 2H), 7.25(m, 1H), 7.15(m, 1H), 7.02(d, 1H), 6.76(d, 1H), 5.96(s, 2H), 5.22(d, 1H), 5.18(d, 1H) 3.89(s, 3H), 3.42(s, 3H), 2.15(s, 3H) |
| 43 | δ 8.40(s, 1H), 7.6(m, 1H), 7.5–7.4(m, 5H), 7.3(d, 1H), 7.18(m, 2H), 6.38(s, 1H), 3.45(s, 3H) |
| 45 | δ 7.55(d, 1H), 7.40(m, 3H), 7.20(m, 4H), 5.21(d, 1H), 3.87(s, 3H), 3.42(s, 3H), 2.24(s, 3H) |
| 47 | δ 7.6–7.2(m, 9H), 5.4–5.2(m, 2H), 3.87, 3.83(s, 3H), 3.41, 3.40(s, 3H) |
| 48 | δ 7.6(m, 3H), 7.44(m, 2H), 7.35(m, 3H), 7.25(m, 1H), 5.26(d, 1H), 5.22(d, 1H), 3.88(s, 3H), 3.49(s, 3H), 2.20(s, 3H) |

INDEX TABLE D

| Cmpd. No. | $^1$H NMR Data (200 MHz, CDCl$_3$ solution) |
|---|---|
| 49 | δ 7.5(d, 1H0, 7.40(m, 4H), 7.23(m, 2H), 7.18(d, 1H), 5.26(d, 1H), 5.21(d, 1H), 3.88(s, 3H) 3.41(s, 3H), 2.36(s, 3H), 2.19(s,3H) |
| 50 | δ 7.56(m, 3H), 7.45(m, 2H), 7.25(m, 1H), 6.86(d, 2H), 5.24 (d, 1H), 5.19(d, 1H), 3.88(s, 3H), 3.81(s, 3H), 3,41(s, 3H), 2.17(s, 3H) |
| 51 | δ 7.5(m, 2H), 7.45(m, 3H), 7.3(m, 3H), 5.27(d, 1H), 5.22(d, 1H), 389(s, 3H) |
| 52 | δ 8.02, 8.01(s, 1H), 7.8, 7.7(m, 1H), 7.45(m, 2H), 7.35(m, 4H), 7.25(m, 2H), 5.25 (m, 1H), 3.88, 7.74(s, 3H), 3.45, 3.39(s, 3H), 1.62-1.56(m, 3H) |
| 53 | δ 8.04(s, 1H), 7.81(m, 1H), 7.45(m, 2H), 7.38–7.18(m, 5H), 5.18(s, 2H), 3.86(s, 3H), 3.42(s, 3H), 2.38(s, 3H) |

Results for Tests A–F are given in Table 1. In the table, a rating of 100 indicates 100% disease control and a rating of 0 indicates no disease control (relative to the controls).

TABLE 1

| Cmpd. No. | Test A | Test B | Test C | Test D | Test E | Test F |
|---|---|---|---|---|---|---|
| 1 | 57 | 79 | 0 | 0 | 17 | 68 |
| 2 | 86 | 93 | 0 | 0 | 100 | 0 |
| 3 | 57 | 79 | 0 | 61 | 100 | 68 |
| 4 | 0 | 0 | 0 | 0 | 100 | 0 |
| 5 | 99 | 100 | 0 | 46 | 100 | 43 |
| 6 | 98 | 100 | 36 | 85 | 100 | 42 |
| 7 | 73 | 9 | 0 | 33 | 5 | 3 |
| 8 | 0 | 0 | 0 | 0 | 35 | 46 |
| 9 | 0 | 0 | 0 | 0 | 35 | 0 |
| 10 | 35 | 3 | 0 | 43 | 78 | 0 |
| 11 | 100 | 100 | 0 | 64 | 100 | 50 |
| 12 | 95 | 97 | 0 | 47 | 92 | 71 |
| 13 | 98 | 100 | 0 | 0 | 69* | 63 |
| 14 | 78 | 81 | 0 | 0 | 0 | 0 |
| 15 | 100 | 100 | 0 | 63 | 100 | 36 |
| 16 | 92 | 57 | 0 | 0 | 0 | 0 |
| 17 | 78 | 91 | 0 | 0 | 36 | 44 |
| 18 | 52 | 0 | 0 | 0 | 0 | 0 |
| 19 | 0 | 0 | 0 | 0 | 0 | 62 |
| 20 | 63 | 84 | 0 | 26 | 99 | 65 |
| 21 | — | — | 0 | — | — | — |
| 22 | 38 | 100 | 0 | 47 | 100 | 47 |
| 23 | 38 | 89 | 0 | 0 | 100 | 0 |
| 24 | 0 | 98 | 97 | 47 | 100 | 70 |
| 25 | 0 | 84 | 88 | 16 | 100 | 0 |
| 26 | 72 | 100 | 0 | 73 | 100 | 44 |
| 27 | 72 | 93 | 0 | 16 | 100 | 2 |
| 28 | 83 | 97 | 19 | 59 | 100 | 0 |
| 29 | 16 | 97 | 0 | 25 | 8 | 0 |
| 30 | 95 | 96 | 0 | 47 | 100 | 47 |
| 31 | 89 | 99 | 0 | 46 | 100 | 0 |
| 32 | 60 | 53 | 0 | 0 | 100 | 47 |
| 33 | 95 | 98 | 0 | 77 | 100 | 0 |
| 34 | 90 | 100 | 88 | 64 | 100 | 0 |
| 35 | 0 | 97 | 0 | 0 | 99 | 9 |
| 36 | 63 | 93 | 62 | 46 | 100 | 0 |
| 37 | 98 | 100 | 93 | 63 | 100 | 48 |
| 38 | 0 | 99 | 73 | 26 | 100 | 0 |
| 39 | 32 | 85 | 73 | 0 | 45 | 0 |
| 40 | 59 | 97 | 93 | 0 | 76 | 49 |
| 41 | 97 | 100 | 0 | 0 | 100 | 0 |
| 42 | 92 | 100 | 62 | 64 | 100 | 68 |
| 43 | 97 | 99 | 50 | 26 | 97 | 0 |
| 44 | 73 | 100 | 0 | 47 | 100 | 69 |
| 45 | 94 | 100 | 0 | 0 | 100 | 47 |
| 46 | 100 | 100 | 100 | 93 | 100 | 0 |
| 47 | 96 | 100 | 0 | 0 | 100 | 0 |
| 48 | 100 | 100 | 0 | 47 | 100 | 0 |
| 49 | 100 | 100 | 88 | 86 | 100 | 47 |
| 50 | 92 | 100 | 97 | 77 | — | 45 |
| 51 | 100 | 100 | 100 | 97 | — | 89 |

*Tested at 40 ppm.

What is claimed is:

1. A compound selected from Formula I, and agriculturally suitable salts thereof,

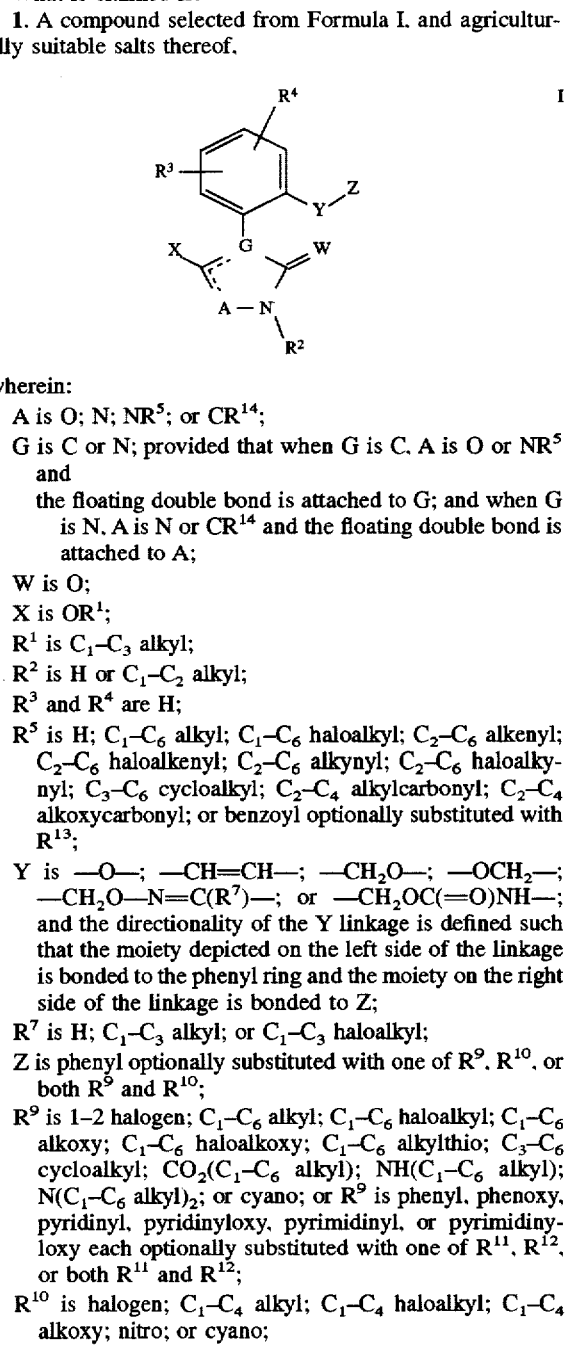

wherein:

A is O; N; NR$^5$; or CR$^{14}$;

G is C or N; provided that when G is C, A is O or NR$^5$ and
   the floating double bond is attached to G; and when G is N, A is N or CR$^{14}$ and the floating double bond is attached to A;

W is O;

X is OR$^1$;

R$^1$ is C$_1$–C$_3$ alkyl;

R$^2$ is H or C$_1$–C$_2$ alkyl;

R$^3$ and R$^4$ are H;

R$^5$ is H; C$_1$–C$_6$ alkyl; C$_1$–C$_6$ haloalkyl; C$_2$–C$_6$ alkenyl; C$_2$–C$_6$ haloalkenyl; C$_2$–C$_6$ alkynyl; C$_2$–C$_6$ haloalkynyl; C$_3$–C$_6$ cycloalkyl; C$_2$–C$_4$ alkylcarbonyl; C$_2$–C$_4$ alkoxycarbonyl; or benzoyl optionally substituted with R$^{13}$;

Y is —O—; —CH=CH—; —CH$_2$O—; —OCH$_2$—; —CH$_2$O—N=C(R$^7$)—; or —CH$_2$OC(=O)NH—; and the directionality of the Y linkage is defined such that the moiety depicted on the left side of the linkage is bonded to the phenyl ring and the moiety on the right side of the linkage is bonded to Z;

R$^7$ is H; C$_1$–C$_3$ alkyl; or C$_1$–C$_3$ haloalkyl;

Z is phenyl optionally substituted with one of R$^9$, R$^{10}$, or both R$^9$ and R$^{10}$;

R$^9$ is 1-2 halogen; C$_1$–C$_6$ alkyl; C$_1$–C$_6$ haloalkyl; C$_1$–C$_6$ alkoxy; C$_1$–C$_6$ haloalkoxy; C$_1$–C$_6$ alkylthio; C$_3$–C$_6$ cycloalkyl; CO$_2$(C$_1$–C$_6$ alkyl); NH(C$_1$–C$_6$ alkyl); N(C$_1$–C$_6$ alkyl)$_2$; or cyano; or R$^9$ is phenyl, phenoxy, pyridinyl, pyridinyloxy, pyrimidinyl, or pyrimidinyloxy each optionally substituted with one of R$^{11}$, R$^{12}$, or both R$^{11}$ and R$^{12}$;

R$^{10}$ is halogen; C$_1$–C$_4$ alkyl; C$_1$–C$_4$ haloalkyl; C$_1$–C$_4$ alkoxy; nitro; or cyano;

$R^{11}$ and $R^{12}$ are each independently halogen; $C_1$–$C_4$ alkyl; $C_1$–$C_4$ haloalkyl; $C_1$–$C_4$ alkoxy; $C_1$–$C_4$ haloalkoxy; nitro; or cyano;

$R^{13}$ is halogen; $C_1$–$C_3$ alkyl; $C_1$–$C_3$ haloalkyl; $C_1$–$C_3$ alkoxy; $C_1$–$C_3$ haloalkoxy; nitro; or cyano; and $R^{14}$ is H; halogen; $C_1$–$C_6$ alkyl; $C_1$–$C_6$ haloalkyl; $C_2$–$C_6$ alkenyl; $C_2$–$C_6$ haloalkenyl; $C_2$–$C_6$ alkynyl; $C_2$–C6 haloalkynyl; or $C_3$–$C_6$ cycloalkyl.

2. A compound of claim 1 wherein

A is O or $NR^5$;

G is C;

Y is —O—; —$CH_2$O—; —O$CH_2$—; or —$CH_2$O—N=C($R^7$)—; and $R^7$ is H; $C_1$–$C_2$ alkyl; or $C_1$–$C_2$ haloalkyl.

3. A compound of claim 1 wherein

A is N or $CR^{14}$;

G is N;

Y is —O—; —$CH_2$O—; —O$CH_2$—; or —$CH_2$O—N=C($R^7$)—; and $R^7$ is H; $C_1$–$C_2$ alkyl; or $C_1$–$C_2$ haloalkyl.

4. A compound of claim 3 wherein

A is N;

$R^1$ is methyl;

$R^2$ is methyl;

Y is —$CH_2$O—N=C($CH_3$)—;

$R^9$ is 1–2 halogen or $C_1$–$C_6$ haloalkyl; and $R^{10}$ is halogen or $C_1$–$C_4$ haloalkyl.

5. A compound of claim 4 wherein Z is phenyl or a substituted phenyl selected from the group consisting of 2-Br-Ph, 2,4-diCl-Ph, 2-$CF_3$-Ph, 2-I-Ph, 2-F-Ph, 3,5-diCl-Ph, 3,5-di$CF_3$-Ph, 2-Cl-Ph, 2,4,6-triCl-Ph, 4-Cl-Ph, 3-$CF_3$-Ph, 3-F-Ph, 4-$CF_3$-Ph, 3,4-diCl-Ph, 3,4-di$CF_3$-Ph, 4-Br-Ph, 4-F-Ph, and 3-Cl-Ph.

6. A fungicidal composition comprising an effective amount of a compound of claim 1 and at least one of (a) a surfactant, (b) an organic solvent, and (c) at least one solid or liquid diluent.

7. A method for controlling plant diseases caused by fungal plant pathogens comprising applying to the plant or portion thereof, or to the plant, seed or seedling, an effective amount of a compound of claim 1.

* * * * *